US010035926B2

(12) United States Patent
Toolis et al.

(10) Patent No.: US 10,035,926 B2
(45) Date of Patent: Jul. 31, 2018

(54) IONIC LIQUID CATALYSTS IN SULFUR-CONTAINING POLYMER COMPOSITIONS

(71) Applicant: PRC-DeSoto International, Inc., Sylmar, CA (US)

(72) Inventors: Amy Liane Toolis, Pittsburgh, PA (US); Lawrence G. Anderson, Allison Park, PA (US); Brianne N. Sawders-Georgic, Pittsburgh, PA (US)

(73) Assignee: PRC—DeSoto International, Inc., Sylmar, CA (US)

( * ) Notice: Subject to any disclaimer, the term of this patent is extended or adjusted under 35 U.S.C. 154(b) by 90 days.

(21) Appl. No.: 15/135,587

(22) Filed: Apr. 22, 2016

(65) Prior Publication Data

US 2017/0306181 A1    Oct. 26, 2017

(51) Int. Cl.

| | |
|---|---|
| *C08G 75/02* | (2016.01) |
| *C08G 75/00* | (2006.01) |
| *C09D 181/04* | (2006.01) |
| *C09D 181/02* | (2006.01) |
| *B05D 3/00* | (2006.01) |
| *C01G 45/02* | (2006.01) |
| *C07D 233/56* | (2006.01) |
| *C09C 3/00* | (2006.01) |
| *C09D 7/00* | (2018.01) |
| *C08K 3/22* | (2006.01) |
| *C09C 1/00* | (2006.01) |
| *C08K 5/14* | (2006.01) |
| *C09J 11/04* | (2006.01) |

(Continued)

(52) U.S. Cl.

CPC .............. *C09D 181/04* (2013.01); *B05D 3/00* (2013.01); *C01G 45/02* (2013.01); *C07D 233/56* (2013.01); *C08G 75/00* (2013.01); *C08K 3/22* (2013.01); *C08K 5/14* (2013.01); *C08L 81/04* (2013.01); *C09C 1/00* (2013.01); *C09C 3/00* (2013.01); *C09D 7/00* (2013.01); *C09D 181/02* (2013.01); *C09J 11/04* (2013.01); *C09J 181/04* (2013.01)

(58) Field of Classification Search

CPC ...................................................... C08G 75/02
USPC ........................................ 528/375, 373, 387
See application file for complete search history.

(56) References Cited

U.S. PATENT DOCUMENTS

| | | |
|---|---|---|
| 4,366,307 A | 12/1982 | Singh et al. |
| 4,609,762 A | 9/1986 | Morris et al. |

(Continued)

FOREIGN PATENT DOCUMENTS

| | | |
|---|---|---|
| CN | 102277013 A | 12/2011 |
| JP | 2009084469 | 4/2009 |
| WO | WO 2010/084938 A1 | 7/2010 |

OTHER PUBLICATIONS

Fedoseev et al., "1-Butyl-3-methylimidazolium Salts as New Catalysts to Prodice Epoxy-anhydride Polymers with Improved Properties", International Journal of Polymer Science, 2014, Article ID 607341, 8 pages.

(Continued)

*Primary Examiner* — Duc Truong

(74) *Attorney, Agent, or Firm* — William R. Lambert

(57) ABSTRACT

Compositions comprising thiol-terminated sulfur-containing prepolymers, curing agents reactive with the thiol-terminated sulfur-containing prepolymers, and ionic liquid catalysts, useful in aerospace sealant applications are disclosed. The use of ionic liquid catalysts provides curable sealant compositions having an extended working time and a rapid cure rate.

27 Claims, 6 Drawing Sheets

Cure Time

(51) Int. Cl.
*C09J 181/04* (2006.01)
*C08L 81/04* (2006.01)
*C09D 181/00* (2006.01)

(56) References Cited

U.S. PATENT DOCUMENTS

| | | | |
|---|---|---|---|
| 4,623,711 | A | 11/1986 | Morris et al. |
| 5,225,472 | A | 7/1993 | Cameron et al. |
| 5,270,364 | A | 12/1993 | Schwartz et al. |
| 5,284,888 | A | 2/1994 | Morgan |
| 6,172,179 | B1 | 1/2001 | Zook et al. |
| 6,372,849 | B2 | 4/2002 | DeMoss et al. |
| 6,525,168 | B2 | 2/2003 | Llatas et al. |
| 7,671,145 | B2 | 3/2010 | Sawant et al. |
| 8,541,513 | B2 | 9/2013 | Hobbs et al. |
| 8,710,159 | B2 | 4/2014 | Blackford et al. |
| 2004/0220327 | A1 | 11/2004 | Cosman et al. |
| 2005/0010003 | A1 | 1/2005 | Sawant et al. |
| 2006/0270796 | A1 | 11/2006 | Sawant et al. |
| 2007/0173602 | A1 | 7/2007 | Brinkman et al. |
| 2007/0287810 | A1 | 12/2007 | Rao et al. |
| 2008/0200610 | A1 | 8/2008 | Cosman |
| 2009/0326167 | A1 | 12/2009 | Sawant et al. |
| 2010/0010133 | A1 | 1/2010 | Zook et al. |
| 2010/0036063 | A1 | 2/2010 | Sawant et al. |
| 2010/0041839 | A1 | 2/2010 | Anderson et al. |
| 2010/0166971 | A1 | 7/2010 | Wittenbecher et al. |
| 2011/0319559 | A1 | 12/2011 | Kania et al. |
| 2012/0004349 | A1 | 1/2012 | Kaneko et al. |
| 2012/0040104 | A1 | 2/2012 | Keledjian et al. |
| 2012/0234205 | A1 | 9/2012 | Hobbs et al. |
| 2012/0238707 | A1 | 9/2012 | Hobbs et al. |
| 2012/0288632 | A1 | 11/2012 | Neu et al. |
| 2013/0284359 | A1 | 10/2013 | Virnelson |
| 2013/0345371 | A1 | 12/2013 | Anderson et al. |
| 2013/0345389 | A1 | 12/2013 | Cai et al. |
| 2014/0110881 | A1 | 4/2014 | Keledjian et al. |
| 2014/0272287 | A1 | 9/2014 | Cai et al. |
| 2014/0275461 | A1 | 9/2014 | Rao et al. |
| 2014/0275474 | A1 | 9/2014 | Rao et al. |
| 2014/0378649 | A1 | 12/2014 | Cai et al. |
| 2014/0378650 | A1 | 12/2014 | Rao et al. |
| 2015/0119549 | A1 | 4/2015 | Rao et al. |
| 2015/0252232 | A1 | 9/2015 | Keledjian et al. |

OTHER PUBLICATIONS

Lowry et al., "Cure evaluation of Intelimer latent curing agents for thermoset resin applications", presented at Thermoset Resin Formulators Association Meeting, Chicago, IL, Sep. 15-16, 2008.
Martell et al., "Coordination of Al (III) in the environment and in biological systems", Coordination Chemistry Reviews, 1996, vol. 149, pp. 311-328.
Mather et al., "Michael Addition Reactions in Macromolecular Design for Emerging Technologies", Prog. Polym. Sci., 2006, vol. 31, pp. 487-531.
Yokel., "Aluminum chelation principles and recent advantages", Coordination Chemistry Reviews, 2002, vol. 228, pp. 97-113.

IONIC LIQUID CATALYSTS IN SULFUR-CONTAINING POLYMER COMPOSITIONS

FIELD

The present disclosure relates to sulfur-containing prepolymer compositions containing ionic liquid catalysts and the use of ionic liquid catalysts in sulfur-containing prepolymer compositions. Ionic liquids are used to catalyze the curing reaction of thiol-terminated sulfur-containing prepolymers. Cured sealants prepared from the compositions exhibit properties useful in aerospace sealant applications.

BACKGROUND

Sealants used in aerospace and other applications must satisfy demanding mechanical, chemical, and environmental requirements. Sulfur-containing prepolymers such as polysulfides and polythioethers are suitable for use in aerospace sealant applications. Thiol-terminated sulfur-containing prepolymers can react with a curing agent in the presence of a catalyst to provide cured sealants. Many aerospace sealants exhibit a long working time such as from 2 hours to 48 hours, and an even longer curing time, for example, up to 56 days. In certain applications it is desirable that a curable sealant composition have a long working time such as from 2 days to 10 days and short cure time such as less than 2 days. Although an increased amount of catalyst may be added to shorten the curing time, even in small amounts a catalyst can have a detrimental effect on the properties of the cured sealant. For example, amine catalysts used in thiol-epoxy curing chemistries and oxidants such as manganese dioxide used in thiol-condensation curing can reduce the tensile strength and elongation of the cured sealant.

Therefore, it is desirable to develop improved catalyst systems for use with thiol-terminated sulfur-containing prepolymer compositions that exhibit an extended working time, a fast cure rate, and provide a cured sealant exhibiting acceptable performance for aerospace applications.

SUMMARY

The use of ionic liquid catalysts in sulfur-containing prepolymer compositions that exhibit an extended working time, cure rapidly, and result in cured sealants exhibiting enhanced properties suitable for use in aerospace sealant applications are disclosed.

According to the present invention, compositions can comprise a thiol-terminated sulfur-containing prepolymer; a curing agent comprising two or more terminal groups reactive with thiol groups; and an ionic liquid catalyst.

According to the present invention, cured sealants prepared from an inventive composition of the present disclosure are provided.

According to the present invention, parts comprising the cured sealant prepared from an inventive composition of the present disclosure are provided.

According to the present invention, methods of sealing a part comprise applying an inventive composition of the present disclosure to at least a portion of a surface of a part; and curing the applied composition to seal the part.

Reference is now made to certain compositions, sealants, and methods of the present invention. The disclosed compositions, sealants, and methods are not intended to be limiting of the claims. To the contrary, the claims are intended to cover all alternatives, modifications, and equivalents.

Figure 1:
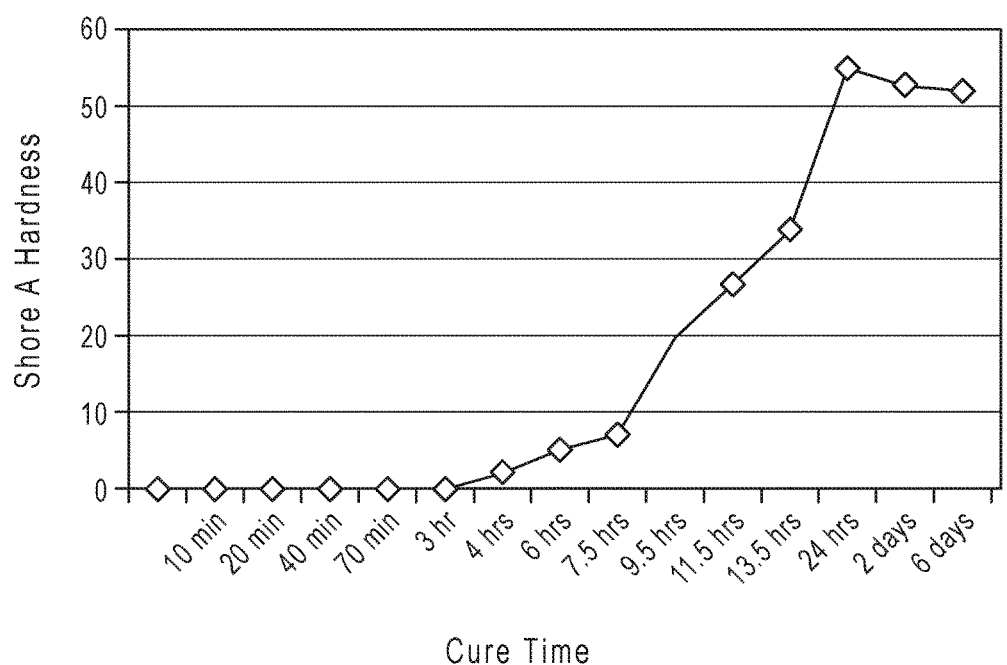
FIG. 1 shows the Shore A hardness during cure of a manganese dioxide-cured polysulfide sealant composition without an ionic liquid co-catalyst.

Reference is now made to certain embodiments of compositions and methods. The disclosed embodiments are not intended to be limiting of the claims. To the contrary, the claims are intended to cover all alternatives, modifications, and equivalents.

DETAILED DESCRIPTION

For purposes of the following description, it is to be understood that embodiments provided by the present disclosure may assume various alternative variations and step sequences, except where expressly specified to the contrary. Moreover, other than in the examples, or where otherwise indicated, all numbers expressing, for example, quantities of ingredients used in the specification and claims are to be understood as being modified in all instances by the term "about." Accordingly, unless indicated to the contrary, the numerical parameters set forth in the following specification and attached claims are approximations that may vary depending upon the desired properties to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges encompassed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. Also, in this application, the use of "or" means "and/or" unless specifically stated otherwise, even though "and/or" may be explicitly used in certain instances.

A dash ("-") that is not between two letters or symbols is used to indicate a point of covalent bonding for a substituent or between two atoms. For example, the chemical group —CONH$_2$ is covalently bonded to another chemical moiety through the carbon atom. In certain instances, the expression "-" is used to denote the point of bonding.

"Alkanearene" refers to a hydrocarbon group having one or more aryl and/or arenediyl groups and one or more alkyl and/or alkanediyl groups, where aryl, arenediyl, alkyl, and alkanediyl are defined herein. Each aryl and/or arenediyl group(s) can be $C_{6-12}$, $C_{6-10}$, phenyl or benzene-diyl. Each alkyl and/or alkanediyl group(s) can be $C_{1-6}$, $C_{1-4}$, $C_{1-3}$, methyl, methanediyl, ethyl, or ethane-1,2-diyl. An alkanearene group can be $C_{4-18}$ alkanearene, $C_{4-16}$ alkanearene, $C_{4-12}$ alkanearene, $C_{4-8}$ alkanearene, $C_{6-12}$ alkanearene, $C_{6-10}$ alkanearene, or $C_{6-9}$ alkanearene. Examples of alkanearene groups include diphenyl methane.

"Alkanearenediyl" refers to a diradical of an alkanearene group. An alkanearenediyl group can be $C_{4-18}$ alkanearenediyl, $C_{4-16}$ alkanearenediyl, $C_{4-12}$ alkanearenediyl, $C_{4-8}$ alkanearenediyl, $C_{6-12}$ alkanearenediyl, $C_{6-10}$ alkanearenediyl, or $C_{6-9}$ alkanearenediyl. Examples of alkanearenediyl groups include diphenyl methane-4,4'-diyl.

"Alkanediyl" refers to a diradical of a saturated, branched or straight-chain, acyclic hydrocarbon group, having, for example, from 1 to 18 carbon atoms ($C_{1-18}$), from 1 to 14 carbon atoms ($C_{1-14}$), from 1 to 6 carbon atoms ($C_{1-6}$), from 1 to 4 carbon atoms ($C_{1-4}$), or from 1 to 3 hydrocarbon atoms ($C_{1-3}$). It will be appreciated that a branched alkanediyl has a minimum of three carbon atoms. An alkanediyl can be $C_{2-14}$ alkanediyl, $C_{2-10}$ alkanediyl, $C_{2-8}$ alkanediyl, $C_{2-6}$ alkanediyl, $C_{2-4}$ alkanediyl, or $C_{2-3}$ alkanediyl. Examples of alkanediyl groups include methane-diyl (—CH$_2$—), ethane-1,2-diyl (—CH$_2$CH$_2$—), propane-1,3-diyl and iso-propane-1,2-diyl (e.g., —CH$_2$CH$_2$CH$_2$— and —CH(CH$_3$)CH$_2$—), butane-1,4-diyl (—CH$_2$CH$_2$CH$_2$CH$_2$—), pentane-1,5-diyl (—CH$_2$CH$_2$CH$_2$CH$_2$CH$_2$—), hexane-1,6-diyl (—CH$_2$CH$_2$CH$_2$CH$_2$CH$_2$CH$_2$—), heptane-1,7-diyl, octane-1,8-diyl, nonane-1,9-diyl, and decane-1,10-diyl, dodecane-1,12-diyl.

"Alkanecycloalkane" refers to a saturated hydrocarbon group having one or more cycloalkyl and/or cycloalkanediyl groups and one or more alkyl and/or alkanediyl groups, where cycloalkyl, cycloalkanediyl, alkyl, and alkanediyl are defined herein. Each cycloalkyl and/or cycloalkanediyl group(s) can be $C_{3-6}$, $C_{5-6}$, cyclohexyl or cyclohexanediyl. Each alkyl and/or alkanediyl group(s) can be $C_{1-6}$, $C_{1-4}$, $C_{1-3}$, methyl, methanediyl, ethyl, or ethane-1,2-diyl. An alkanecycloalkane group can be $C_{4-18}$ alkanecycloalkane, $C_{4-16}$ alkanecycloalkane, $C_{4-12}$ alkanecycloalkane, $C_{4-8}$ alkanecycloalkane, $C_{6-12}$ alkanecycloalkane, $C_{6-10}$ alkanecycloalkane, or $C_{6-9}$ alkanecycloalkane. Examples of alkanecycloalkane groups include 1,1,3,3-tetramethylcyclohexane and cyclohexylmethane.

"Alkanecycloalkanediyl" refers to a diradical of an alkanecycloalkane group. An alkanecycloalkanediyl group can be $C_{4-18}$ alkanecycloalkanediyl, $C_{4-16}$ alkanecycloalkanediyl, $C_{4-12}$ alkanecycloalkanediyl, $C_{4-8}$ alkanecycloalkanediyl, $C_{6-12}$ alkanecycloalkanediyl, $C_{6-10}$ alkanecycloalkanediyl, or $C_{6-9}$ alkanecycloalkanediyl. Examples of alkanecycloalkanediyl groups include 1,1,3,3-tetramethylcyclohexane-1,5-diyl and cyclohexylmethane-4,4'-diyl.

"Alkenyl" refers to a group having the structure —C(—R)=CR$_2$ where the alkenyl group is a terminal group and is bonded to a molecule. In such embodiments, each R may be selected from, for example, hydrogen and $C_{1-3}$ alkyl. Each R can be hydrogen and an alkenyl group has the structure —CH=CH$_2$.

"Alkoxy" refers to a —OR group where R is alkyl as defined herein. Examples of alkoxy groups include methoxy, ethoxy, n-propoxy, isopropoxy, and n-butoxy. An alkoxy group can be $C_{1-8}$ alkoxy, $C_{1-6}$ alkoxy, $C_{1-4}$ alkoxy, or $C_{1-3}$ alkoxy.

"Alkyl" refers to a monoradical of a saturated, branched or straight-chain, acyclic hydrocarbon group having, for example, from 1 to 20 carbon atoms, from 1 to 10 carbon atoms, from 1 to 6 carbon atoms, from 1 to 4 carbon atoms, or from 1 to 3 carbon atoms. It will be appreciated that a branched alkyl has a minimum of three carbon atoms. An alkyl group can be $C_{1-6}$ alkyl, $C_{1-4}$ alkyl, or $C_{1-3}$ alkyl. Examples of alkyl groups include methyl, ethyl, n-propyl, iso-propyl, n-butyl, iso-butyl, tert-butyl, n-hexyl, n-decyl, and tetradecyl. An alkyl group can be $C_{1-6}$ alkyl, $C_{1-4}$ alkyl, or $C_{1-3}$ alkyl. It will be appreciated that a branched alkyl has at least three carbon atoms.

"Aryl" refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. An aryl group can have from 6 to 20 carbon atoms, or from 6 to 12 carbon atoms. Aryl, however, does not encompass or overlap with heteroaryl, separately defined herein. Hence, a multiple ring system in which one or more carbocyclic aromatic rings is fused to a heterocycloalkyl aromatic ring, is heteroaryl, not aryl, as defined herein. An aryl group is phenyl.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group can be $C_{1-6}$ and the aryl moiety is $C_{6-10}$. An arylalkyl group can be $C_{7-9}$ arylalkyl, wherein the alkyl moiety is $C_{1-3}$ alkyl and the aryl moiety is phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

A "curable composition" refers to a composition that comprises at least two reactants capable of reacting to form a cured composition. For example, a curable composition can comprise a thiol-terminated polythioether prepolymer and a polyepoxide capable of reacting to form a cured polymer network. A curable composition may include a catalyst for the curing reaction and other components such as, for example, fillers, pigments, and adhesion promoters. A curable composition may be curable at ambient conditions such as room temperature and humidity, or may require exposure to elevated temperature, moisture, or other condition to initiate and/or accelerate the curing reaction. A curable composition may initially be provided as a two part composition including a base component and an accelerator component. The base composition can contain one of the reactants participating in the curing reaction such as a thiol-terminated polythioether prepolymer and the accelerator composition can contain the other reactant such as a polyepoxide. The two compositions can be mixed shortly before use to provide a curable composition. A curable composition can exhibit a viscosity suitable for a particular method of application. For example, a Class A sealant composition, which is suitable for brush-on applications can be characterized by a viscosity from 150 Poise to 500 Poise. A Class B sealant composition, which is suitable for fillet seal applications can be characterized by a viscosity from 8,000 Poise to 16,000 Poise. A Class C sealant composition, which is suitable for fay seal applications can be characterized by a viscosity from 1,000 Poise to 4,000 Poise. After the two compositions are combined and mixed, the curing reaction can proceed and the viscosity of the curable composition can increase and at some point the curable composition will no longer be workable. The period of time between when the two components are mixed to form the curable composition and when the curable composition can no longer be reasonably applied to a surface for its intended purpose is referred to as the working time. As can be appreciated, the working time can depend on a number of factors including, for example, the curing chemistry, the application method, and the temperature. The working time can also be referred to as the pot life. Once a curable composition is applied to a surface (and during application), the curing reaction proceeds to provide a cured composition. A cured composition develops a tack-free surface and fully cures over a period of time. A curable composition can be considered to be cured when the surface is tack-free, or can be considered cured when the Shore A hardness of the surface is 20, Shore A 30, or Shore A 40. It will be appreciated that although a composition cures to a certain Shore A hardness, the sealant can develop a full cure over time, which can be from several days to several weeks.

"Cycloalkanediyl" refers to a diradical saturated monocyclic or polycyclic hydrocarbon group. A cycloalkanediyl group can be $C_{3-12}$ cycloalkanediyl, $C_{3-8}$ cycloalkanediyl, $C_{3-6}$ cycloalkanediyl, or $C_{5-6}$ cycloalkanediyl. Examples of cycloalkanediyl groups include cyclohexane-1,4-diyl, cyclohexane-1,3-diyl, and cyclohexane-1,2-diyl.

"Cycloalkyl" refers to a saturated monocyclic or polycyclic hydrocarbon monoradical group. A cycloalkyl group can be $C_{3-12}$ cycloalkyl, $C_{3-8}$ cycloalkyl, $C_{3-6}$ cycloalkyl, or $C_{5-6}$ cycloalkyl.

"Heteroalkanediyl" refers to an alkanediyl group in which one or more of the carbon atoms are replaced with a heteroatom, such as N, O, S, or P. In a heteroalkanediyl, a heteroatom can be selected from N and O.

"Heteroalkanearenediyl" refers to an alkanearenediyl group in which one or more of the carbon atoms are replaced with a heteroatom, such as N, O, S, or P. In a heteroalkanearenediyl, a heteroatom can be selected from N and O.

"Heterocycloalkanediyl" refers to a cycloalkanediyl group in which one or more of the carbon atoms are replaced with a heteroatom, such as N, O, S, or P. In a heterocycloalkanediyl, a heteroatom can be selected from N and O.

"Derived from" refers to a functional group or moiety that is created following reaction with another reactive functional group or moiety. For example, the moiety —$CH_2$—$CH_2$—S— can be derived from the reaction of an alkenyl group, —CH=$CH_2$ with a thiol group —SH. Similarly, the moiety —S— can be derived from the reaction of —SH with a group that is reactive with thiol groups. A group —R'— can be derived from the reaction of the group —R with a group reactive with R. A moiety —R' can be derived from the reaction of a compound R with a reactive group.

Core of a sulfur-containing prepolymer or adduct refers to a moiety forming the sulfur-containing prepolymer or adduct without the terminal functional groups or moieties comprising a terminal functional group. For example, the core of sulfur-containing prepolymer or adduct having the structure $R^f$—R—$R^f$ where each $R^f$ represents a moiety comprising a terminal functional group or a terminal functional group, is —R—. A core can refer to a repeat unit of a prepolymer, such as, for example, the prepolymer $R^f$—[R']$_n$—R—$R^f$ where —[R']$_n$— represents the core.

Core of a diisocyanate refers to the moiety forming the diisocyanate without the terminal isocyanate groups. For example, a core of a diisocyanate having the structure O=C=N—R—N=C=O is represented by —R—.

A "Michael acceptor" refers to an activated alkene, such as an alkenyl group proximate to an electron-withdrawing group such as, for example, a ketone (=O), halo, carbonyl (—CO), nitro (—$NO_2$), nitrile (—CN), alkoxycarbonyl (—COOR), phosphonate (—PO(OR)$_2$), trifluoromethyl (—$CF_3$), sulfonyl (—$SO_2$—), trifluoromethanesulfonyl (—$SO_2CF_3$), or p-toluenesulfonyl (—$SO_2$—$C_6H_4$—$CH_3$). A Michael acceptor group can be selected from a vinyl ketone, a vinyl sulfone, a quinone, an enamine, a ketimine, an aldimine, an oxazolidine, a maleimide, and an acrylate. In certain embodiments, a Michael acceptor or Michael acceptor group does not encompass acrylates or methacrylates. Other examples of Michael acceptors are disclosed in Mather et al., *Prog. Polym. Sci.* 2006, 31, 487-531, and include acrylate esters, acrylonitrile, acrylamides, maleimides, alkyl methacrylates, cyanoacrylates. Other Michael acceptors include vinyl ketones, α,β-unsaturated aldehydes, vinyl phosphonates, acrylonitrile, vinyl pyridines, certain azo compounds, β-keto acetylenes and acetylene esters. A Michael acceptor group can be derived from a vinyl sulfone and can have the structure of Formula (1):

where R can be hydrogen, fluorine, or $C_{1-3}$ alkyl. In moieties of Formula (1), R can be hydrogen.

A "Michael acceptor compound" refers to a compound comprising at least one Michael acceptor group. A Michael acceptor compound can be a divinyl sulfone, and a Michael acceptor group is vinylsulfonyl, e.g., —S(O)$_2$—CH=CH$_2$. Other examples of Michael acceptors are disclosed in Mather et al., *Prog. Polym. Sci.*, 2006, 31, 487-531, and include acrylate esters, acrylonitrile, acrylamides, maleimides, alkyl methacrylates, cyanoacrylates. Types of compounds that function as Michael acceptors include vinyl ketones, quinones, nitroalkenes, acrylonitriles, acrylates, methacrylates, cyanoacrylates, acrylamides, maleimides, dialkyl vinylphosphonate, and vinylsulfones. Other Michael acceptors include vinyl ketones, α,β-unsaturated aldehydes, vinyl phosphonates, acrylonitrile, vinyl pyridines, certain azo compounds, β-keto acetylenes and acetylene esters. A Michael acceptor compound can be a bis(vinylsulfonyl) alkanol, and the Michael acceptor group is 1-(ethylenesulfonyl)-n-(vinylsulfonyl)alkanol, i.e., —CH$_2$—CH$_2$—S(O)$_2$—R$^{10}$—CH(—OH)—R$^{10}$—S(O)$_2$—CH=CH$_2$, where each R$^{10}$ can be independently selected from $C_{1-3}$ alkanediyl; or 1-(ethylenesulfonyl)-3-(vinylsulfonyl)propan-2-ol (—CH$_2$—CH$_2$—S(O)$_2$—CH$_2$—CH(—OH)—CH$_2$—S(O)$_2$—CH=CH$_2$). In certain embodiments, a Michael acceptor does not comprise an acrylate or a methacrylate.

Michael acceptor compounds having more than one Michael acceptor group are also well known. Examples include diacrylates such as ethylene glycol diacrylate and diethylene glycol diacrylate, dimethacrylates such as ethylene glycol methacrylate and diethylene glycol methacrylate, bismaleimides such as N,N'-(1,3-phenylene)dimaleimide and 1,1'-(methylenedi-4,1-phenylene)bismaleimide, vinylsulfones such as divinyl sulfone and 1,3-bis(vinylsulfonyl)-2-propanol. A Michael acceptor group can be a divinyl sulfonyl having the structure of Formula (2a) or Formula (2b):

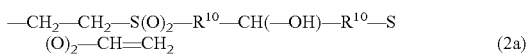

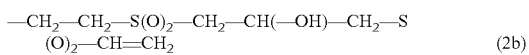

where each R$^{10}$ is independently selected from $C_{1-3}$ alkanediyl.

A "metal ligand" refers to an ion or molecule that binds to a metal atom and potentially other atoms to form a coordination complex. The bonding between the metal and or atoms generally involves donation of one or more electron pairs to the metal and the nature of the bonding can be covalent or ionic. Metal ligands provided by the present disclosure are capable of forming coordination complexes to aerospace surfaces such as aluminum and titanium surfaces, which may be oxidized. In the case of oxidized surfaces a metal ligand may form a coordination complex with a metal such as Al(III) and oxygen atoms. The coordination complex can enhance the adhesion of a coating or sealant to the metal or oxidized metal surface.

Metal ligands may be incorporated into the backbone of a prepolymer. Such reactive metal ligands may be commercially available or may be derivatized to include appropriate reactive substituent groups using methods known to those skilled in the art. Examples of sulfur-containing prepolymers incorporating metal ligands are disclosed in U.S. Application Publication No. 2014/0378650, and U.S. Application Publication No. 2014/0275474, each of which is incorporated by reference in its entirety.

Hydroxypyridinones comprise groups such as 3-hydroxy-4-pyridinone and 3-hydroxy-2-pyridinone having the structure of Formula (3a) or Formula (3b), respectively:

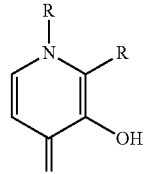

where R is an organic groups such as an alkyl group. A metal ligand derived from a hydroxypyridinone comprises a hydroxypyridinone group and one or more reactive functional groups such as terminal thiol groups.

An "acetylacetonate group" refers to a group having the structure:

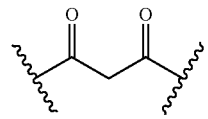 [SMILES: *C(=O)CC(*)=O]

An acetylacetonate refers to a metal chelating agent comprising an acetylacetonate ligand and one or more reactive functional groups. The one or more reactive functional groups can be reactive with a thiol group such as an epoxy group, an alkenyl group, a Michael acceptor group, or a group comprising a saturated carbon bearing a leaving group for nucleophilic substitution such as, for example, —Cl, —Br, —I, —OSO$_2$CH$_3$ (mesylate), —OSO$_2$—C$_6$H$_4$—CH$_3$ (tosylate), etc.

"Quinones" refer to compounds having a fully conjugated cyclic dione structure derived from aromatic compounds by conversion of an even number of —CH= groups into —C(=O)— groups with any necessary rearrangement of double bonds. Examples of quinones include 1,2-benzoquinone, 1,4-benzoquinone, 1,4-naphthaloquinone, and 9,10-anthraquinone. Quinone groups can be metal ligands.

A "maleimide" refers to a compound having a maleimide group:

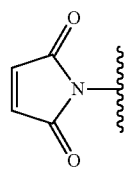 [SMILES: *N1C(=O)C=CC1=O]

A bismaleimide refers to a compound having two maleimide groups, where the two maleimide groups are bonded by the nitrogen atoms via a linker. Maleimide-terminated sulfur-containing prepolymers are disclosed in U.S. Application Publication No. 2015/0119549, which is incorporated by reference in its entirety.

A terminal bismaleimide moiety refers to a moiety having a terminal maleimide group. A terminal maleimide group can be derived from a bismaleimide, such as a compound having the structure of Formula (4a):

(4a)

where $R^{15}$ is a divalent organic moiety, and the terminal group has the structure of Formula (4b):

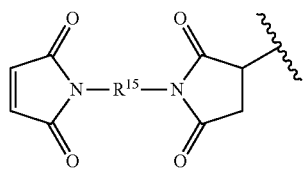
(4b)

and is referred to herein as a 1-(4-(4-(3-yl-2,5-dioxopyrrolidin-1-yl)benzyl)phenyl)-1H-pyrrole-2,5-dione group. A terminal maleimide group can be derived from 1,1'-(methylenedi-4,1-phenylene)bismaleimide of Formula (5a), also referred to as 1,1'-(methylenebis(4,1-phenylene)bis(1H-pyrrole-2,5-dione), and the terminal group has the structure of Formula (5b):

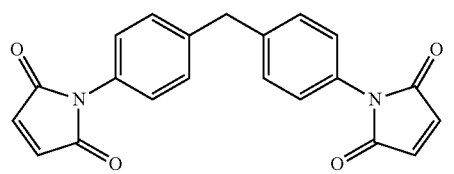
(5a)

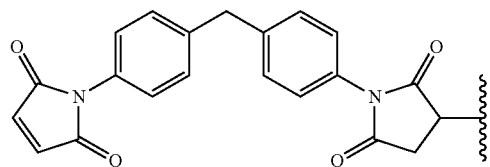
(5b)

A maleimide group can comprise a 1-(4-(4-(3-yl-2,5-dioxopyrrolidin-1-yl)benzyl)phenyl)-1H-pyrrole-2,5-dione group. Each of the terminal maleimide groups may be the same or at least some of the terminal maleimide groups may be different.

Other examples of compounds having two or more maleimide groups include ethylenebismaleimide, 1,6-bis-maleimidohexane, 2,4-dimaleimidotoluene, N,N'-1,3-phenylenedimaleimide, 1,4-bis(maleimido)butane trimethylenebismaleimide, p,p'-dimaleimidodiphenylmethane, pentamethylenebismaleimide 1H-pyrrole-2,5-dione, 1,1'-(1,8-octanediyl)bis-, 1H-pyrrole-2,5-dione, 1,1'-(1,7-heptanediyl)bis-, 4,4'-dithiobis(phenylmaleimide); methylenebis(N-carbamylmaleimide), 1,9-bis(maleimide)nonane, 1,1'-decane-1,10-diylbis(1H-pyrrole-2,5-dione), O-phenylene dimaleimide, bis(N-maleimidomethyl)ether, 1,5-bis(maleimide)-2-methyl-pentane, N,N'-1,4-phenylenedimaleimide, 1,1'-(2-methyl-1,3-phenylene)bis(1H-pyrrole-2,5-dione), Kerimid 601 resin, tetrakis(N-2-aminoethylmaleimide), 1-(2,5-dimethylphenyl)pyrrole-2,5-dione, SureCN331305, SureCN349749, and 1,1'-biphenyl-4,4'-diylbis(1H-pyrrole-2,5-dione).

A "bis(sulfonyl)alkanol" refers to a compound of the general formula $R^8$—$S(O)_2$—$R^{10}$—$CH(-OH)$—$R^{10}$—$S(O)_2$—$R^8$ where each $R^8$ is a moiety having a reactive functional group; and each $R^{10}$ is independently selected from $C_{1-3}$ alkanediyl. Each $R^8$ can comprise a terminal group reactive with a thiol group such as, for example, an alkenyl group, an epoxy group, a Michael acceptor group, or a group comprising a saturated carbon bearing a leaving group suited for nucleophilic substitution such as, for example, —Cl, —Br, —I, —$OSO_2CH_3$ (mesylate), —$OSO_2$—$C_6H_4$—$CH_3$ (tosylate), etc. A bis(sulfonyl)alkanol may be a bis(vinylsulfonyl)alkanol comprising terminal alkenyl groups. A bis(sulfonyl)alkanol may be a bis(vinylsulfonyl)alkanol in which $R^8$ comprises a terminal alkenyl group, such as a compound having the formula $CH_2$=CH—$S(O)_2$—$R^{10}$—$CH(-OH)$—$R^{10}$—$S(O)_2$—CH=$CH_2$. A bis(vinylsulfonyl)alkanol can be 1,3-bis(vinylsulfonyl)-2-propanol. A bis(sulfonyl)alkanol containing compound may be prepared by reacting a bis(vinylsulfonyl)alkanol with a compound having a reactive terminal functional group and a terminal group reactive with the terminal alkenyl groups of the bis(vinylsulfonyl)alkanol such as a thiol group or an epoxy group. In such compounds, the bis(sulfonyl)alkanol can have the structure $R^{8'}$—$CH_2$—$CH_2$—$S(O)_2$—$R^{10}$—$CH(-OH)$—$R^{10}$—$S(O)_2$—$CH_2$—$CH_2$—$R^{8'}$ where each $R^{8'}$ is a moiety derived from the reaction of the compound with the terminal alkenyl groups of the bis(vinylsulfonyl)alkanol.

As used herein, "prepolymer" refers to oligomers, homopolymers, and copolymers, which may be cured or uncured. Unless stated otherwise, molecular weights are number average molecular weights for polymeric materials indicated as "$M_n$" as determined, for example, by gel permeation chromatography using a polystyrene standard in an art-recognized manner.

"Prepolymers" refer to polymers prior to curing. In general, prepolymers provided by the present disclosure are liquid at room temperature. "Adducts" can refer to prepolymers that are functionalized with a reactive terminal group; however, prepolymers may also contain terminal functional groups. Thus, the terms prepolymer and adduct can be used interchangeably. The term adduct is often used to refer to a prepolymer with terminal groups functionalized for a particular chemistry.

"Polyalkenyl" refers to a compound having two or more terminal alkenyl groups.

"Polysulfide" refers to a prepolymer that contains one or more polysulfide linkages, i.e., —$S_x$— linkages, where x is from 2 to 4, in the prepolymer backbone and/or in pendent positions on the polymer chain. A polysulfide prepolymer will have two or more sulfur-sulfur linkages. Suitable polysulfides are commercially available, for example, from AkzoNobel and Toray Fine Chemicals under the names Thiokol®-LP and Thioplast®. Thioplast® products are available in a wide range of molecular weights, for example, from less than 1,100 Daltons to over 8,000 Daltons, with molecular weight being the average molecular weight in grams per mole. In some cases, a polysulfide has a number average molecular weight with the range of 1,000 Daltons to 4,000 Daltons. The crosslink density of these products also varies, depending on the amount of crosslinking agent used. The —SH content, i.e., thiol or mercaptan content, of these products can also vary. The mercaptan content and molecular weight of the polysulfide can affect the cure rate of the polymer, with cure rate increasing with molecular weight.

A "polythioether" refers to a prepolymer comprising at least one polythioether linkage, i.e., —$CH_2$—S—$CH_2$—. A polythioether prepolymer can have, for example, from 8 to 200 polythioether linkages. Polythioethers suitable for use in the present invention include those described, for example, in U.S. Pat. No. 6,372,849. Suitable polythioethers can have a number average molecular weight, for example from 1,000 Daltons to 10,000 Daltons, such as 2,000 Daltons to 5,000 Daltons or 3,000 Daltons to 4,000 Daltons. Examples of suitable polythioethers are available from PRC-DeSoto International, Inc., under the tradename Permapol®, such as Permapol® P-3.1e or Permapol® P-3.

"Substituted" refers to a group in which one or more hydrogen atoms are each independently replaced with the same or different substituent(s). A substituent can be selected from halogen, —$S(O)_2OH$, —$S(O)_2$, —SH, —SR where R is $C_{1-6}$ alkyl, —COOH, —$NO_2$, —$NR_2$ where each R is independently selected from hydrogen and $C_{1-3}$ alkyl, —CN, —C=O, $C_{1-6}$ alkyl, —$CF_3$, —OH, phenyl, $C_{2-6}$ heteroalkyl, $C_{5-6}$ heteroaryl, $C_{1-6}$ alkoxy, and —COR where R is $C_{1-6}$ alkyl. A substituent is chosen from —OH, —$NH_2$, and $C_{1-3}$ alkyl.

Compositions provided by the present disclosure comprise a thiol-terminated sulfur-containing prepolymer, a curing agent comprising two or more terminal groups reactive with thiol groups, and an ionic liquid catalyst.

A thiol-terminated sulfur-containing prepolymer can be a thiol-terminated polysulfide prepolymer, a thiol-terminated polythioether prepolymer, a thiol-terminated sulfur-containing polyformal prepolymer, or a combination of any of the foregoing.

A thiol-terminated sulfur-containing prepolymer may have sulfone, urethane, and/or metal ligands incorporated into the prepolymer backbone. Examples of such sulfur-containing prepolymers are disclosed, for example, in U.S. Application Publication No. 2014/0275474 and U.S. Application Publication No. 2014/0378650, each of which is incorporated by reference in its entirety.

A thiol-terminated sulfur-containing prepolymer may comprise a mixture of different thiol-terminated sulfur-containing prepolymers and the thiol-terminated sulfur-containing prepolymers may have the same or different functionality. A thiol-terminated sulfur-containing prepolymer can have an average functionality from 2 to 6, from 2 to 4, from 2 to 3, or from 2.05 to 2.5. For example, a thiol-terminated sulfur-containing prepolymer can comprise a difunctional thiol-terminated sulfur-containing prepolymer, a trifunctional thiol-terminated sulfur-containing prepolymer, or a combination thereof.

A thiol-terminated sulfur-containing prepolymer can comprise a thiol-terminated polysulfide prepolymer.

Polysulfides refer to prepolymers that contain one or more sulfide linkages, i.e., —$S_x$— linkages, where x is from 2 to 4, in the polymer backbone and/or in pendent positions on the prepolymer chain. A polysulfide prepolymer can have two or more sulfur-sulfur linkages. Suitable thiol-terminated polysulfides prepolymers are commercially available, for example, from AkzoNobel and Toray Fine Chemicals under the names Thiokol®-LP and Thioplast®. Thioplast® products are available in a wide range of molecular weights ranging, for example, from less than 1,100 Daltons to over 8,000 Daltons, with molecular weight being the average molecular weight in grams per mole. In some cases, a polysulfide prepolymer may have a number average molecular weight of 1,000 Daltons to 4,000 Daltons. Examples of suitable thiol-terminated polysulfide prepolymers are disclosed, for example, in U.S. Pat. No. 4,623,711.

A thiol-terminated sulfur-containing prepolymer can comprise a thiol-terminated polythioether prepolymer.

A thiol-terminated sulfur-containing prepolymer can comprise a thiol-terminated polythioether prepolymer comprising a backbone having the structure of Formula (6):

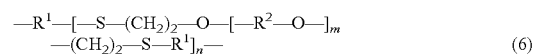

wherein,
each $R^1$ is independently selected from a $C_{2-10}$ n-alkanediyl group, a $C_{3-6}$ branched alkanediyl group, a $C_{6-8}$ cycloalkanediyl group, a $C_{6-10}$ alkanecycloalkanediyl group, a heterocyclic group, a -[(—$CHR^3$—)$_p$—X—]$_q$—($CHR^3$)$_r$— group, wherein each $R^3$ is selected from hydrogen and methyl;
each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a -[(—$CH_2$—)$_p$—X—]$_q$—($CH_2$)$_r$— group;
each X is independently selected from O, S, —NH—, and —N(—$CH_3$)—;
m ranges from 0 to 50;
n is an integer ranging from 1 to 60;
p is an integer ranging from 2 to 6;
q is an integer ranging from 1 to 5; and
r is an integer ranging from 2 to 10.

In prepolymers of Formula (6), $R^1$ can be -[—($CHR^3$)$_p$—X—]$_q$—($CHR^3$)$_r$— wherein each X can be independently selected from —O— and —S—. In a prepolymer of Formula (6) $R^1$ can be -[—($CHR^3$)$_p$—X—]$_q$—($CHR^3$)$_r$—, and each X can be —O— or each X can be —S—.

In prepolymers of Formula (6), $R^1$ can be -[—($CH_2$)$_p$—X—]$_q$—($CH_2$)$_r$— wherein each X can be independently selected from —O— and —S—. In prepolymers of Formula (6), $R^1$ can be -[—($CH_2$)$_p$—X—]$_q$—($CH_2$)$_r$—, each X can be —O— or each X can be —S—.

In prepolymers of Formula (6), $R^1$ can be -[(—$CH_2$—)$_p$—X—]$_q$—($CH_2$)$_r$—, where p can be 2, X can be O, q can be 2, r can be 2, $R^2$ is ethanediyl, m can be 2, and n can be 9.

In prepolymers of Formula (6), each $R^1$ can be derived from dimercaptodioxaoctane (DMDO) or each $R^1$ can be derived from dimercaptodiethylsulfide (DMDS).

In prepolymers of Formula (6), each $R^2$ can be $C_{2-6}$ alkanediyl, ethanediyl, 1,3-propanediyl, 1,4-butanediyl, 1,5-pentanediyl, or 1,6-hexanediyl.

In prepolymers of Formula (6), each m can be independently an integer from 1 to 3. In prepolymers of Formula (6), each m can be the same and is 1, 2, or 3.

In prepolymers of Formula (6), n can be an integer from 1 to 30, an integer from 1 to 20, an integer from 1 to 10, or an integer from 1 to 5. In addition, n may be any integer from 1 to 60.

In prepolymers of Formula (6), each p can be independently selected from 2, 3, 4, 5, and 6. In prepolymers of Formula (6), each p can be the same and is 2, 3, 4, 5, or 6.

Examples of suitable thiol-terminated polythioether prepolymers are disclosed, for example, in U.S. Pat. No. 6,172,179. A thiol-terminated polythioether may comprise Permapol® P3.1E, available from PRC-DeSoto International Inc.

A thiol-terminated sulfur-containing prepolymer can comprise a thiol-terminated polythioether prepolymer of Formula (7a), a thiol-terminated polythioether prepolymer of Formula (7b), or a combination thereof:

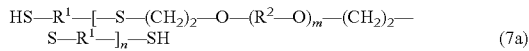

(7a)

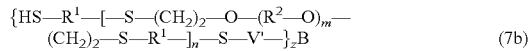

(7b)

wherein,
each $R^1$ independently is selected from $C_{2-10}$ alkanediyl, $C_{6-8}$ cycloalkanediyl, $C_{6-14}$ alkanecycloalkanediyl, $C_{5-8}$ heterocycloalkanediyl, and -[(—$CHR^3$—)$_p$—X—]$_q$—(—$CHR^3$—)$_r$—, wherein,
p is an integer from 2 to 6;
q is an integer from 1 to 5;
r is an integer from 2 to 10;
each $R^3$ is independently selected from hydrogen and methyl; and
each X is independently selected from —O—, —S—, —NH—, and —N(—$CH_3$)—;
each $R^2$ is independently selected from $C_{1-10}$ alkanediyl, $C_{6-8}$ cycloalkanediyl, $C_{6-14}$ alkanecycloalkanediyl, and -[(—$CHR^3$—)$_p$—X—]$_q$—(—$CHR^3$—)$_r$—, wherein p, q, r, $R^3$, and X are as defined as for $R^1$;
m is an integer from 0 to 50;
n is an integer from 1 to 60; and
B represents a core of a z-valent, polyfunctionalizing agent B(—V)$_z$ wherein,
z is an integer from 3 to 6; and
each V is a moiety comprising a terminal group reactive with a thiol; and
each —V'— is derived from the reaction of —V with a thiol.

In prepolymers Formula (7a) and Formula (7b), $R^1$ can be -[(—$CH_2$—)$_p$—X—]$_q$—($CH_2$)$_r$—, where p can be 2, X can be —O—, q can be 2, r can be 2, $R^2$ is ethanediyl, m can be 2, and n can be 9.

In prepolymers of Formula (7a) and Formula (7b), $R^1$ can be selected from $C_{2-6}$ alkanediyl and -[(—$CHR^3$)$_p$—X—]$_q$—($CHR^3$)$_r$—.

In prepolymers of Formula (7a) and Formula (7b), $R^1$ can be -[(—$CHR^3$)$_p$—X—]$_q$—($CHR^3$)$_r$—, and X can be —O— or X can be —S—.

In prepolymers of Formula (7a) and Formula (7b), $R^1$ can be -[(—$CHR^3$)$_p$—X—]$_q$—($CHR^3$)$_r$—, where p can be 2, r can be 2, q can be 1, and X can be —S—; or where p can be 2, q can be 2, r can be 2, and X can be —O—; or where p can be 2, r can be 2, q can be 1, and X can be —O—.

In prepolymers of Formula (7a) and Formula (7b), $R^1$ can be -[(—$CHR^3$)$_p$—X—]$_q$—($CHR^3$)$_r$—, where each $R^3$ can be hydrogen, or at least one $R^3$ can be methyl.

In prepolymers of Formula (7a) and Formula (7b), each $R^1$ can be the same or at least one $R^1$ is different.

In prepolymers of Formula (7a) and Formula (7b), each $R^2$ can be $C_{2-6}$ alkanediyl, ethanediyl, 1,3-propanediyl, 1,4-butanediyl, 1,5-pentanediyl, or 1,6-hexanediyl.

Various methods can be used to prepare thiol-terminated polythioether prepolymers of Formula (7a) and Formula (7b). Examples of suitable thiol-terminated polythioether prepolymers, and methods for their production, are described, for example, in U.S. Pat. No. 6,172,179, which is incorporated by reference in its entirety. Such thiol-terminated polythioether prepolymers may be difunctional, that is, linear prepolymers having two terminal thiol groups, or polyfunctional, that is, branched prepolymers have three or more terminal thiol groups.

A thiol-terminated polythioether prepolymer can be prepared by reacting a polythiol and a diene such as a divinyl ether, and the respective amounts of the reactants used to prepare the thiol-terminated polythioether prepolymers can be chosen to yield terminal thiol groups. Thus, in some cases, (n or >n, such as n+1) moles of a polythiol, such as a dithiol or a mixture of at least two different dithiols and about 0.05 moles to 1 moles, such as 0.1 moles to 0.8 moles, of a polyfunctionalizing agent may be reacted with (n) moles of a diene, such as a divinyl ether, or a mixture of at least two different dienes, such as at least two different divinyl ethers. A polyfunctionalizing agent can be present in the reaction mixture in an amount sufficient to provide a thiol-terminated polythioether prepolymer having an average thiol functionality of from 2.05 to 3, such as from 2.1 to 2.8.

The reaction used to prepare a thiol-terminated polythioether prepolymer may be catalyzed by a free radical catalyst. Suitable free radical catalysts include azo compounds, for example azobisnitrile compounds such as azo(bis)isobutyronitrile (AIBN); organic peroxides, such as benzoyl peroxide and tert-butyl peroxide; and inorganic peroxides, such as hydrogen peroxide. The reaction can also be effected by irradiation with ultraviolet light either with or without a radical initiator/photosensitizer. Ionic catalysis methods, using either inorganic or organic bases, e.g., triethylamine, may also be used.

Suitable thiol-terminated polythioether prepolymers may be produced by reacting a divinyl ether or mixture of divinyl ethers with an excess of dithiol or a mixture of dithiols. Thus, a thiol-terminated polythioether prepolymer comprises the reaction product of reactants comprising:
(a) a dithiol of Formula (8):

(8)

wherein,
$R^1$ is selected from $C_{2-6}$ alkanediyl, $C_{6-8}$ cycloalkanediyl, $C_{6-10}$ alkanecycloalkanediyl, $C_{5-8}$ heterocycloalkanediyl, and -[(—$CHR^3$)$_p$—X—]$_q$—($CHR^3$)$_r$—;
wherein,
each $R^3$ is independently selected from hydrogen and methyl;
each X is independently selected from —O—, —S—, —NH—, and —N(—$CH_3$)—;
p is an integer from 2 to 6;
q is an integer from 1 to 5; and
r is an integer from 2 to 10; and
(b) a divinyl ether of Formula (9):

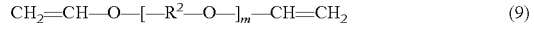

(9)

wherein,
each $R^2$ is independently selected from $C_{1-10}$ alkanediyl, $C_{6-8}$ cycloalkanediyl, $C_{6-14}$ alkanecycloalkanediyl, and -[(—$CHR^3$—)$_p$—X—]$_q$—(—$CHR^3$—)$_r$—, wherein p, q, r, $R^3$, and X are as defined above;
m is an integer from 0 to 50; and
n is an integer from 1 to 60.

The reactants used to prepare a thiol-terminated polythioether prepolymer may also comprise (c) a polyfunctional compound such as a polyfunctional compound B(—V)$_z$, where B, —V, and z are defined herein.

Dithiols suitable for use in preparing thiol-terminated polythioethers include those of Formula (8), other dithiols disclosed herein, or combinations of any of the dithiols disclosed herein. A dithiol can have the structure of Formula (8):

$$HS—R^1—SH \quad (8)$$

wherein,
$R^1$ is selected from $C_{2-6}$ alkanediyl, $C_{6-8}$ cycloalkanediyl, $C_{6-10}$ alkanecycloalkanediyl, $C_{5-8}$ heterocycloalkanediyl, and -[—(CHR$^3$)$_p$—X—]$_q$—(CHR$^3$)$_r$—; wherein,
each $R^3$ is independently selected from hydrogen and methyl;
each X is independently selected from —O—, —S—, —NH—, and —N(—CH$_3$)—;
p is an integer from 2 to 6;
q is an integer from 1 to 5; and
r is an integer from 2 to 10.

In dithiols of Formula (8), $R^1$ can be -[—(CHR$^3$)$_p$—X—]$_q$—(CHR$^3$)$_r$—.

In dithiols of Formula (8), X can selected from —O— and —S—, and thus -[—(CHR$^3$)$_p$—X—]$_q$—(CHR$^3$)$_r$— in Formula (8) can be -[(—CHR$^3$—)$_p$—O—], —(CHR$^3$)$_r$— or -[(—CHR$^3$—)$_p$—S—]$_q$—(CHR$^3$)$_r$—. In dithiols of Formula (8), p and r can be equal, such as where p and r are both two.

In dithiols of Formula (8), $R^1$ can be selected from $C_{2-6}$ alkanediyl and -[—(CHR$^3$)$_p$—X—]$_q$—(CHR$^3$)$_r$—.

In dithiols of Formula (8), $R^1$ can be -[—(CHR$^3$)$_p$—X—]$_q$—(CHR$^3$)$_r$— where X can be —O— or X can be —S—.

In dithiols of Formula (8), $R^1$ can be -[—(CHR$^3$)$_p$—X—]$_q$—(CHR$^3$)$_r$—, where p can be 2, r can be 2, q can be 1, and X can be —S—; or where p can be 2, q can be 2, r can be 2, and X can be —O—; or where p can be 2, r is 2, q can be 1, and X can be —O—.

In dithiols of Formula (8), $R^1$ can be -[—(CHR$^3$)$_p$—X—]$_q$—(CHR$^3$)$_r$— where each $R^3$ can be hydrogen or at least one $R^3$ can be methyl.

In dithiols of Formula (8), each $R^1$ can be derived from dimercaptodioxaoctane (DMDO) or each $R^1$ can be derived from dimercaptodiethylsulfide (DMDS).

In dithiols of Formula (8), each m can be independently an integer from 1 to 3. In polythiols of Formula (8) each m can be the same and is 1, 2, or 3.

In dithiols of Formula (8), n can be an integer from 1 to 30, an integer from 1 to 20, an integer from 1 to 10, or an integer from 1 to 5. In addition, n may be any integer from 1 to 60.

In dithiols of Formula (8), each p can be independently selected from 2, 3, 4, 5, and 6. In dithiols of Formula (8), each p can be the same and is 2, 3, 4, 5, or 6.

Examples of suitable dithiols include, 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol (ECHDT), dimercaptodiethylsulfide, methyl-substituted dimercaptodiethylsulfide, dimethyl-substituted dimercaptodiethylsulfide, dimercaptodioxaoctane, 1,5-dimercapto-3-oxapentane, and a combination of any of the foregoing. A dithiol may have one or more pendent groups selected from a lower (e.g., $C_{1-6}$) alkyl group, a lower alkoxy group, and/or a hydroxyl group. Suitable alkyl pendent groups include, for example, $C_{1-6}$ linear alkyl, $C_{3-6}$ branched alkyl, cyclopentyl, and cyclohexyl.

Other examples of suitable dithiols include dimercaptodiethylsulfide (DMDS) (in Formula (8), $R^1$ is -[(—CH$_2$—)$_p$—X—]$_q$—(CH$_2$)$_r$—, where p is 2, r is 2, q is 1, and X is —S—); dimercaptodioxaoctane (DMDO) (in Formula (8), $R^1$ is [(—CH$_2$—)$_p$—X—]$_q$—(CH$_2$)$_r$—, wherein p is 2, q is 2, r is 2, and X is —O—); and 1,5-dimercapto-3-oxapentane (in Formula (8), $R^1$ is [(—CH$_2$—)$_p$—X-]$_q$—(CH$_2$)$_r$—, wherein p is 2, r is 2, q is 1, and X is —O—). It is also possible to use dithiols that include both heteroatoms in the carbon backbone and pendent alkyl groups, such as methyl groups. Such compounds include, for example, methyl-substituted DMDS, such as HS—CH$_2$CH(CH$_3$)—S—CH$_2$CH$_2$—SH, HS—CH(CH$_3$)CH$_2$—S—CH$_2$CH$_2$—SH and dimethyl substituted DMDS, such as HS—CH$_2$CH(CH$_3$)—S—CHCH$_3$CH$_2$—SH and HS—CH(CH$_3$)CH$_2$—S—CH$_2$CH(CH$_3$)—SH.

Suitable divinyl ethers for preparing polythioether prepolymers include, for example, divinyl ethers of Formula (9):

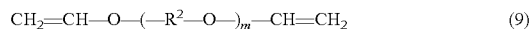

$$CH_2=CH—O—(—R^2—O—)_m—CH=CH_2 \quad (9)$$

where $R^2$ in Formula (9) is selected from a $C_2$-6 n-alkanediyl group, a $C_{3-6}$ branched alkanediyl group, a $C_{6-8}$ cycloalkanediyl group, a $C_{6-10}$ alkanecycloalkanediyl group, and -[(—CH$_2$—)$_p$—O—]$_q$—(—CH$_2$—)$_r$—, where p is an integer ranging from 2 to 6, q is an integer from 1 to 5, and r is an integer from 2 to 10. In p a divinyl ether of Formula (9), $R^2$ can be a $C_2$-6 n-alkanediyl group, a $C_{3-6}$ branched alkanediyl group, a $C_{6-8}$ cycloalkanediyl group, a $C_{6-10}$ alkanecycloalkanediyl group, or -[(—CH$_2$—)$_p$—O—]$_q$—(—CH$_2$—)$_r$—.

Suitable divinyl ethers include, for example, compounds having at least one oxyalkanediyl group, such as from 1 to 4 oxyalkanediyl groups, i.e., compounds in which m in Formula (9) is an integer from 1 to 4. In divinyl ethers of Formula (9), m can be an integer from 2 to 4. It is possible to employ commercially available divinyl ether mixtures that are characterized by a non-integral average value for the number of oxyalkanediyl units per molecule. Thus, m in Formula (9) can also take on rational number values from 0 to 10.0, such as from 1.0 to 10.0, from 1.0 to 4.0, or from 2.0 to 4.0.

Examples of suitable vinyl ethers include, divinyl ether, ethylene glycol divinyl ether (EG-DVE) ($R^2$ in Formula (9) is ethanediyl and m is 1), butanediol divinyl ether (BD-DVE) ($R^2$ in Formula (9) is butanediyl and m is 1), hexanediol divinyl ether (HD-DVE) ($R^2$ in Formula (9) is hexanediyl and m is 1), diethylene glycol divinyl ether (DEG-DVE) ($R^2$ in Formula (9) is ethanediyl and m is 2), triethylene glycol divinyl ether (TEG-DVE) ($R^2$ in Formula (9) is ethanediyl and m is 3), tetraethylene glycol divinyl ether ($R^2$ in Formula (9) is ethanediyl and m is 4), cyclohexanedimethanol divinyl ether, polytetrahydrofuryl divinyl ether; trivinyl ether monomers, such as trimethylolpropane trivinyl ether; tetrafunctional ether monomers, such as pentaerythritol tetravinyl ether; and combinations of two or more such polyvinyl ether monomers. A polyvinyl ether may have one or more pendent groups selected from alkyl groups, hydroxyl groups, alkoxy groups, and amine groups.

Divinyl ethers in which $R^2$ in Formula (9) is $C_{3-6}$ branched alkanediyl may be prepared by reacting a polyhydroxy compound with acetylene. Examples of divinyl ethers of this type include compounds in which $R^2$ in Formula (9) is an alkyl-substituted methanediyl group such as —CH(—CH$_3$)—, for which $R^2$ in Formula (9) is ethanediyl and m is 3 or an alkyl-substituted ethanediyl.

Other useful divinyl ethers include compounds in which $R^2$ in Formula (9) is polytetrahydrofuryl (poly-THF) or polyoxyalkanediyl, such as those having an average of about 3 monomer units.

Two or more types of polyvinyl ether monomers of Formula (9) may be used. Thus, two dithiols of Formula (8) and one polyvinyl ether monomer of Formula (9), one dithiol of Formula (8) and two polyvinyl ether monomers of Formula (9), two dithiols of Formula (8) and two divinyl ether monomers of Formula (9), and more than two compounds of one or both Formula (8) and Formula (9), may be used to produce a variety of thiol-terminated polythioether prepolymers.

A polyvinyl ether monomer may comprise from 20 mole percent to less than 50 mole percent of the reactants used to prepare a thiol-terminated polythioether prepolymers, such as from 30 mole percent to less than 50 mole percent.

In the reaction, relative amounts of dithiols and divinyl ethers can be selected to yield polythioether prepolymers having terminal thiol groups. Thus, a dithiol of Formula (8) or a mixture of at least two different dithiols of Formula (8), can be reacted with of a divinyl ether of Formula (9) or a mixture of at least two different divinyl ethers of Formula (9) in relative amounts such that the molar ratio of thiol groups to alkenyl groups is greater than 1:1, such as from 1.1 to 2.0:1.0.

The reaction between dithiols and divinyl ethers and/or polythiols and polyvinyl ethers may be catalyzed by a free radical catalyst. Suitable free radical catalysts include, for example, azo compounds, for example azobisnitriles such as azo(bis)isobutyronitrile (AIBN); organic peroxides such as benzoyl peroxide and t-butyl peroxide; and inorganic peroxides such as hydrogen peroxide. The catalyst may be a free-radical catalyst, an ionic catalyst, or ultraviolet radiation. In certain embodiments, a catalyst does not comprise acidic or basic compounds, and does not produce acidic or basic compounds upon decomposition. Examples of free-radical catalysts include azo-type catalyst, such as Vazo®-57 (Du Pont), Vazo®-64 (Du Pont), Vazo®-67 (Du Pont), V-70® (Wako Specialty Chemicals), and V-65B® (Wako Specialty Chemicals). Examples of other free-radical catalysts include alkyl peroxides, such as tert-butyl peroxide. The reaction may also be effected by irradiation with ultraviolet light either with or without a cationic photoinitiating moiety.

Thiol-terminated polythioether prepolymers may be prepared by combining at least one dithiol of Formula (8) and at least one divinyl ether of Formula (9) followed by addition of an appropriate catalyst, and carrying out the reaction at a temperature from 30° C. to 120° C., such as from 70° C. to 90° C., for a time from 2 hours to 24 hours, such as from 2 hours to 6 hours.

Thiol-terminated polythioether prepolymers may comprise a polyfunctional thiol-terminated polythioether, i.e., may have an average functionality of greater than 2.0. Suitable polyfunctional thiol-terminated polythioether prepolymers include, for example, those having the structure of Formula (7b):

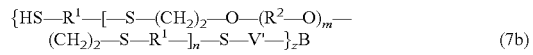 (7b)

wherein z has an average value of greater than 2.0, a value between 2 and 3, a value between 2 and 4, a value between 3 and 6, or can be an integer from 3 to 6.

Polyfunctionalizing agents suitable for use in preparing such polyfunctional thiol-terminated prepolymers include trifunctionalizing agents, that is, compounds where z is 3. Suitable trifunctionalizing agents include, for example, triallyl cyanurate (TAC), 1,2,3-propanetrithiol, isocyanurate-containing trithiols such as 1,3,5-tris(2-mercpatoethyl)[1,3,5]-triazine-2,4,6-trione (METT), and combinations thereof, as disclosed in U.S. Application Publication No. 2010/0010133, which is incorporated by reference in its entirety, and isocyanurates as disclosed, for example, in U.S. Application Publication No. 2011/0319559, which is incorporated by reference in its entirety. Other useful polyfunctionalizing agents include trimethylolpropane trivinyl ether, and the polythiols described in U.S. Pat. Nos. 4,366,307; 4,609,762; and 5,225,472, each of which is incorporated by reference in its entirety. Mixtures of polyfunctionalizing agents may also be used. As a result, thiol-terminated polythioethers may have a wide range of average functionality. For example, trifunctionalizing agents may afford average functionalities from 2.05 to 3.0, such as from 2.1 to 2.6, or from 2.05 to 2.8. Wider ranges of average functionality may be achieved by using tetrafunctional or higher functionality polyfunctionalizing agents. Functionality may also be determined by factors such as stoichiometry, as will be understood by those skilled in the art.

A thiol-terminated sulfur-containing prepolymer can comprise a thiol-terminated sulfur-containing polyformal prepolymer.

Thiol-terminated sulfur-containing polyformal prepolymers useful in aerospace sealant applications are disclosed, for example, in U.S. Application Publication No. 2012/0234205 and in U.S. Application Publication No. 2012/0238707, each of which is incorporated by reference in its entirety.

A thiol-terminated sulfur-containing polyformal prepolymer can comprise the reaction products of reactants comprising (a) and (b), where (a) comprises the reaction products of reactants comprising (i) and (ii), where (i) comprises a sulfur-containing polyformal of Formula (11):

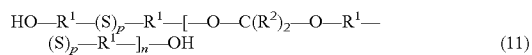 (11)

where n is an integer selected from 1 to 50; each p is independently selected from 1 and 2; each $R^1$ is independently selected from $C_{2-6}$ alkanediyl; and each $R^2$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and (ii) comprises a first compound selected from a diisocyanate, thiourea, an ethylenically unsaturated isocyanate, and a tosylate; and (b) a compound comprising a terminal thiol group; and (b) comprises a mercaptoalkanol when (ii) comprises a diisocyanate; (b) comprises a metal hydrosulfide when (ii) comprises thiourea; (b) comprises a dithiol when (ii) comprises an ethylenically unsaturated isocyanate; and (b) comprises a metal hydrosulfide when (ii) comprises a tosylate.

In a reaction to form a thiol-terminated sulfur-containing polyformal prepolymer, the compound can comprise a terminal thiol group selected from a dithiol and an alkyl(bis) oxydialkanethiol. Examples of suitable dithiols include compounds of the formula HS—R—SH where R is a $C_{2-6}$ alkanediyl, having one or more pendent groups, which can be, for example, hydroxyl groups, $C_{1-6}$ alkyl groups such as methyl or ethyl groups; $C_{1-6}$ alkoxy, $C_{6-8}$ cycloalkanediyl, $C_{6-10}$ alkanecycloalkanediyl, -[—(CH$_2$)$_p$—X—]$_q$—(CH$_2$)$_r$—, or -[—(CH$_2$)$_p$—X—]$_q$—(CH$_2$)$_r$— in which at least one —CH$_2$— unit is substituted with a methyl group and in which each p is independently selected from an integer selected from 2 to 6, each q is independently selected from an integer selected from 1 to 5, and each r is independently selected from an integer selected from 2 to 10. Dithiols may include one or more heteroatom substituents in the carbon backbone, for example, dithiols in which X includes a heteroatom such as O, S or other bivalent heteroatom radical, a secondary or tertiary amine group such as —NR'—, where R' is hydrogen or methyl, or another substituted trivalent heteroatom. X can be O or S, p and r can be equal, or both p and r can be 2. X can be a bond. Examples of suitable dithiols include 1,2-ethanedithiol, 1,2-propanedithiol, 1,3-propanedithiol, 1,3-butanedithiol, 1,4-butanedithiol, 2,3-butanedithiol, 1,3-pentanedithiol, 1,5-pentanedithiol, 1,6-hexanedithiol, 1,3-dimercapto-3-methylbutane, dipentenedimercaptan, ethylcyclohexyldithiol, dimercaptodiethylsulfide, methyl-substituted dimercaptodiethylsulfide, dimethyl-substituted dimercaptodiethylsulfide, dimethyl-substituted dimercaptodiethylsulfide, dimercaptodioxaoctane, and 1,5-dimercapto-3-oxapentane. A dithiol may have one or more pendent groups selected from $C_{1-4}$ alkyl, $C_{1-4}$ alkoxy, and hydroxyl. Additional examples of suitable mercaptoalkanols include, for example, $C_{2-6}$ mercaptoalkanols such as 2-mercaptoethan-1-ol, 3-mercaptopropan-1-ol, 4-mercaptobutan-1-ol, 5-mercaptopentan-1-ol, and 6-mercaptohexan-1-ol. Examples of suitable dithiols include, for example, $C_{2-10}$ alkanedithiols such as ethane-1,2-dithiol, propane-1,3-dithiol, butane-1,4-dithiol, pentane-1,5-dithiol, and hexane-1,6-dithiol.

A dithiol can be an alkyl(bis)oxydialkane. Alkyl(bis) oxydialkane thiols may have the general formula HS—R—O—R'—O—R—HS, where each R and R' is an alkanediyl such as, for example, $C_{2-6}$ alkanediyl, $C_{2-4}$ alkanediyl, or $C_2$ alkanediyl. A dithiol can be selected from dimercaptodiethylsulfide (DMDS), 1,8-dimercapto-3,6-dioxaoctane (DMDO), and 1,5-dimercapto-3-oxapentane.

An example of a metal hydrosulfide is sodium hydrosulfide. An example of a tosylate is a sulfonyl chloride such as p-toluenesulfonyl chloride.

In the above terminal-modified sulfur-containing polyformal prepolymers, the terminal-modified sulfur-containing polyformal can be characterized by a number average molecular weight within a range from 200 Daltons to 6,000 Daltons, from 500 Daltons to 5,000 Daltons, from 1,000 Daltons to 5,000 Daltons, from 1,500 Daltons to 4,000 Daltons, or from 2,000 to 3,600 Daltons.

Terminal-modified sulfur-containing polyformal prepolymers provided by the present disclosure can have the structure of Formula (12):

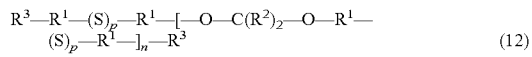

where n is an integer selected from 1 to 50; each p is independently selected from 1 and 2; each $R^1$ is independently selected from $C_{2-6}$ alkanediyl; each $R^2$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and each $R^3$ is —$OR^{3'}$ wherein $R^{3'}$ is selected from a vinyl-terminated group, a silyl-terminated group, an amine-terminated group, an epoxy-terminated group, and a thiol-terminated group.

In a sulfur-containing polyformal of Formula (12), each $R^1$ can be independently selected from $C_{2-6}$ alkanediyl, $C_{2-4}$ alkanediyl, $C_{2-3}$ alkanediyl, or ethane-1,2-diyl. In a polyformal of Formula (12), each $R^1$ can be ethane-1,2-diyl.

In a sulfur-containing polyformal of Formula (12), each $R^2$ can be independently selected from hydrogen, $C_{1-6}$ alkyl, $C_{1-4}$ alkyl, $C_{1-3}$ alkyl, or $C_{1-2}$ alkyl. In a polyformal of Formula (12), each $R^2$ can be hydrogen, methyl, or ethyl.

In a sulfur-containing polyformal of Formula (12), each $R^1$ can be the same and can be selected from a $C_{2-3}$ alkanediyl such as ethane-1,2-diyl and propane-1,3-diyl; or each $R^2$ can be the same and can be selected from hydrogen and $C_{1-3}$ alkyl such as methyl, ethyl, and propyl. In a sulfur-containing polyformal of Formula (12), each $R^1$ can be ethane-1,2-diyl. In a sulfur-containing polyformal of Formula (12), each $R^2$ can be hydrogen. In a sulfur-containing polyformal of Formula (12), each $R^1$ can be ethane-1,2-diyl and each $R^2$ can be hydrogen.

In a sulfur-containing polyformal of Formula (12), n can be an integer selected from 1 to 50, an integer selected from 2 to 40, an integer selected from 4 to 30, or n can be an integer selected from 7 to 30.

In a sulfur-containing polyformal of Formula (12), each p can be the same and can be 1, or each p is the same and can be 2.

A sulfur-containing polyformal of Formula (12) can have a number average molecular weight within a range from 200 Daltons to 6,000 Daltons, from 500 Daltons to 5,000 Daltons, from 1,000 Daltons to 5,000 Daltons, from 1,500 to 4000 Daltons, or from 2,000 to 3,600 Daltons.

In a polyformal of Formula (12), each $R^3$ can be the same.

In a polyformal of Formula (12), each $R^3$ can be a thiol-terminated group and is independently selected from a group of Formula (a), Formula (b), Formula (c), Formula (d), Formula (e), Formula (f), Formula (g), and Formula (h):

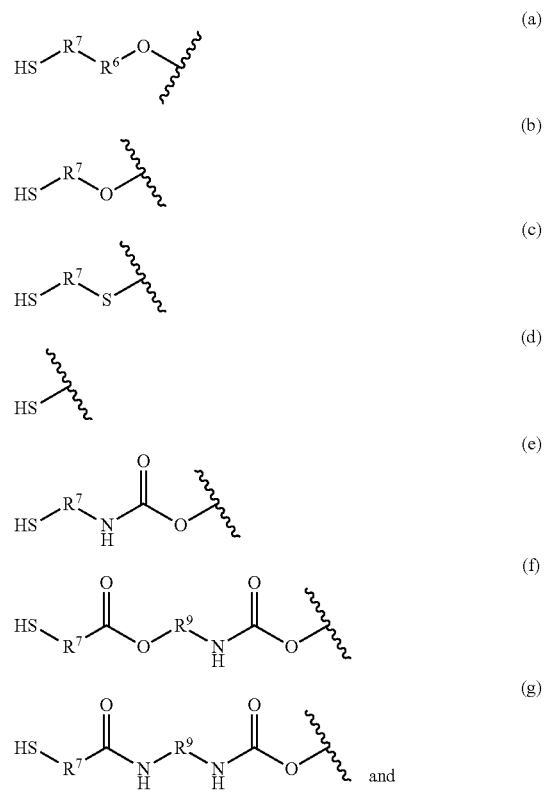

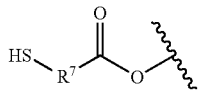
(h)

where each $R^6$ is selected from a moiety derived from a diisocyanate and a moiety derived from an ethylenically unsaturated monoisocyanate; each $R^7$ is selected from $C_{2-14}$ alkanediyl and $C_{2-14}$ heteroalkanediyl; and each $R^9$ is selected from $C_{2-6}$ alkanediyl, $C_{2-6}$ heteroalkanediyl, $C_{6-12}$ arenediyl, substituted $C_{6-12}$ arenediyl, $C_{6-12}$ heteroarenediyl, substituted $C_{6-12}$ heteroarenediyl, $C_{3-12}$ cycloalkanediyl, substituted $C_{3-12}$ cycloalkanediyl, $C_{3-12}$ heterocycloalkanediyl, substituted $C_{3-12}$ heterocycloalkanediyl, $C_{7-18}$ alkanearenediyl, substituted $C_{7-18}$ heteroalkanearenediyl, $C_{4-18}$ alkanecycloalkanediyl, and substituted $C_{4-18}$ alkanecycloalkanediyl.

In a moiety of Formula (a), each $R^6$ can be a group derived from a diisocyanate, and the group can derived from TDI, ISONATE™ 143L (polycarbodiimide-modified diphenylmethane diisocyanate), DESMODUR® N3400 (1,3-diazetidine-2,4-dione, 1,3-bis(6-isocyanatohexyl)-), DESMODUR® I (isophorone diisocyanate, IPDI), or DESMODUR® W ($H_{12}$MDI).

In a moiety of Formula (a), each $R^6$ can be a group derived from an ethylenically unsaturated monoisocyanate, or 2-isocyanatoethyl methacrylate.

In a moiety of Formula (a), Formula (b), Formula (c), Formula (e), Formula (f), Formula (g), and Formula (h), each $R^7$ can be selected from $C_{2-6}$ alkanediyl. In a moiety of Formula (a), Formula (b), Formula (c), Formula (e), Formula (f), Formula (g), and Formula (h), each $R^7$ can be selected from —$CH_2$—S—$(CH_2)_2$—O—$(CH_2)_2$—O—$(CH_2)_2$—, —$(CH_2)_2$—O—$(CH_2)_2$—O—$(CH_2)_2$—, or —$(CH_2)_2$—S—$(CH_2)_2$—O—$(CH_2)_2$—O—$(CH_2)_2$—.

In a moiety of Formula (f) and Formula (g), each $R^9$ can be selected from $C_{2-6}$ alkanediyl, $C_{6-12}$ arenediyl, substituted $C_{6-12}$ arenediyl, $C_{3-12}$ cycloalkanediyl, substituted $C_{3-12}$ cycloalkanediyl, $C_{7-18}$ alkanearenediyl, substituted $C_{7-18}$ alkanearenediyl, $C_{4-18}$ alkanecycloalkanediyl, or substituted $C_{4-18}$ alkanecycloalkanediyl.

A thiol-terminated sulfur-containing polyformal provided by the present disclosure can comprise a thiol-terminated sulfur-containing polyformal of Formula (13a), a thiol-terminated sulfur-containing polyformal of Formula (13b), or a combination thereof:

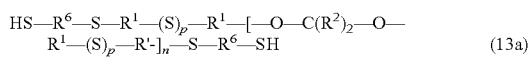 (13a)

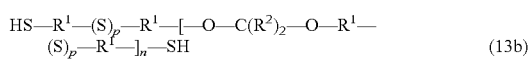 (13b)

where n is an integer selected from 1 to 50; each p is independently selected from 1 and 2; each $R^1$ is independently selected from $C_{2-6}$ alkanediyl; each $R^2$ is independently selected from hydrogen, $C_{1-6}$ alkyl, $C_{7-12}$ phenylalkyl, substituted $C_{7-12}$ phenylalkyl, $C_{6-12}$ cycloalkylalkyl, substituted $C_{6-12}$ cycloalkylalkyl, $C_{3-12}$ cycloalkyl, substituted $C_{3-12}$ cycloalkyl, $C_{6-12}$ aryl, and substituted $C_{6-12}$ aryl; and each $R^6$ is independently selected from $C_{2-6}$ alkanediyl and $C_{5-12}$ heteroalkanediyl. In a polyformal of Formula (13a) and Formula (13b), each p can be 1 or each p is 2. In a polyformal of Formula (13a) and Formula (13b), each $R^1$ may be the same or each $R^1$ may be different. In a polyformal of Formula (13a) and (13b), each $R^1$ can be $C_{2-5}$ alkanediyl, $C_{2-4}$ alkanediyl, propane-1,3-diyl, propane-1,2-diyl, or ethane-1,2-diyl. In a polyformal of Formula (13a) and Formula (13b), each $R^1$ can be the same and can be selected from ethane-1,2-diyl or propane-1,3-diyl, and each $R^2$ can be the same and can be selected from hydrogen, methyl, or ethyl. In a polyformal of Formula (13a), each $R^6$ can be the same and is selected from ethane-1,2-diyl and propane-1,3-diyl. In a polyformal of Formula (13a) and Formula (13b), n can be an integer selected from 5 to 40 or an integer selected from 10 to 40.

Thiol-terminated sulfur-containing polyformals of Formula (13a) may be prepared by reacting a vinyl-terminated sulfur-containing polyformal such as the 2-isocyanatoethyl methacrylate adduct or the allyl isocyanate adduct as disclosed herein with a dithiol such as DMDO. Thiol-terminated sulfur-containing polyformals of Formula (13a) may also be prepared by reacting a tosyl-ester of a sulfur-containing polyformal of Formula (11) with NaSH in the presence of MeN(Bu)$^{3+}$Cl$^-$ in water to provide the corresponding thiol-terminated sulfur-containing polyformal of Formula (13). Alternatively, a tosyl-ester of a sulfur-containing polyformal of Formula (11) may be reacted with thiourea in the presence of MeN(Bu)$^{3+}$Cl$^-$ in water to provide the tosylate salt of the thiourea adduct, which may then be reacted in the presence of base at elevated temperature to provide the corresponding thiol-terminated sulfur-containing polyformal of Formula (13). Alternatively, to obtain thiol-terminated sulfur-containing polyformals of Formula (13), a sulfur-containing polyformal of Formula (11) may first be reacted with a diisocyanate such as TDI in the presence of dibutyltin dilaurate at 75° C. to 80° C. to provide the corresponding isocyanate-terminated sulfur-containing polyformal of Formula (13). The isocyanate-terminated sulfur-containing polyformal of Formula (13) may then be reacted with a mercaptoalkanol such as 2-mercaptoethanol or 3-mercaptopropanol to provide the corresponding thiol-terminated sulfur-containing polyformal of Formula (13).

A thiol-terminated sulfur-containing prepolymer can comprise a metal ligand-containing thiol-terminated sulfur-containing prepolymer in which a metal ligand is incorporated into the backbone of the prepolymer. Examples of metal ligand-containing sulfur-containing prepolymers are disclosed in U.S. Application Publication Nos. 2014/0275474, 2014/0378649, and 2014/0378650, each of which is incorporated by reference in its entirety.

Compositions provided by the present disclosure can comprise an ionic liquid catalyst or a primary catalyst and an ionic liquid co-catalyst. The ionic liquid catalyst or co-catalyst can comprise an ionic liquid, a polymeric ionic liquid, or a combination thereof. An ionic liquid catalyst or co-catalyst can be an encapsulated ionic liquid catalyst or co-catalyst. When used as a catalyst, the ionic liquid is the only catalyst in the sealant composition. When used as a co-catalyst, an ionic liquid can be combined with a primary catalyst and the ionic liquid is referred to as a co-catalyst. By using an ionic liquid co-catalyst the amount of the primary catalyst can be reduced compared to a similar composition without the ionic liquid co-catalyst.

Compositions provided by the present disclosure can include one or more ionic liquid catalysts or co-catalysts. The ionic liquid catalyst may be the only catalyst in a composition or may be used as a co-catalyst combined with one or more additional co-catalysts, which can be referred to as a primary catalyst. When used as a co-catalyst, an ionic liquid catalyst may reduce the amount of the primary used. This is especially useful when the other co-catalyst has detrimental effects on the cured sealant.

An ionic liquid catalyst refers to an ionic liquid, which is used as a catalyst. Therefore, the expression "ionic liquid catalyst" and "ionic liquid" refer to the same compounds and the expressions may be used interchangeably.

Ionic liquids are salts that are liquid at temperatures less than or equal to 400° C., such as at temperatures less than 100° C. Examples of suitable ionic liquids include combinations of cations and/or anions. Suitable cations can include, for example, mono-, di-, and tri-substituted imidazoliums; substituted pyridiniums; substituted pyrrolidiniums; tetraalkyl phosphoniums; tetraalkyl ammoniums; guanidiniums; isouroniums; and thiouroniums. Suitable anions can include, for example, chlorides; bromides; iodides; tetrafluoroborates; hexafluorophosphates; bis(trifluoromethylsulfonyl)imides; tris(pentafluoroethyl)trifluorophosphates (FAPs); trifluoromethanesulfonates; trifluoroacetates; methylsulfates; octylsulfates; thiocyanates; organoborates; and p-toluenesulfonates. Examples of ionic liquids include 1-butyl-3-methylimidazolium hexafluorophosphate ([BMIM] $PF_6$), 1-hexyl-3-methylimidazolium tetrafluoroborate ([HMIM] $BF_4$), 1-butyl-3-methylimidazolium tetrafluoroborate ([BMIM] $BF_4$), and 1-ethyl-3-methylimidazolium trifluoromethane sulfonamide ([EMIM] $(CF_3SO_2)_2N$). Suitable ionic liquids are commercially available, for example, from Solvent Innovation GmbH, BASF, or from Merck KGaA. Variations in cations and anions can produce ionic liquids adapted for specific applications.

Ionic liquid catalysts can include low melting temperature organic salts that are liquid at temperatures less than 100° C., have a low vapor pressure, and a high thermal stability, and can include those formed by a combination of an organic cation, and an organic or inorganic cation. Examples of suitable organic cations include imidazolium, pyridinium, pyrrolidinium, phosphonium ($P^+$(—$R)_4$), ammonium ($N^+$(—$R)_4$) and sulfonium ($S^-$(—$R)_3$) cations. Examples of suitable organic anions include alkylsulfate, tosylate, and methand anesulfonate anions. Examples of suitable inorganic anions include $C(F_3)$—$S(O)_2$—$N^-$—$S(O)_2$—$C(F_3)$, $PF_6^-$, $BF_4^-$.

Other examples of suitable ionic liquids include 1-ethyl-3-methylimidazolium chloride, 1-ethyl-3-methylimidazolium methanesulfonate, 1-butyl-3-methylimidazolium chloride, 1-butyl-3-methylimidazolium methane sulfonate, methyl-tri-n-butylammonium methyl sulfate, 1,2,4-trimethylpyrazolium methylsulfate, 1-ethyl-2,3-di-methylimidazolium ethylsulfate, 1,2,3-trimethylimidazolium methylsulfate, methylimidazolium chloride, methylimidazolium hydrogen sulfate, 1-ethyl-3-methylimidazolium hydrogensulfate, 1-ethyl-3-methylimidazolium tetrachloroaluminate, 1-butyl-3-methylimidazolium hydrogen sulfate, 1-butyl-3-methylimidazolium tetrachloroaluminate, 1-ethyl-3-methylimidazolium acetate, 1-butyl-3-methylimidazolium acetate, 1-ethyl-3-methylimidazolium ethylsulfate, 1-butyl-3-methylimidazolium methyl sulfate, 1-ethyl-3-methylimidazolium thiocyanate, and 1-butyl-3-methylimidazolium thiocyanate.

An ionic liquid may be an imidazolium-based ionic liquid such as 1-allyl-3-methylimidazolium chloride, 1-benzyl-3-methylimidazolium chloride, 1-benzyl-3-methylimidazolium hexafluorophosphate, 1-benzyl-3-methylimidazolium tetrafluoroborate, 1-butyl-1-(3,3,4,4,5,5,6,6,7,7,8,8,8-tridecafluorooctyl)imidazolium hexafluorophosphate, 1-butyl-2,3-dimethylimidazolium chloride, 1-butyl-2,3-dimethylimidazolium chloride, 1-butyl-2,3-dimethylimidazolium hexafluorophosphate, 1-butyl-2,3-dimethylimidazolium tetrafluoroborate, 1-butyl-3-methylimidazolium 2-(2-methoxyethoxy)-ethyl sulfate, 1-butyl-3-methylimidazolium bromide, 1-butyl-3-methylimidazolium chloride, 1-butyl-3-methylimidazolium methyl sulfate, 1-butyl-3-methylimidazolium tetrafluoroborate, 1-butyl-3-methylimidazolium trifluoromethanesulfonate, 1-butyl-2,3-diemethylimidazolium chloride, 1-ethyl-3-methylimidazolium bromide, 1-ethyl-3-methylimidazolium chloride, 1-ethyl-3-methylimidazolium hexafluorophosphate, 1-ethyl-3-methylimidazolium methyl sulfate, 1-ethyl-3-methylimidazolium trifluoromethanesulfonate, 1-hexyl-3-methylimidazolium chloride, 1-hexyl-3-methylimidazolium hexafluorophosphate, 1-hexyl-3-methylimidazolium trifluoromethane sulfonate, 1-hexyl-3-methylimidazolium trifluoromethane sulfonate, 1-methyl-3-(3,3,4,4,5,5,6,6,7,7,8,8,8-tridecafluorooctyl)imidazolium hexafluorophosphate, 1-methyl-3-ocytlimidazolium chloride, 1-methyl-3-octylimidazolium trifluoromethanesulfonate, 1-methyl-3-ocytlimidazolium trifluoromethanesulfonate, 1,2,3-trimethylimidazolium trifluoromethane sulfonate, 1-butyl-3-methylimidazolium dicyanamide, and 1-butyl-3-methylimidazolium nitrate.

Examples of suitable pyridinium-based ionic liquids include 1-butylpyridinium bromide, 1-butyl-4-methylpyridinium bromide, 1-butyl-4-methylpyridinium chloride, and 1-butyl-4-methylpyridinium hexafluorophosphate.

Examples of suitable pyrrolidinium-based ionic liquids include 1-butyl-1-methylpyrrolidinium bis(trifluoromethylsulfonyl)imide, 1-butyl-1-methylpyrrolidinium bromide, 1-butyl-4-methylpyrrolidinium chloride, and 1-butyl-4-methylpyrrolidinium hexafluorophosphate.

Examples of suitable ammonium-based ionic liquids include tetrabutylammonium benzoate, tetrabutylammonium methanesulfonate, tetrabutylammonium nonafluorobutanesulfonate, tetrabutylammonium heptadecafluorooctanesulfonate, tetrahexylammonium tetrafluoroborate, tetraoctylammonium chloride, tetrapentylammonium thiocyanate, tetrabutylammonium bromide, tetrabutylammonium bromide, tetrabutylammonium chloride, tetraethylammonim trifluoroacetate, tetraheptylammonium bromide, tetraheptylammonium chloride, tetrahexylammonium bromide, tetrahexylammonium iodide, tetraoctylammonium bromide, and tetrapentylammonium bromide.

Examples of suitable phosphonium-based ionic liquids include tetrbutylphosphonium methanesulfonate, tetrabutylphosphonium tetrafluoroborate, tetrabutylphosphonium p-toluenesulfonate, tetrabutylphosphonium bromide, tetrabutylphosphonium chloride, and tributylhexadecyl phosphonium bromide.

An ionic liquid catalyst can comprise a phosphonium ionic liquid, an imidazolium-based ionic liquid, a pyridinium-based ionic liquid, a pyrrolidinium-based ionic liquid, an ammonium-based ionic liquid, a phosphonium-based ionic liquid, a sulfonium-based ionic liquid, or a combination of any of the foregoing. An ionic liquid catalyst can comprise an imidazolium ionic liquid. Examples of suitable imidazolium-based ionic liquids include 1-ethyl-3-methylimidazolium chloride, 1-ethyl-3-methyl imidazolium methanesulfonate, 1-ethyl-3-methyl imidazolium ethylsulfate, 1-ethyl-3-methyl imidazolium dicyanamide, 1-ethyl-3-methyl imidazolium acetate, 1-ethyl-3-methyl imidazolium trifluoromethane sulfonate, 1-ethyl-3-methyl imidazolium bis(trifluororomethanesulfonyl)imide, and 1-ethyl-3-methyl imidazolium. An ionic liquid catalyst can comprise 1-butyl-3-methylimidazolium acetate, 1-ethyl-3-methylimidazolium ethyl sulfate, or a combination thereof.

The amount of ionic liquid catalyst used in a composition provided by the present disclosure can be sufficient to result in a cured sealant in an acceptable period of time. The amount of ionic liquid catalyst in a curable composition can depend at least in part on the curing chemistry, the curing temperature, the desired curing time, and whether an additional catalyst is present. A composition provided by the present disclosure can comprise less than 1 wt % of an ionic liquid co-catalyst, less than 0.1 wt %, less than 0.05 wt %, less than 0.02 wt %, or less than 0.01 wt %, where wt % is based on the total solids weight of the composition. A composition provided by the present disclosure can comprise from 0.01 wt % to 2 wt %, from 0.01 wt % to 1 wt %, from 0.1 wt % to 1 wt %, from 0.1 wt % to 0.5 wt %, or from 0.01 wt % to 0.1 wt %, of an ionic liquid co-catalyst, where wt % is based on the total solids weight of the composition.

A curable composition provided by the present disclosure can comprise less than 3 wt % of an ionic liquid co-catalyst, less than 2 wt %, less than 1 wt %, less than 0.8 wt %, less than 0.6 wt %, less than 0.4 wt %, less than 0.2 wt %, or less than 0.1 wt % of an ionic liquid co-catalyst. A curable composition can comprise from 0.05 wt % to 3 wt %, from 0.05 wt % to 2 wt %, from 0.05 wt % to 1 wt %, from 0.1 wt % to 1 wt %, or from 0.1 wt % to 0.6 wt % of an ionic liquid co-catalyst.

In curable compositions in which an ionic liquid is the only catalyst in the curable composition, the curable composition can comprise less than 15 wt %, less than 12 wt %, less than 8 wt %, less than 6 wt %, less than 4 wt % or less than 2 wt % of the ionic liquid catalyst where wt % is based on the total solids weight of the curable composition. For example, a curable composition may comprise from 1 wt % to 15 wt %, from 1 wt % to 12 wt %, from 1 wt % to 8 wt %, or from 1 wt % to 5 wt % of an ionic liquid catalyst or combination of ionic liquid catalysts, where wt % is based on the total solids weight of the curable composition.

An ionic liquid catalyst or co-catalyst may be a controlled release catalyst or co-catalyst. Use of controlled release catalysts can provide cure on demand systems.

Compositions having extended working time and a controlled curing rate can be realized by using a controlled release ionic liquid catalyst or co-catalyst. In these systems, an ionic liquid can be sequestered or encapsulated and dispersed in a sealant composition. Upon exposure to stress such as, for example, elevated temperature, the catalytic ionic liquid can be released from the encapsulant and be available to catalyze the curing reaction. When the ionic liquid catalyst or co-catalyst is released, the composition can have a useful working time from 2 hours to 12 hours and cure within 24 hours to 72 hours.

Controlled release ionic liquid catalysts have little or no activity until released, such as thermally, chemically or physically. A controlled release ionic liquid co-catalyst may be released upon exposure to heat, ultrasonication, and/or impact.

In controlled release compositions provided by the present disclosure, working time of a composition can be greater than 2 weeks if the catalyst is not released. When the catalyst is released, either by chemical, thermal, photochemical, or physical mechanisms, the cure time can be less than 72 hours, less than 60 hours, less than 48 hours, less than 36 hours, less than 24 hours, or less than 12 hours.

An ionic liquid catalyst may be incorporated into a matrix encapsulant. In matrix encapsulant systems, an ionic liquid co-catalyst is trapped among side chains of a crystalline or semi-crystalline polymer. At elevated temperature, the polymer melts allowing the ionic liquid co-catalyst to diffuse into the composition to catalyze a curing reaction.

Matrix encapsulation is a process by which droplets or particles of liquid or solid material are trapped among side chains of a crystalline polymer. With increased temperature, the crystalline polymer becomes amorphous and releases the droplets or particles into the medium. Matrix encapsulants provided by the present disclosure can comprise a crystalline matrix material incorporating droplets or particles comprising an ionic liquid co-catalyst. Thus, the rate of reaction is to some extent controlled by thermally dependent diffusion of the ionic liquid co-catalyst from the crystalline polymer. The crystalline polymers may have a sharp well-defined melting point or may exhibit a melting point range. The use of waxy polymers for encapsulation of amine catalysts used in Michael addition compositions is disclosed in U.S. Application Publication No. 2007/0173602, which is incorporated by reference in its entirety.

Examples of suitable matrix encapsulants include Intelimer® polymers (Air Products), such as Intelimer® 13-1 and Intelimer® 13-6. Properties of Intelimer® polymers is disclosed in Lowry et al., Cure evaluation of Intelimer® latent curing agents for thermoset resin applications, presented at the Thermoset Resin Formulators Association Meeting, Chicago, Ill., Sep. 15-16, 2008.

A matrix encapsulant may be selected to release an ionic liquid following a brief high temperature exposure such as for less than 10 minutes, less than 5 minutes, or less than 2 minutes. During this brief high temperature exposure, the ionic liquid catalyst can be released from the matrix and diffuses into the reactive prepolymer and curing agent components of the curable composition. The composition may be heated during the curing process or may be left at ambient temperature. When left at ambient temperature, the released ionic liquid catalyst-containing composition may cure in less than 2 hours, in less than 4 hours, or in less than 6 hours.

Ionic liquid catalysts may be incorporated into a matrix encapsulant by blending at a temperature above the melt temperature of the matrix encapsulant, rapidly cooling the mixture, and grinding the solid to a powder. The average particle size of the powder can be less than 200 µm, less than 150 µm, less than 100 µm, less than 50 µm, or less than 25 µm.

A controlled release ionic liquid catalyst can comprise an ionic liquid adsorbed onto silica, which is then incorporated into a matrix encapsulation material. Following heating, the ionic liquid can be released from the encapsulating matrix to accelerate the cure of a reaction.

A composition provided by the present disclosure may comprise, for example, from 0.1 wt % to 25 wt %, from 1 wt % to 15 wt %, or from 5 wt % to 10 wt % of a matrix encapsulant comprising an ionic liquid co-catalyst. This can correlate to about 0.01 wt % to 2 wt %, from 0.05 wt % to 1.5 wt %, or from 0.5 wt % to 1 wt % of an ionic liquid catalyst in a curable composition.

A matrix encapsulant suitable for use in compositions provided by the present disclosure can comprise a ratio (wt %/wt %) of wt % ionic liquid catalyst to wt % matrix polymer from 1 to 15, from 2 to 10, or from 5 to 8.

In addition to one or more ionic liquid co-catalysts, a curable composition provided by the present disclosure may include other catalysts, which are also referred to as primary catalysts. The selection of the one or more primary catalysts can depend in part on the curing chemistry of the composition. For example, the curing chemistry can be a manganese dioxide-catalyzed condensation of thiol-terminated sulfur-containing prepolymers, an amine-catalyzed Michael addition curing of thiol-terminated sulfur-containing prepolymers, or an amine-catalyzed reaction of polyepoxides with thiol-terminated sulfur-containing prepolymers. In oxidative reactions or in amine-catalyzed reactions, an ionic liquid can be used as a co-catalyst to reduce the amount of oxidant or amine catalyst in a composition, respectively. In certain compositions provided by the present disclosure it can be desirable to minimize the presence of the additional oxidant or amine catalyst in a cured sealant to prevent or to minimize compromising the sealant properties caused by the additional catalyst.

A primary catalyst can be an oxidizing agent capable of oxidizing terminal thiol groups to form disulfide bonds. Examples of suitable oxidizing agents include lead dioxide, manganese dioxide, calcium dioxide, sodium perborate monohydrate, calcium peroxide, zinc peroxide, dichromate and epoxy.

A primary catalyst can comprise a base catalyst such as an amine catalyst. An amine catalyst may be a primary amine catalyst, a secondary amine catalyst, or a tertiary amine catalyst. Examples of suitable primary amine catalysts include $C_{3-10}$ aliphatic primary amines, such as heptane amine, hexylamine, and octamine. Examples of suitable secondary amine catalysts include cycloaliphatic diamines such as Jefflink® 754 and aliphatic diamines such as Clearlink® 1000. Examples of suitable tertiary amine catalysts include N,N-dimethylethanolamine (DMEA), 1,4-diazabicyclo[2.2.2]octane (DABCO), triethylene diamine (TEDA), bis(2-dimethylaminoethyl)ether (BDMAEE), N-ethylmorpholine, N',N'-dimethylpiperazine, N,N,N',N',N'''-pentamethyl-diethylene-triamine (PMDETA), N,N'-dimethylcyclohexylamine (DMCHA), N,N-dimethylbenzylamine (DMBA), N,N-dimethylcethylamine, N,N,N',N'',N''-pentamethyl-dipropylene-triamine (PMDPTA), triethylamine, and 1-(2-hydroxypropyl) imidazole. Other suitable amine catalysts include amidine catalysts such as tetramethylguanidine (TMG), diazabicyclononene (DBN), 1,8-diazabicyclo[5.4.0]undec-7-ene (DBU) and imidazoles; and bicyclic guanidines such as 1,5,7,-triazabicyclo[4.4.0]dec-5-ene (TBD), and 1,5,7,-triazabicyclo[4.4.0]dec-5-ene, 7-methyl (MTBD).

An amine catalyst can comprise DBU, DABCO, isophorone diamine (IPDA), a $C_{6-10}$ primary amine, or a combination of any of the foregoing.

Compositions may comprise one or more different types of oxidizing agents or amine catalysts.

Compositions provided by the present disclosure can cure by condensation of polythiols. The polythiols can include a thiol-terminated sulfur-containing prepolymer provided by the present disclosure such as a thiol-terminated polysulfide prepolymer, a thiol-terminated polythioether prepolymer, a thiol-terminated sulfur-containing polyformal prepolymer, or a combination of any of the foregoing.

In oxidant-catalyzed thiol-condensation reactions, the reaction may be between thiol-terminated sulfur-containing prepolymers, such as between thiol-terminated polythioether prepolymers, which may be the same or different. In such compositions, one of the thiol-terminated sulfur-containing prepolymers may have a relatively high molecular weight such as represented by Permapol® 3.1E, and the second thiol-terminated sulfur-containing prepolymer may have a comparatively low molecular weight such as represented by Permapol® 3.1.

In addition to a thiol-terminated sulfur-containing prepolymer, an optional primary catalyst, and an ionic liquid catalyst, a composition provided by the present disclosure may contain one or more curing agents. The term curing agent refers to a material that can be added to the composition to react with another component of the composition to provide a cured polymeric network. A curing agent can react with a thiol-terminated sulfur-containing prepolymer to form a cured polymeric network. "Curing" or "cure" can refer to a point at which a coating or sealant achieves a cure hardness of at least 20 durometer Shore A, at least 30 durometer Shore A, or at least 40 durometer Shore A as measured according to ASTM D2440.

A suitable curing agent can contain two or more terminal reactive functional groups that are reactive with terminal thiol groups of a thiol-terminated sulfur-containing prepolymer. Terminal groups reactive with thiol groups include, for example, epoxy groups, Michael acceptor groups, and alkenyl groups.

A curing agent can comprise a polyepoxide, a compound having two or more terminal Michael acceptor groups, or a polyalkenyl compound.

A curing agent may be a monomer, a low molecular weight prepolymer, a high molecular weight prepolymer, or a combination of any of the foregoing.

A curing agent can be an appropriately terminated sulfur-containing prepolymer, such as a polythioether prepolymer, a polysulfide prepolymer, or a sulfur-containing polyformal prepolymer having terminal functional groups reactive with thiol groups.

A curing agent may have a functionality from 2 to 6 or may comprise a mixture of curing agents having different functionalities such that the average functionality is from, for example, 2.1 to 6. A curing agent may have an average functionality of 2, an average functionality of 3, an average functionality from 2.1 to 2.7, or an average functionality from 2.1 to 2.4.

Compositions provided by the present disclosure can comprise a polyepoxide curing agent. Examples of suitable polyepoxides include, for example, polyepoxide resins such as hydantoin diepoxide, diglycidyl ether of bisphenol-A, diglycidyl ether of bisphenol-F, novolac-type epoxides such as DEN® 438 or DEN® 431 (Dow Chemical), certain epoxidized unsaturated resins, and combinations of any of the foregoing. A polyepoxide refers to a compound having two or more reactive epoxy groups.

A polyepoxide curing agent can comprise an epoxy-terminated prepolymer. Examples of suitable epoxy-terminated prepolymers include the epoxy-terminated polyformal prepolymers disclosed in U.S. Pat. No. 8,541,513 and epoxy-terminated polythioether prepolymers disclosed in U.S. Pat. No. 7,671,145, each of which is incorporated by reference in its entirety. In general, when used as a curing agent, an epoxy-terminated prepolymer can have a molecular weight less than 2,000 Daltons, less than 1,500, Daltons, less than 1,000 Daltons, or less than 500 Daltons; such as, for example, from 500 Daltons to 2,000 Daltons, from 500 Daltons to 1,500 Daltons, or from 500 Daltons to 1,000 Daltons.

A polyepoxide curing agent can comprise EPON® 828, DEN® 431, or a combination thereof. EPON® Resin 828 (Momentive Performance Products) is described as a difunctional bisphenol A/epichlorohydrin derived liquid epoxy resin. DEN® 431 is described as an epoxy novolac resin comprising the reaction product of epichlorohydrin and phenol-formaldehyde novolac having an average epoxy functionality of 2.8. Other examples of suitable polyepoxide resins include bisphenol A epoxide resins, bisphenol F epoxide resins, bisphenol S epoxide resins, novolac epoxide resins, aliphatic epoxide resins including glycidyl epoxide resins.

In such compositions, a polyepoxide may comprise from 0.5 wt % to 20 wt % of a composition, from 1 wt % to 10 wt %, from 2 wt % to about 8 wt %, from 2 wt % to 6 wt %, or from 3 wt % to 5 wt %, where wt % is based on the total solids weight of the composition.

Compositions provided by the present disclosure may comprise a thiol-terminated sulfur-containing prepolymer and a Michael acceptor curing agent. A Michael acceptor can be polyfunctional and can have Michael acceptor groups reactive with terminal thiol groups of the thiol-terminated sulfur-containing prepolymer.

A polyfunctional Michael acceptor has at least two Michael acceptor groups. A polyfunctional Michael acceptor may have an average Michael acceptor functionality from 2 to 6, from 2 to 4, from 2 to 3, or from 2.05 to 2.5. A polyfunctional Michael acceptor can be difunctional, such as, divinyl ketone and divinyl sulfone. A Michael acceptor having a functionality greater than two may be prepared by reacting a compound having a Michael acceptor group and a group reactive with terminal groups of a polyfunctionalizing agent such as those disclosed herein, using appropriate reaction conditions.

A Michael acceptor can be used as a curing agent, and the molecular weight of the Michael acceptor can be, for example, less than 600 Daltons, less than 400 Daltons, or less than 200 Daltons, such as from 50 Daltons to 200 Daltons, from 50 Daltons to 400 Daltons, or from 50 Daltons to 600 Daltons.

A curable composition can comprise from about 0.5 wt % to 20 wt % of a Michael acceptor curing agent, from 1 wt % to 10 wt %, from 2 wt % to 8 wt %, from 2 wt % to 6 wt %, or from 3 wt % to 5 wt %, where wt % is based on the total dry solids weight of the curable composition.

When a composition comprises a polyfunctional monomeric Michael acceptor, any suitable monomeric Michael acceptor having at least two Michael acceptor groups such as, for example, divinyl sulfone or other Michael acceptors including any of those disclosed herein may be used.

A Michael acceptor curing agent may also comprise a polyfunctional Michael acceptor adduct such as those disclosed in U.S. Application Publication No. 2013/0345371, which is incorporated by reference in its entirety. A polyfunctional Michael acceptor adduct may be used with a polyfunctional monomeric Michael acceptor such as a compound having two or more activated alkenyl groups such as a vinyl ketone or a vinyl sulfone, such as divinyl sulfone.

A sulfur-containing adduct can comprise a polythioether adduct characterized by a polythioether having at least two terminal Michael acceptor groups. For example, a sulfur-containing adduct can comprise a polythioether adduct comprising:

(a) a backbone comprising the structure of Formula (14):

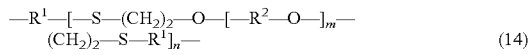

where (i) each $R^1$ is independently selected from a $C_{2-10}$ n-alkanediyl group, a $C_{3-6}$ branched alkanediyl group, a $C_{6-8}$ cycloalkanediyl group, a $C_{6-10}$ alkanecycloalkanediyl group, a heterocyclic group, a -[(—CH$_2$—)$_p$—X—]$_q$—(CH$_2$)$_r$— group, and a -[(—CH$_2$—)$_p$—X—]$_q$—(CH$_2$)$_r$— group in which at least one —CH$_2$— unit is substituted with a methyl group; (ii) each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a -[(—CH$_2$—)$_p$—X—]$_q$—(CH$_2$)$_r$— group; (iii) each X is independently selected from O, S, and a —NR$^6$— group, in which R$^6$ is selected from H and a methyl group; (iv) m ranges from 0 to 50; (v) n is an integer ranging from 1 to 60; (vi) p is an integer ranging from 2 to 6; (vii) q is an integer ranging from 1 to 5; and (viii) r is an integer ranging from 2 to 10; and (b) at least two terminal Michael acceptor groups.

In adducts of Formula (14), $R^1$ can be [—(CHR$^2$)$_p$—X—]$_q$—(CHR$^2$)$_r$— wherein each X is independently selected from —O— and —S—. In adducts of Formula (14), $R^1$ can be [—(CHR$^2$)$_p$—X—]$_q$—(CHR$^2$)$_r$—, each X can be —O— or each X can be —S—.

In adducts of Formula (14), $R^1$ can be -[(—CH$_2$—)$_p$—X—]$_q$—(CH$_2$)$_r$—, where p can be 2, X can be O, q can be 2, r can be 2, $R^2$ can be ethanediyl, m can be 2, and n can be 9.

Michael acceptor groups are well known in the art. A Michael acceptor group can comprise an activated alkene, such as an alkenyl group proximate to an electron-withdrawing group such as an enone, nitro, halo, nitrile, carbonyl, or nitro group. A Michael acceptor group can be selected from a vinyl ketone, a vinyl sulfone, a quinone, an enamine, a ketimine, an aldimine, and an oxazolidine. Each of the Michael acceptor groups may be the same or at least some of the Michael acceptor groups can be different.

A Michael acceptor group can be derived from a vinyl sulfone and has the structure of Formula (15):

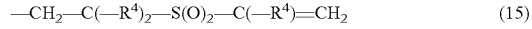

where each $R^4$ is independently selected from hydrogen and $C_{1-3}$ alkyl. In moieties of Formula (15), each $R^4$ can be hydrogen.

A sulfur-containing adduct can comprise a Michael acceptor polythioether adduct of Formula (16a), a Michael acceptor polythioether adduct of Formula (16b), or a combination thereof:

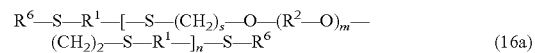

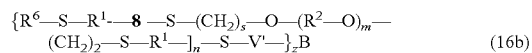

wherein:
each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and -[(—CHR$^3$—)$_p$—X—]$_q$—(—CHR$^3$—)$_r$—, wherein:
 p is an integer from 2 to 6;
 q is an integer from 1 to 5;
 r is an integer from 2 to 10;
 each $R^3$ is independently selected from hydrogen and methyl; and
 each X is independently selected from —O—, —S—, —NH—, and —N(—CH$_3$)—;
each $R^2$ is independently selected from $C_{1-10}$ alkanediyl, $C_{6-8}$ cycloalkanediyl, $C_{6-14}$ alkanecycloalkanediyl, and -[(—CHR$^3$—)$_p$—X—]$_q$—(—CHR$^3$—)$_r$—, wherein p, q, r, $R^3$, and X are as defined for $R^1$;
m is an integer from 0 to 50;
n is an integer from 1 to 60;
s is an integer from 2 to 6;
B represents a core of a z-valent polyfunctionalizing agent B(—V)$_z$ wherein:
 z is an integer from 3 to 6; and
 each V is a moiety comprising a terminal group reactive with a thiol group; and
each —V'— is derived from the reaction of —V with a thiol; and
each $R^6$ is independently a moiety comprising a terminal Michael acceptor group.

In adducts of Formula (16a) and Formula (16b), $R^1$ can be -[(—$CH_2$—)$_p$—X—]$_q$—($CH_2$)$_r$—, where p can be 2, X can be —O—, q can be 2, r can be 2, $R^2$ can be ethanediyl, m can be 2, and n can be 9.

In adducts of Formula (16a) and Formula (16b), $R^1$ can be selected from $C_{2-6}$ alkanediyl and -[—($CHR^3$)$_p$—X—]$_q$—($CHR^3$)$_r$—.

In adducts of Formula (16a) and Formula (16b), $R^1$ can be -[—($CHR^3$)$_p$—X—]$_q$—($CHR^3$)$_r$—, or X can be —O— a or X can be —S—.

In adducts of Formula (16a) and Formula (16b), where $R^1$ can be -[—($CHR^3$)$_p$—X—]$_q$—($CHR^3$)$_r$—, p can be 2, r can be 2, q can be 1, and X can be —S—; or where p can be 2, q can be 2, r can be 2, and X can be —O—; or p can be 2, r can be 2, q can be 1, and X can be —O—.

In adducts of Formula (16a) and Formula (16b), $R^1$ can be -[—($CHR^3$)$_p$—X—]$_q$—($CHR^3$)$_r$—, each $R^3$ can be hydrogen, or at least one $R^3$ can be methyl.

In adducts of Formula (16a) and Formula (16b), each $R^1$ can be the same, or, at least one $R^1$ can be different.

In adducts of Formula (16a) and Formula (16b), each $R^6$ can be independently selected from a vinyl ketone, a vinyl sulfone, a quinone, an enamine, a ketimine, a maleimide, an aldimine, and an oxazolidine. Each of the Michael acceptor groups may be the or at least some of the Michael acceptor groups can be different.

In adducts of Formula (16a) and Formula (16b), each $R^6$ can be independently derived from a vinyl sulfone and has the structure of Formula (15):

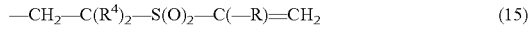

$$—CH_2—C(R^4)_2—S(O)_2—C(—R)=CH_2 \quad (15)$$

wherein each $R^4$ is independently selected from hydrogen and $C_{1-3}$ alkyl. In adducts of Formula (16a) and in Formula (16b) where each $R^6$ is a moiety of Formula (15), each $R^4$ can be hydrogen.

Michael acceptor terminated adducts provided by the present disclosure may also include maleimide-terminated adducts. Suitable maleimide-terminated sulfur-containing adducts are disclosed, for example, in U.S. Application Publication No. 2015/0119549, which is incorporated by reference in its entirety.

Polyalkenyl curing agents can be used, for example, in ultraviolet (UV) curable systems such as disclosed in U.S. Application Publication No. 2013/0284359, and U.S. Application Publication No. 2012/0040104, each of which is incorporated by reference in its entirety.

A polyalkenyl compound can be a polyvinyl ether and/or a polyallyl (polyalkenyl) compound.

An polyalkenyl compound can comprise a compound of Formula (17):

$$CH_2=CH—R^{10}—CH=CH_2 \quad (17)$$

wherein,
$R^{10}$ is selected from $C_{2-6}$ alkanediyl, $C_{6-8}$ cycloalkanediyl, $C_{6-10}$ alkanecycloalkanediyl, $C_{5-8}$ heterocycloalkanediyl, and -[—($CHR^3$)$_p$—X—]$_q$—($CHR^3$)$_r$—, wherein,
each $R^3$ is independently selected from hydrogen and methyl;
each X is independently selected from —O—, —S—, and —NR— wherein R is selected from hydrogen and methyl;
p is an integer from 2 to 6;
q is an integer from 1 to 5; and
r is an integer from 2 to 10.

In polyalkenyl compounds of Formula (17), $R^{10}$ can be $C_{2-6}$ alkanediyl, $C_{6-8}$ cycloalkanediyl, $C_{6-10}$ alkanecycloalkanediyl, or $C_{5-8}$ heterocycloalkanediyl.

In polyalkenyl compounds of Formula (17), $R^{10}$ can be -[—($CHR^3$)$_p$—X—]$_q$—($CHR^4$)$_r$—.

In polyalkenyl compounds of Formula (17), each $R^3$ can be hydrogen.

In polyalkenyl compounds of Formula (17), each X can be selected from —O— and —S—. In polyalkenyl compounds of Formula (17), each X can be —O— or each X can be —S—.

An alkenyl-terminated compound can comprise a polyallyl compound such as a triallyl compound, which refers to compounds comprising three allyl groups ($CH_2=CH$—) and which include, for example, triallyl cyanurate (TAC) and triallyl isocyanurate (TAIC).

An polyalkenyl compound can comprise a polyvinyl ether. Suitable polyvinyl ethers include, for example, those represented by Formula (18):

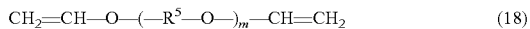

$$CH_2=CH—O—(—R^5—O—)_m—CH=CH_2 \quad (18)$$

where $R^5$ in Formula (18) can be a $C_{2-6}$ n-alkanediyl group, a $C_{2-6}$ branched alkanediyl group, a $C_{6-8}$ cycloalkanediyl group, a $C_{6-10}$ alkanecycloalkanediyl group, or -[(—$CH_2$—)$_p$—O—]$_q$—(—$CH_2$—)$_r$—, where p is an integer having a value ranging from 2 to 6, q is an integer having a value ranging from 1 to 5, and r is an integer having a value ranging from 2 to 10.

Compositions provided by the present disclosure can comprise a Michael acceptor-terminated sulfur-containing prepolymer and a polythiol curing agent.

A polythiol curing agent for a Michael addition may include a thiol-terminated sulfur-containing prepolymer provided by the present disclosure, and a monomeric polythiol, a low molecular weight polythiol prepolymer.

For example, a suitable polythiol prepolymer can include a thiol-terminated sulfur-containing prepolymer provided by the present disclosure such as a thiol-terminated polysulfide prepolymer, a thiol-terminated polythioether prepolymer, a thiol-terminated sulfur-containing polyformal prepolymer, or a combination of any of the foregoing.

A suitable polythiol can comprise a dithiol or a combination of dithiols having the structure of Formula (8), HS—$R^1$—SH, where $R^1$ is defined herein. Examples of suitable dithiols include compounds in which $R^1$ in Formula (8) is a $C_{2-6}$ n-alkanediyl group, i.e., 1,2-ethanedithiol, 1,3-propanedithiol, 1,4-butanedithiol, 1,5-pentanedithiol, or 1,6-hexanedithiol.

Other suitable dithiols include compounds in which $R^1$ in Formula (8) is a $C_{3-6}$ branched alkanediyl group, having one or more pendent groups which can be, for example, methyl or ethyl groups. Suitable compounds in which $R^1$ in Formula (8) is a branched alkanediyl group include 1,2-propanedithiol, 1,3-butanedithiol, 2,3-butanedithiol, 1,3-pentanedithiol and 1,3-dithio-3-methylbutane. Other useful dithiols include those in which $R^1$ is a $C_{6-8}$ cycloalkanediyl or $C_{6-10}$ alkylcycloalkanediyl group, for example, dipentenedimercaptan and ethylcyclohexyldithiol (ECHDT).

Other suitable dithiols include one or more heteroatom substituents in the carbon backbone, that is, dithiols in which X is a heteroatom such as O, S or another bivalent heteroatom radical; a secondary or tertiary amine group, i.e., —NR—, where R is hydrogen or methyl; or another substituted trivalent heteroatom. In dithiols of Formula (8), X can be O or S, and $R^1$ in Formula (8) can be -[(—$CHR^3$—)$_p$—O—]$_q$—(—$CHR^3$—)$_r$—, or -[(—$CHR^3$—)$_p$—S—]$_q$—(—$CHR^3$—)$_r$— where $R^3$ is hydrogen or an alkyl, such as a methyl, group, p is an integer having a value ranging from 2 to 6, q is an integer having a value ranging from 1 to 5, and r is an integer having a value ranging from 2 to 10. The indices s and r can be equal, and, in some cases, both can have the value of 2. Dithiols of this type include dimercaptodiethylsulfide (DMDS) (p, r is 2, q is 1, X is S, $R^3$ is hydrogen); dimercaptodioxaoctane (DMDO) (p, q, r is 2, X is O, $R^3$ is hydrogen); and 1,5-dimercapto-3-oxapentane (p, r is 2, q is 1, X is O, $R^3$ is hydrogen). It is also possible to employ dithiols that include both heteroatom substituents in the carbon backbone and pendent alkyl, such as methyl, groups. Such compounds include methyl-substituted DMDS, such as HS—$CH_2$CH($CH_3$)—S—$CH_2CH_2$—SH, and HS—CH($CH_3$)$CH_2$—S—$CH_2CH_2$—SH, and dimethyl substituted DMDS, such as HS—$CH_2$CH($CH_3$)—S—CH($CH_3$)$CH_2$—SH, and HS—CH($CH_3$)$CH_2$—S—$CH_2$CH($CH_3$)—SH.

A polythiol curing agent for Michael addition can include a polythiol having a functionality, for example, from 2 to 6. For example, a polythiol curing agent can include a combination of dithiols and thiols having a functionality from 3 to 6, such as a polythiol having a functionality of 3.

Compositions provided by the present disclosure can include a thiol-terminated sulfur-containing prepolymer, a thiol-terminated curing agent, an ionic liquid catalyst, and optionally an oxidizing agent. Both the thiol-terminated sulfur-containing prepolymer and a thiol-terminated curing agent can be a thiol-terminated polysulfide prepolymer, a thiol-terminated polythioether prepolymer, a thiol-terminated sulfur-containing polyformal prepolymer, or a combination of any of the foregoing. An oxidizing agent may be any of those disclosed herein, such as manganese dioxide.

Ionic liquid co-catalysts can be used to reduce the amount of oxidizing agent in the curable composition. The use of an ionic liquid as a co-catalyst with oxidizing agents has several advantages. First, the reactivity of particulate oxidizing agents such as manganese dioxide can depend on the particle morphology which is difficult to control and therefore the reactivity of the particulate oxidizing agent may not be reproducible from batch to batch. Ionic liquids can be used in conjunction with an oxidizing agent to control and/or to increase the predictability of the reaction. Ionic liquids can also be used to replace some of the oxidizing agent, which can reduce the overall weight of the sealant.

In compositions provided by the present disclosure an oxidizing agent may be eliminated and only an ionic liquid catalyst may be used to catalyze the reaction.

Oxidant-catalyzed sealant compositions containing a mixture of thiol-terminated polysulfides and thiol-terminated polythioethers are disclosed, for example, in U.S. Application Publication No. 2008/0200610, which is incorporated by reference in its entirety.

A curable composition provided by the present disclosure may comprise a thiol-terminated sulfur-containing prepolymer, a polyepoxide curing agent, an ionic liquid catalyst, and an optional amine catalyst.

In sealants such as those described in U.S. Pat. No. 6,123,179 an amine catalyst is used to provide a cured product. Such systems typically cure in over two hours and although the cured sealants exhibit acceptable fuel resistance and thermal resistance for many applications, a faster curing rate with improved performance is desirable for certain aerospace sealant applications.

In sealants such as those described in U.S. Pat. No. 6,172,179 thiol-terminated polythioethers and polyepoxide curing agents can be reacted in the presence of a base to provide cured aerospace sealants. Other examples of base catalyzed thiol-epoxy systems are disclosed in U.S. Application Publication No. 2014/02722287, in U.S. Pat. No. 8,710,159, and in U.S. Application Publication No. 2014/0110881; each of which is incorporated by reference in its entirety. Polyepoxide curing agents are used to cure thiol-terminated sulfur-containing polymers such as polythioethers and polysulfides. Examples of such systems are disclosed, for example, in U.S. Application Publication Nos. 2005/0010003, 2006/0270796, 2007/0287810, 2009/0326167, and 2010/036063, and include any of those described herein. These systems are useful as sealants and can meet the demanding performance requirements of the aerospace industry. An ionic liquid catalyst can be used in any of these sealant compositions to replace the amine catalyst or to reduce the amount of amine catalyst in the composition.

Suitable amine catalysts include tertiary amine catalysts. Examples of suitable tertiary amine catalysts include N,N-dimethylethanolamine (DMEA), 1,4-diazabicyclo[2.2.2]octane (DABCO), triethylene diamine (TEDA), bis(2-dimethylaminoethyl)ether (BDMAEE), N-ethylmorpholine, N',N'-dimethylpiperazine, N,N,N',N',N''-pentamethyl-diethylenetriamine (PMDETA), N,N'-dimethylcyclohexylamine (DMCHA), N,N-dimethylbenzylamine (DMBA), N,N-dimethylcethylamine, N,N,N',N'',N''-pentamethyl-dipropylenetriamine (PMDPTA), triethylamine, and 1-(2-hydroxypropyl) imidazole. Other suitable amine catalysts include amidine catalysts such as tetramethylguanidine (TMG), diazabicyclononene (DBN), 1,8-diazabicyclo[5.4.0]undec-7-ene (DBU) and imidazoles; and bicyclic guanidines such as 1,5,7,-triazabicyclo[4.4.0]dec-5-ene (TBD), and 1,5,7,-triazabicyclo[4.4.0]dec-5-ene, 7-methyl (MTBD).

An amine catalyst can be selected from DBU, DABCO, and a combination thereof. Compositions may comprise one or more different types of amine catalyst.

Compositions provided by the present disclosure can include a thiol-terminated sulfur-containing prepolymer, a Michael acceptor curing agent, an ionic liquid catalyst and an optional amine catalyst.

Amine-catalyzed Michael addition reactions with thiol-terminated sulfur-containing prepolymers are disclosed, for example, in U.S. Application Publication No. 2013/0345371, which is incorporated by reference in its entirety. The compositions disclosed in U.S. Application Publication No. 2013/0345371 employ one or more base catalysts such as amine catalysts. In the presence of a strong base such as 1,8-diazabicyclo[5.4.0]undec-7-ene (DBU) or 1,4-diazabicyclo[2.2.2]octane (DABCO) or a $C_{6-10}$ primary amine, the thiol-Michael addition reaction can be fast and the cure time is typically less than 2 hours. Without a strong base catalyst, such as triethylamine, the Michael addition reaction between, for example, a thiol-terminated polythioether and a Michael acceptor is slow providing a working time, for example, depending on the temperature, of several days to weeks. However, the physical properties of the cured composition are less than desired. To provide cure-on-demand systems, amine catalysts can be incorporated into controlled-release encapsulants or matrices that can release the amine catalyst upon activation. Nevertheless, the presence of amine catalysts in cure on demand systems can compromise the properties of a cured sealant formed from these compositions. Therefore, in amine-catalyzed systems it is desirable to reduce or eliminate the amine catalyst.

The amount of a base catalyst such as an amine catalyst can be reduced by using an ionic liquid as a co-catalyst. For example, a curable composition may include less than 0.5 wt % ionic liquid, less than 0.4 wt %, less than 0.2 wt %, 0.1 wt % ionic liquid, less than 0.05 wt % ionic liquid, less than 0.02 wt % ionic liquid, or less than 0.01 wt % ionic liquid; such as from 0.01 wt % to 0.5 wt %, from 0.01 wt % to 0.2 wt %, or from 0.01 wt % to 0.1 wt %, where wt % is based on the total solids weight of the composition.

An ionic liquid catalyst may replace the amine catalyst, or a curable composition may comprise both the ionic liquid co-catalyst and an amine catalyst. In such compositions, the amount of amine catalyst in the composition may be less than the amount of amine catalyst used in a similar curable composition without the ionic liquid co-catalyst.

Thus, ionic liquids may be used as co-catalysts or as a stand-alone catalyst in base-catalyzed systems, such as amine-catalyzed systems. Amine-catalyzed Michael addition curing chemistries based on sulfur-containing prepolymers are disclosed, for example, in U.S. Application Publication Nos. 2013/0345371; 2013/0345389; 2014/0275461; 2014/0378649; 2015/0119549; and 2015/0252232; each of which is incorporated by reference in its entirety.

Compositions provided by the present disclosure can comprise a base catalyst such as an amine catalyst. For example, in embodiments in which the sulfur-containing polymer is thiol-terminated and the compound is a difunctional Michael acceptor, the reaction may take place in the presence of an amine catalyst. Examples of suitable amine catalysts include, for example, triethylenediamine (1,4-diazabicyclo[2.2.2]octane, DABCO), dimethylcyclohexylamine (DMCHA), dimethylethanolamine (DMEA), bis-(2-dimethylaminoethyl)ether, N-ethylmorpholine, triethylamine, 1,8-diazabicyclo[5.4.0]undecene-7 (DBU), pentamethyldiethylenetriamine (PMDETA), benzyldimethylamine (BDMA), N,N,N'-trimethyl-N'-hydroxyethyl-bis(aminoethyl)ether, and N'-(3-(dimethylamino)propyl)-N,N-dimethyl-1,3-propanediamine.

In compositions comprising polyepoxides, a curable composition may comprise a base catalyst, including amine catalysts such as any of those disclosed herein.

A Michael acceptor curing agent may comprise a monomer, a prepolymer, or a combination thereof.

Compositions provided by the present disclosure can include a Michael acceptor-terminated sulfur-containing prepolymer and a thiol-terminated sulfur-containing prepolymer. A Michael acceptor-terminated sulfur-containing prepolymer may be a polythioether prepolymer, a polysulfide prepolymer, or a sulfur-containing polyformal prepolymer including any of those described in the present disclosure. A compound having at least two Michael acceptor groups can comprise a Michael acceptor-terminated sulfur-containing prepolymer such as a Michael acceptor-terminated polythioether prepolymer. At least one of the compounds terminated with groups reactive with Michael acceptor groups and the compound having at least two Michael acceptor groups can comprise a polythioether prepolymer.

Michael addition chemistries may be employed in a variety of ways to provide curable compositions. For example, a curable composition provided by the present disclosure may comprise: (a) a thiol-terminated sulfur-containing prepolymer and a Michael acceptor-terminated sulfur-containing prepolymer; (b) a thiol-terminated sulfur-containing prepolymer, a low molecular weight polythiol, and a Michael acceptor-terminated sulfur-containing prepolymer; or (c) a thiol-terminated sulfur-containing prepolymer, a Michael acceptor-terminated sulfur-containing prepolymer, and a low molecular weight compound having at least two Michael acceptor groups; and (d) a thiol-terminated sulfur-containing prepolymer, a low molecular weight polythiol, a Michael acceptor-terminated sulfur-containing prepolymer, and a low molecular weight compound having at least two Michael acceptor groups.

Michael acceptor-terminated sulfur-containing prepolymers and thiol-terminated sulfur-containing polymers may be derived from polythioethers, polysulfides, sulfur-containing polyformals, or combinations of any of the foregoing.

Low molecular weight polythiols and low molecular weight Michael acceptors can have an average molecular weight, for example, less than 400 Daltons, less than 600 Daltons, or less than 1,000 Daltons.

Michael acceptor-terminated sulfur-containing prepolymers can have at least two terminal unsaturated groups that are activated for Michael addition such as activated unsaturated groups that serve as Michael addition acceptors.

Michael acceptor-terminated sulfur-containing prepolymers can comprise at least two terminal Michael acceptor groups. A Michael-acceptor-terminated sulfur-containing prepolymer may be difunctional, and may have a functionality greater than 2 such as 3, 4, 5, or 6. A Michael-acceptor-terminated sulfur-containing prepolymer may comprise a combination of Michael-acceptor-terminated sulfur-containing prepolymer having different functionalities characterized by an average functionality from 2.05 to 6, from 2.1 to 4, from 2.1 to 3, from 2.2 to 2.8, or from 2.4 to 2.6. Michael-acceptor-terminated sulfur-containing prepolymers have at least two terminal Michael acceptor groups, and can have two Michael acceptor groups, 3, 4, 5, or 6 Michael acceptor groups. A Michael-acceptor-terminated sulfur-containing prepolymer may comprise a combination of adducts having different numbers of terminal Michael acceptor groups characterized, for example, by an average Michael acceptor functionality of from 2.05 to 6, from 2.1 to 4, from 2.1 to 3, from 2.2 to 2.8, or from 2.4 to 2.6.

Suitable Michael acceptor-terminated sulfur-containing prepolymers include Michael acceptor-terminated polythioethers, Michael acceptor-terminated polysulfides, Michael acceptor-terminated sulfur-containing polyformals, and combinations of any of the foregoing. For example, any of the polythioethers, polysulfides, and sulfur-containing polyformals suitable for use as thiol-terminated sulfur-containing prepolymers may also be used as the backbone for a Michael acceptor-terminated sulfur-containing prepolymer.

Michael acceptor-terminated sulfur-containing prepolymers suitable for use in aerospace sealant applications are disclosed, for example, in U.S. Application Publication No. 2014/0378649 and U.S. Application Publication No. 2015/0119549, each of which is incorporated by reference in its entirety.

A Michael acceptor-terminated sulfur-containing prepolymer can comprise a Michael acceptor-terminated polythioether.

A Michael acceptor-terminated sulfur-containing prepolymer can comprise a Michael acceptor-terminated polythioether comprising:

(a) a backbone comprising the structure of Formula (6):

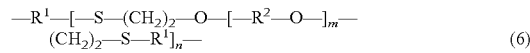

$$—R^1—[—S—(CH_2)_2—O—[—R^2—O—]_m—(CH_2)_2—S—R^1]_n— \quad (6)$$

where (i) each $R^1$ is independently selected from a $C_{2-10}$ n-alkanediyl group, a $C_{3-6}$ branched alkanediyl group, a $C_{6-8}$ cycloalkanediyl group, a $C_{6-10}$ alkanecycloalkanediyl group, a heterocyclic group, a $-[(—CHR^3—)_p—X—]_q—(CHR^3)_r—$ group, wherein each $R^3$ is independently selected from hydrogen and methyl; (ii) each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a -[—($CH_2$—)$_p$—X—]$_q$—($CH_2$)$_r$— group; (iii) each X is independently selected from O, S, and a —$NR^6$— group, in which $R^6$ is selected from hydrogen and a methyl group; (iv) m ranges from 0 to 50; (v) n is an integer ranging from 1 to 60; (vi) p is an integer ranging from 2 to 6; (vii) q is an integer ranging from 1 to 5; and (viii) r is an integer ranging from 2 to 10; and (b) at least two terminal Michael acceptor groups.

In prepolymers of Formula (6), $R^1$ can be -[—($CHR^3$)$_p$—X—]$_q$—($CHR^3$)$_r$— wherein each X is independently selected from —O— and —S—. In prepolymers of Formula (6), $R^1$ can be -[—($CHR^3$)$_p$—X—]$_q$—($CHR^3$)$_r$—, and each X can be —O— or each X can be —S—.

In prepolymers of Formula (6), $R^1$ can be -[—($CH_2$)$_p$—X—]$_q$—($CH_2$)$_r$— where each X is independently selected from —O— and —S—. In prepolymers of Formula (6), $R^1$ can be -[—($CH_2$)$_p$—X—]$_q$—($CH_2$)$_r$—, and each X can be —O— or each X can be —S—.

In prepolymers of Formula (6), $R^1$ can be -[(—$CH_2$—)$_p$—X—]$_q$—($CH_2$)$_r$—, where p can be 2, X can be O, q can be 2, r can be 2, $R^2$ can be ethanediyl, m can be 2, and n can be 9.

A Michael acceptor-terminated sulfur-containing prepolymer can comprise a Michael acceptor-terminated polythioether of Formula (19a), a Michael acceptor-terminated polythioether of Formula (19b), or a combination thereof:

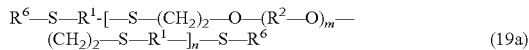

(19a)

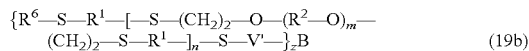

(19b)

wherein:
each $R^1$ independently is selected from $C_{2-10}$ alkanediyl, $C_{6-8}$ cycloalkanediyl, $C_{6-10}$ alkanecycloalkanediyl, $C_{5-8}$ heterocycloalkanediyl, and -[(—$CHR^3$—)$_p$—X—]$_q$—(—$CHR^3$—)$_r$—, wherein:
p is an integer from 2 to 6;
q is an integer from 1 to 5;
r is an integer from 2 to 10;
each $R^3$ is independently selected from hydrogen and methyl; and
each X is independently selected from —O—, —S—, —NH—, and —N(—$CH_3$)—;
each $R^2$ is independently selected from $C_{1-10}$ alkanediyl, $C_{6-8}$ cycloalkanediyl, $C_{6-14}$ alkanecycloalkanediyl, and -[(—$CHR^3$—)$_p$—X—]$_q$—(—$CHR^3$—)$_r$—, wherein p, q, r, $R^3$, and X are as defined for $R^1$;
m is an integer from 0 to 50;
n is an integer from 1 to 60;
B represents a core of a z-valent, polyfunctionalizing agent B(—V)$_z$ wherein:
z is an integer from 3 to 6; and
each V is a group comprising a terminal group reactive with thiol groups; and
each —V'— is derived from the reaction of —V with a thiol; and
each $R^6$ is independently a moiety comprising a terminal Michael acceptor group.

In prepolymers of Formula (19a) and Formula (19b), $R^1$ can be -[(—$CH_2$—)$_p$—X—]$_q$—($CH_2$)$_r$—, where p can be 2, X can be —O—, q can be 2, r can be 2, $R^2$ can be ethanediyl, m can be 2, and n can be 9.

In prepolymers of Formula (19a) and Formula (19b), $R^1$ can be selected from $C_{2-6}$ alkanediyl and -[—($CHR^3$)$_p$—X—]$_q$—($CHR^3$)$_r$—.

In prepolymers of Formula (19a) and Formula (19b), $R^1$ can be -[—($CHR^3$)$_p$—X—]$_q$—($CHR^3$)$_r$—, where X can be —O— or X can be —S—.

In prepolymers of Formula (19a) and Formula (19b), $R^1$ can be -[—($CHR^3$)$_p$—X—]$_q$—($CHR^3$)$_r$—, and p can be 2, r can be 2, q can be 1, and X can be —S—; or p can be 2, q can be 2, r can be 2, and X can be —O—; or p can be 2, r can be 2, q can be 1, and X can be —O—.

In prepolymers of Formula (19a) and Formula (19b), $R^1$ can be -[—($CHR^3$)$_p$—X—]$_q$—($CHR^3$)$_r$—, where each $R^3$ can be hydrogen, or at least one $R^3$ can be methyl.

In prepolymers of Formula (19a) and Formula (19b), each $R^1$ can be the same, or at least one $R^1$ can be different.

In prepolymers of Formula (19a) and Formula (19b), each —V can comprise a terminal alkenyl group.

A Michael acceptor group terminating a sulfur-containing prepolymer may be any suitable Michael acceptor group. A terminal Michael acceptor group can be derived from a bis(vinylsulfonyl)alkanol or can be derived from a bismaleimide.

In prepolymers of Formula (19a) and Formula (19b), each $R^6$ can be derived from a bismaleimide such as 1,1'-(methylenebis(4,1-phenylene)bis(1H-pyrrole-2,5-dione). Each $R^6$ can be derived from ethylenebismaleimide, 1,6-bismaleimidohexane, 2,4-dimaleimidotoluene, N,N'-1,3-phenylenedimaleimide; 1,4-bis(maleimido)butane trimethylenebismaleimide; p,p'-dimaleimidodiphenylmethane; pentamethylenebismaleimide 1H-pyrrole-2,5-dione; 1,1'-(1,8-octanediyl)bis-, 1H-pyrrole-2,5-dione, 1,1'-(1,7-heptanediyl)bis-, 4,4'-dithiobis(phenylmaleimide); methylenebis(N-carbamylmaleimide), 1,9-bis(maleimide)nonane; 1,1'-decane-1,10-diylbis(1H-pyrrole-2,5-dione); O-phenylene dimaleimide, bis(N-maleimidomethyl)ether; 1,5-bis(maleimide)-2-methyl-pentane; N,N'-1,4-phenylenedimaleimide; 1,1'-(2-methyl-1,3-phenylene)bis(1H-pyrrole-2,5-dione); Kerimid 601 resin; tetrakis(N-2-aminoethylmaleimide); 1-(2,5-dimethylphenyl)pyrrole-2,5-dione; SureCN331305; SureCN349749; or 1,1'-biphenyl-4,4'-diylbis(1H-pyrrole-2,5-dione).

A Michael acceptor-terminated sulfur-containing prepolymer can comprise at least two terminal maleimide groups.

Michael acceptor groups are well known in the art. A Michael acceptor group can comprise an activated alkene, such as an alkenyl group proximate to an electron-withdrawing group such as an enone, nitro, halo, nitrile, carbonyl, or nitro group. A Michael acceptor group can be selected from a vinyl ketone, a vinyl sulfone, and a quinone. A Michael acceptor group can comprise a bis(sulfonyl)alkanol group such as a 1-(ethylenesulfonyl)-n-(vinylsulfonyl)alkanol group, or a 1-(ethylenesulfonyl)-3-(vinylsulfonyl)propan-2-ol group. Each of the Michael acceptor groups may be the same or at least some of the Michael acceptor groups can be different.

Michael acceptor-terminated sulfur-containing prepolymers may comprise at least two terminal 1-(ethylenesulfonyl)-n-(vinylsulfonyl)alkanol groups, such as two terminal 1-(ethylenesulfonyl)-n-(vinylsulfonyl)alkanol groups, 3, 4, 5, or 6 terminal 1-(ethylenesulfonyl)-n-(vinylsulfonyl)alkanol groups. A Michael acceptor-terminated sulfur-containing prepolymer may comprise a combination of adducts having different numbers of terminal 1-(ethylenesulfonyl)-n-(vinylsulfonyl)alkanol groups characterized, for example, by an average 1-(ethylenesulfonyl)-n-(vinylsulfonyl)alkanol functionality from 2.05 to 6, from 2.1 to 4, from 2.1 to 3, from 2.2 to 2.8, or from 2.4 to 2.6.

A Michael acceptor group can be derived from a vinyl sulfone and has the structure of Formula (20):

$$—CH_2—(—R^{16})_2—S(O)_2—C(—R^{16})=CH_2 \quad (20)$$

where each $R^{16}$ is independently selected from hydrogen and $C_{1-3}$ alkyl. In a Michael acceptor group of Formula (20), each $R^{13}$ can be hydrogen. Michael acceptor-terminated bis(sulfonyl)alkanol-containing polythioethers may be prepared, for example, by reacting a thiol-terminated bis(sulfonyl)alkanol-containing polythioether with a compound having a terminal Michael acceptor group and a group reactive with thiol groups such as a divinylsulfone, in the presence of a phosphine catalyst. Michael acceptor/polythioether chemistries and compounds are disclosed, for example, in U.S. Application Publication No. 2013/0345371, which is incorporated by reference in its entirety.

A Michael acceptor group can be derived from a bis(sulfonyl)alkanol and has the structure of Formula (21a) or Formula (21b):

$$—CH_2—CH_2—S(O)_2—R^{10}—CH(—OH)—R^{10}—S\\(O)_2—CH=CH_2 \quad (21a)$$

$$—CH_2—CH_2—S(O)_2—CH_2—CH(—OH)—CH_2—S\\(O)_2—CH=CH_2 \quad (21b)$$

where each $R^{10}$ is independently selected from $C_{1-3}$ alkanediyl.

In Michael acceptor groups of Formula (19a) and Formula (19b), each —V can comprise a terminal alkenyl group.

In prepolymers of Formula (19a) and Formula (19b), each $R^6$ can be independently selected from a vinyl ketone, a vinyl sulfone, and a quinone. In prepolymers of Formula (19a) and Formula (19b), each of the Michael acceptor groups may be the same or at least some of the Michael acceptor groups are different.

In prepolymers of Formula (19a) and Formula (19b), each $R^6$ can be independently a bis(sulfonyl)alkanol group.

In Michael acceptor-terminated sulfur-containing prepolymers the prepolymers can comprise at least two terminal vinylsulfonyl groups.

A Michael acceptor-terminated sulfur-containing prepolymer may be terminated in at least two vinyl sulfonyl groups or at least two terminal 1-(ethylenesulfonyl)-n-(vinylsulfonyl)alkanol groups.

A compound having a Michael acceptor group and a group that is reactive with the terminal groups of the sulfur-containing prepolymer may be a bis(sulfonyl)alkanol having the formula $R—CH_2—CH_2—S(O)_2—R^{10}—CH(—OH)—R^{10}—S(O)_2—CH=CH_2$ where R is a moiety having a terminal group that is reactive with the terminal groups of the sulfur-containing prepolymer; and each $R^{10}$ can be independently selected from $C_{1-3}$ alkanediyl. A bis(vinyl)alkanol can be a bis(vinylsulfonyl)alkanol.

Maleimide-terminated sulfur-containing prepolymers provided by the present disclosure can comprise at least two terminal maleimide groups. A maleimide-terminated sulfur-containing prepolymer may be difunctional, or may have a functionality greater than 2 such as 3, 4, 5, or 6. A maleimide-terminated sulfur-containing prepolymer may comprise a mixture of maleimide-terminated sulfur-containing prepolymer having different functionalities characterized by an average functionality from 2.05 to 6, from 2.1 to 4, from 2.1 to 3, from 2.2 to 2.8, or from 2.4 to 2.6. Maleimide-terminated sulfur-containing prepolymer can have at least two terminal maleimide groups, or can have two terminal 1-(4-(4-(3-yl-2,5-dioxopyrrolidin-1-yl)benzyl)phenyl)-1H-pyrrole-2,5-dione groups, or can have more than two terminal groups such as 3, 4, 5, or 6 terminal 1-(4-(4-(3-yl-2,5-dioxopyrrolidin-1-yl)benzyl)phenyl)-1H-pyrrole-2,5-dione groups. A maleimide-terminated sulfur-containing prepolymer may comprise a combination of adducts having different numbers of terminal 1-(4-(4-(3-yl-2,5-dioxopyrrolidin-1-yl)benzyl)phenyl)-1H-pyrrole-2,5-dione groups characterized, for example, by an average 1-(4-(4-(3-yl-2,5-dioxopyrrolidin-1-yl)benzyl)phenyl)-1H-pyrrole-2,5-dione functionality from 2.05 to 6, from 2.1 to 4, from 2.1 to 3, from 2.2 to 2.8, or from 2.4 to 2.6.

The double bond of maleimides can react with thiol groups at pH 6.5 to pH 7.5 and is more reactive than (meth)acrylates. At neutral pH, the reaction of maleimides with thiols can be 1,000 times faster than the reaction of maleimides with amines. Compositions prepared from maleimide resins exhibit excellent thermomechanical stability and anti-flammability.

A maleimide-terminated sulfur-containing prepolymer can comprises a maleimide-terminated polythioether prepolymer having at least two terminal maleimide groups such as, for example, at least two terminal 1-(4-(4-(3-yl-2,5-dioxopyrrolidin-1-yl)benzyl)phenyl)-1H-pyrrole-2,5-dione groups.

Terminal Michael acceptor groups can be selected from 1,3-bis(vinylsulfonyl-2-propanol, 1,1'-(methylenedi-4,1-phenylene)bismaleimide, or a combination thereof.

In prepolymers of Formula (19a) and Formula (19b), each $R^6$ can be independently derived from a bismaleimide. Each of the terminal maleimide moieties may be the same or at least some of the terminal maleimide moieties are different. In prepolymers of Formula (19a) and Formula (19b), each $R^6$ can be 1-(4-(4-(3-yl-2,5-dioxopyrrolidin-1-yl)benzyl)phenyl)-1H-pyrrole-2,5-dione.

A maleimide-terminated sulfur-containing prepolymer can comprise a maleimide-terminated polythioether prepolymer comprising:

(a) a backbone comprising the structure of Formula (6):

$$—R^1—[—S—(CH_2)_2—O—[—R^2—O—]_m—\\(CH_2)_2—S—R^1]_n— \quad (6)$$

where (i) each $R^1$ is independently selected from a $C_{2-10}$ n-alkanediyl group, a $C_{3-6}$ branched alkanediyl group, a $C_{6-8}$ cycloalkanediyl group, a $C_{6-10}$ alkanecycloalkanediyl group, a heterocyclic group, a -[(—CHR^3—)_p—X—]_q—(CHR^3)_r— group, wherein each $R^3$ is independently selected from hydrogen and methyl; (ii) each $R^2$ is independently selected from a $C_{2-10}$ n-alkanediyl group, a $C_{3-6}$ branched alkanediyl group, a $C_{6-8}$ cycloalkanediyl group, a $C_{6-14}$ alkanecycloalkanediyl group, a heterocyclic group, and a -[(—CH_2—)_p—X—]_q—(CH_2)_r— group; (iii) each X is independently selected from O, S, and a —NR^6— group, in which $R^6$ is selected from H and a methyl group; (iv) m ranges from 0 to 50; (v) n is an integer ranging from 1 to 60; (vi) p is an integer ranging from 2 to 6; (vii) q is an integer ranging from 1 to 5; and (viii) r is an integer ranging from 2 to 10; and (b) at least two terminal maleimide groups.

In prepolymers of Formula (6), $R^1$ can be -[—(CHR^3)_p—X—]_q—(CHR^3)_r— where each X can be independently selected from —O— and —S—. In prepolymers of Formula (6), $R^1$ can be -[—(CHR^3)_p—X—]_q—(CHR^3)_r—, and each X can be —O— or each X can be —S—.

In prepolymers of Formula (6), $R^1$ can be -[—(CH_2)_p—X—]_q—(CH_2)_r— where each X can be independently selected from —O— and —S—. In prepolymers of Formula (6), $R^1$ can be -[—$(CH_2)_p$—X—]$_q$—$(CH_2)_r$—, and each X can be —O— or each X can be —S—.

In prepolymers of Formula (6), $R^1$ can be -[(—$CH_2$—)$_p$—X—]$_q$—$(CH_2)_r$—, where p can be 2, X can be O, q can be 2, r can be 2, $R^2$ can be ethanediyl, m can be 2, and n can be 9.

A terminal maleimide group comprises the structure of Formula (22):

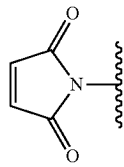

(22)

A terminal bismaleimide moiety refers to a moiety having a terminal maleimide group. A terminal maleimide group can be derived from a bismaleimide, such as a compound having the structure of Formula (4a):

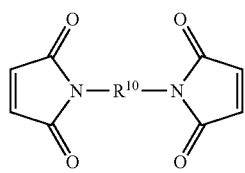

(4a)

where $R^{10}$ is a divalent organic moiety, and the terminal group has the structure of Formula (4b):

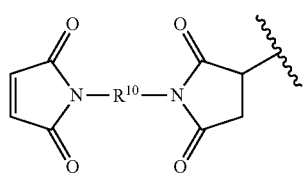

(4b)

and is referred to as a 1-(4-(4-(3-yl-2,5-dioxopyrrolidin-1-yl)benzyl)phenyl)-1H-pyrrole-2,5-dione group. A terminal maleimide group can be derived from 1,1'-(methylenedi-4,1-phenylene)bismaleimide of Formula (5a), also referred to as 1,1'-(methylenebis(4,1-phenylene)bis(1H-pyrrole-2,5-dione), and the terminal group has the structure of Formula (5b):

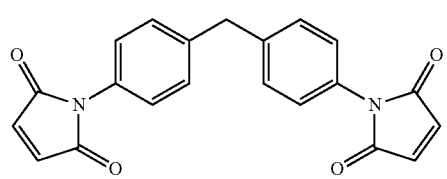

(5a)

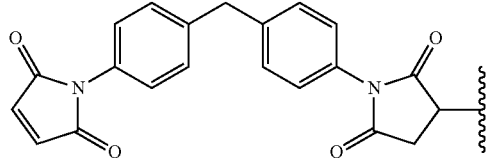

(5b)

A maleimide group can comprise a 1-(4-(4-(3-yl-2,5-dioxopyrrolidin-1-yl)benzyl)phenyl)-1H-pyrrole-2,5-dione group. Each of the terminal maleimide groups may be the same or at least some of the terminal maleimide groups are different.

Other examples of compounds having two or more maleimide groups include ethylenebismaleimide; 1,6-bis-maleimidohexane; 2,4-dimaleimidotoluene, N,N'-1,3-phenylenedimaleimide; 1,4-bis(maleimido)butane trimethylenebismaleimide; p,p'-dimaleimidodiphenylmethane; pentamethylenebismaleimide 1H-pyrrole-2,5-dione; 1,1'-(1,8-octanediyl)bis-, 1H-pyrrole-2,5-dione, 1,1'-(1,7-heptanediyl)bis-, 4,4'-dithiobis(phenylmaleimide); methylenebis(N-carbamylmaleimide), 1,9-bis(maleimide)nonane; 1,1'-decane-1,10-diylbis(1H-pyrrole-2,5-dione); O-phenylene dimaleimide, bis(N-maleimidomethyl)ether; 1,5-bis(maleimide)-2-methyl-pentane; N,N'-1,4-phenylenedimaleimide; 1,1'-(2-methyl-1,3-phenylene)bis(1H-pyrrole-2,5-dione); Kerimid 601 resin; tetrakis(N-2-aminoethylmaleamide); 1-(2,5-dimethylphenyl)pyrrole-2,5-dione; SureCN331305, SureCN349749; and 1,1'-biphenyl-4,4'-diylbis(1H-pyrrole-2,5-dione).

To prepare a Michael acceptor-terminated sulfur-containing prepolymer, a sulfur-containing polymer such as those disclosed herein may be reacted with a compound having a Michael acceptor group and a group that is reactive with the terminal groups of the sulfur-containing prepolymer.

A Michael acceptor group can be selected from a vinyl ketone, a vinyl sulfone, a maleimide, and a quinone. A Michael acceptor group can be a vinyl ketone or a vinyl sulfone such as derived from divinyl sulfone. A compound having a Michael acceptor group can be derived from divinyl sulfone and the sulfur-containing polymer may be thiol-terminated such as a thiol-terminated polythioether, a thiol-terminated polysulfide, or a combination thereof.

A Michael acceptor group can be a bis(sulfonyl)alkanol such as a group derived from a bis(vinylsulfonyl) alkanol. A compound having a Michael acceptor group can be derived from bis(vinylsulfonyl)alkanol and the sulfur-containing polymer may be thiol-terminated such as a thiol-terminated polythioether, a thiol-terminated polysulfide, or a combination thereof.

A Michael acceptor-terminated sulfur-containing prepolymer can comprise a Michael acceptor urethane-containing prepolymer. Michael acceptor-terminated urethane-containing prepolymers are disclosed in U.S. Application Publication No. 2015/0252232, which is incorporated by reference in its entirety.

Michael acceptor-terminated urethane-containing prepolymers can comprise urethanes incorporated into the backbone of a sulfur-containing prepolymer. The Michael acceptor-terminated urethane-containing prepolymers can be useful in providing cured sealants having enhanced tensile strength.

For certain applications, Michael acceptor-terminated urethane-containing prepolymers represent an improvement over previously disclosed Michael acceptor-terminated sulfur-containing prepolymers such as those disclosed in U.S. Application Publication No. 2013/0345371 and U.S. Application Publication No. 2013/0345389. Cured sealants prepared from Michael acceptor-terminated urethane-containing prepolymers exhibit enhanced tensile strength and surface adhesion compared to the Michael acceptor-terminated sulfur-containing prepolymers disclosed in those applications. The enhanced tensile strength is believed to be imparted by the incorporation of urethane segments into the polymer backbone and the improved surface adhesion is believed to result from termination with groups that function as both metal ligands and as Michael acceptors.

Michael acceptor-terminated urethane-containing prepolymers comprise a urethane- and sulfur-containing backbone capped with isocyanate groups that are further capped with Michael acceptor groups.

Michael acceptor-terminated urethane-containing prepolymers include polythioethers, polysulfides, and combinations of any of the foregoing.

It can be appreciated that Michael acceptor-terminated urethane-containing prepolymers may be synthesized by a number of routes. The functional groups of the precursors can be adapted and selected for a particular reaction chemistry. For example, it can be convenient that the sulfur-containing prepolymer comprise thiol or hydroxyl terminal groups. In embodiments in which the sulfur-containing prepolymer has terminal hydroxyl groups, a diisocyanate may be directly reacted with the sulfur-containing prepolymer. In prepolymers in which the precursor sulfur-containing prepolymer is thiol-terminated the thiol groups may be capped with a hydroxyl functional compound to provide a hydroxyl-terminated sulfur-containing prepolymer that may then be reacted with a diisocyanate.

A Michael acceptor-terminated urethane-containing prepolymer can comprise a Michael acceptor-terminated urethane-containing prepolymer of Formula (23a), a Michael acceptor-terminated urethane-containing prepolymer of Formula (23b), or a combination thereof:

$$R^{30}-C(=O)-NH-R^{20}-NH-C(=O)-[-R^{60}-C(=O)-NH-R^{20}-NH-C(=O)-]_w-R^{60}-C(=O)-NH-R^{20}-NH-C(=O)-R^{30} \quad (23a)$$

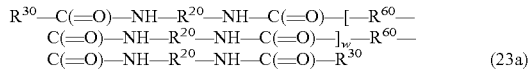
(23b)

where,
w is an integer from 1 to 100;
each $R^{13}$ independently comprises $C_{2-10}$ alkanediyl;
each $R^{20}$ independently comprises a core of a diisocyanate;
each $R^{30}$ independently comprises at least one terminal Michael acceptor group;
each $R^{50}$ independently comprises a core of a sulfur-containing prepolymer;
each $R^{60}$ independently comprises a moiety having the structure of Formula (24):

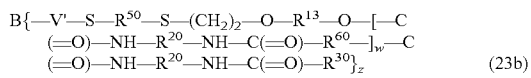
(24)

B represents a core of a z-valent, polyfunctionalizing agent $B(-V)_z$ wherein,
z is an integer from 3 to 6; and
each V is a moiety comprising a terminal group reactive with a thiol group; and
each —V'— is derived from the reaction of —V with a thiol.

In prepolymers of Formula (23a) and Formula (23b), each $R^{50}$ can be derived from a polythioether and comprises the structure of Formula (6):

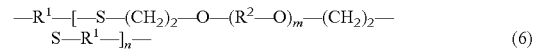
(6)

wherein,
each $R^1$ independently is selected from $C_{2-10}$ alkanediyl, $C_{6-8}$ cycloalkanediyl, $C_{6-14}$ alkanecycloalkanediyl, $C_{5-8}$ heterocycloalkanediyl, and -[(—CHR$^3$—)$_p$—X—]$_q$—(—CHR$^3$—)$_r$—, wherein,
p is an integer from 2 to 6;
q is an integer from 1 to 5;
r is an integer from 2 to 10;
each $R^3$ is independently selected from hydrogen and methyl; and
each X is independently selected from —O—, —S—, —NH—, and —N(—CH$_3$)—;
each $R^2$ is independently selected from $C_{1-10}$ alkanediyl, $C_{6-8}$ cycloalkanediyl, $C_{6-14}$ alkanecycloalkanediyl, and -[(—CHR$^3$—)$_p$—X—]$_q$—(—CHR$^3$—)$_r$—, wherein p, q, r, $R^3$, and X are as defined as for $R^1$;
m is an integer from 0 to 50; and
n is an integer from 1 to 60.

Michael acceptor-terminated urethane-containing prepolymers can be derived from the reaction of a thiol-terminated sulfur-containing prepolymer, a hydroxy vinyl ether, a diisocyanate, 1,3-bis(vinylsulfonyl)-2-propanol (HO—CH(—CH$_2$—S(O)$_2$—CH=CH$_2$)$_2$), and optionally a polyfunctionalizing agent. Thus, a Michael acceptor-terminated urethane-containing prepolymer can comprise a prepolymer having the structure of Formula (25a), a prepolymer having the structure of Formula (25b), or a combination thereof:

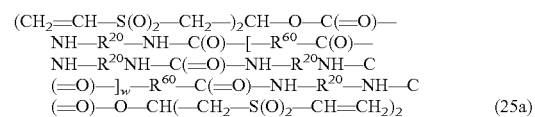
(25a)

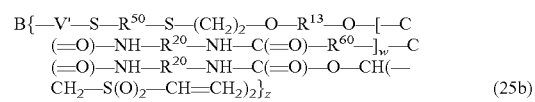
(25b)

where each $R^{13}$, each $R^{20}$, each $R^{50}$, each $R^{60}$, w, z, B, and each —V'— are as defined herein. In prepolymers of Formula (25a) and Formula (25b) each $R^{50}$ can have the structure of Formula (6).

In prepolymers of Formula (23a) and Formula (23b), each $R^{30}$ can comprise a terminal maleimide group or a terminal bismaleimide group.

Michael acceptor-terminated urethane-containing prepolymers can comprise the reaction product of reactants comprising an isocyanate-terminated urethane-containing adduct, and a compound comprising a group reactive with an isocyanate and at least one Michael acceptor group. Michael acceptor-terminated urethane-containing prepolymers can comprise the reaction product of reactants comprising an isocyanate-terminated urethane-containing adduct, and a compound comprising a group reactive with an isocyanate; at least one Michael acceptor group; and at least one metal ligand.

A Michael acceptor-terminated urethane-containing prepolymer may be prepared by reacting an isocyanate-terminated urethane-containing adduct with a compound having at least one Michael acceptor group, and optionally a metal ligand group, and a group reactive with the isocyanate group such as a hydroxyl group. The reaction can take place at a suitable temperature such as from 50° C. to 100° C., for a suitable time such as from 0.5 hours to 5 hours, in the presence of a suitable catalyst such as dibutyltin-dilaurate.

An isocyanate-terminated urethane-containing adduct can comprise an isocyanate-terminated urethane-containing polythioether adduct, an isocyanate-terminated urethane-containing polysulfide adduct, or a combination of any of the foregoing.

Michael acceptor-terminated urethane-containing prepolymers provided by the present disclosure can be capped with a moiety having a group reactive with an isocyanate and at least one Michael acceptor group. The capping moiety can further include a metal ligand.

Groups reactive with isocyanate groups include hydroxy groups, amine groups, and thiol groups.

Each arm of a Michael acceptor-terminated urethane-containing prepolymer may be capped with from 1 to 4 Michael acceptor groups. For example, each arm of a Michael acceptor-terminated urethane-containing prepolymer can comprise one terminal Michael acceptor group or each arm of a Michael acceptor-terminated urethane-containing prepolymer can comprise two terminal Michael acceptor groups.

In prepolymers of Formula (23a) and Formula (23b), each $R^{30}$ can be derived from a bis(vinylsulfonyl)alkanol and has the structure of Formula (26):

$$-O-CH(-R^{10}-S(O)_2-CH=CH_2)_2 \quad (26)$$

where each $R^{10}$ is $C_{2-4}$ alkanediyl.

A compound comprising a group reactive with an isocyanate and at least one Michael acceptor group comprises a bis(vinylsulfonyl)alkanol.

A compound comprises a hydroxyl group and at least one Michael acceptor group.

Michael acceptor-terminated urethane-containing prepolymers provided by the present disclosure can be capped with a compound having a group reactive with an isocyanate, at least one Michael acceptor group, and at least one metal ligand.

A metal ligand is capable of coordinating to an aerospace surface.

A compound can comprise a hydroxyl group and two vinyl sulfonyl groups.

Particularly useful compounds that include two Michael acceptor groups, a metal ligand, and a hydroxyl group include bis(vinylsulfonyl)alkanols. The terminal vinylsulfonyl groups are Michael acceptors, the bis(sulfonyl) groups serve as a metal ligand, and the hydroxyl group can be reacted with the isocyanate groups of the isocyanate-terminated urethane-containing adduct.

A compound comprising a group reactive with an isocyanate, at least one Michael acceptor group, and at least one metal ligand, can comprise a bis(vinylsulfonyl)alkanol such as 1,3-bis(vinylsulfonyl)-2-propanol.

A Michael acceptor-terminated urethane-containing prepolymer can be terminated in a moiety comprising at least one Michael acceptor group and optionally at least one metal ligand and are bonded to isocyanate groups of the prepolymer via a urethane linkage.

Thus, a Michael acceptor/metal ligand containing compound can comprise a reactive hydroxyl group capable of reacting with terminal isocyanate groups of the isocyanate-terminated urethane-containing prepolymer precursor.

Incorporation of metal ligands into the backbone of a sulfur-containing prepolymer and/or terminating a sulfur-containing prepolymer with a metal ligand can improve the adhesion of coatings and sealants to metal surfaces formed using metal ligand-containing prepolymers.

Bis(sulfonyl)alkanols represent one type of metal ligand that may be incorporated into the backbone of a polymer or form a terminal group such as a sulfur-containing prepolymer to improve surface adhesion. Other metal ligands may also be incorporated into the backbone of a polymer to enhance surface adhesion. In aerospace sealant applications, the metal ligands may be selected from a ligand capable of coordinating to aluminum, aluminum oxide, Al(III), anodized aluminum, titanium, titanium oxide, and/or Alodine® surfaces. The metal ligand may form a bidentate, tridentate, or higher order coordination complex to surface atoms.

Metal ligands and in particular aluminum (III) metal ligands include hard Lewis bases such as —OH, —PO$_4$, —SO$_4$, —COOH, —C=O, and —NH$_2$ groups, which are capable of donating electrons to vacant orbitals of the metal. Basic donor groups effective in forming multidentate coordination complexes with aluminum (III) include aliphatic monohydroxy acid anions, catecholates, aromatic hydroxy acid anions, 3-hydroxy-4-pyridinones, hydroxamates, and 3-hydroxy-2-pyridinones. Stable aluminum (III) complexes are with multidentate ligands having negative oxygen electron donors. A metal ligand may form a multidentate complex such as a bidentate complex or a tridentate complex with the metal.

A metal ligand functional group can be derived from a metal chelating agent selected from a bis(sulfonyl)alkanol, a hydroxypyridinone, and an acetylacetonate.

Examples of aluminum, aluminum oxide and Al(III) chelating agents include 2,3-dihydroxybenzoic acid, 5-nitrosalicylate, 3-hydroxy-4-pyridinone, 3-hydroxy-2-pyridinone, 2-2'-dihydroxyazobenzene, 8-hydroxyquinoline, oxylate, malonate, citrate, inimodiacetic acid, picolinic acid, maltol, kojic acid, N,N'-diacetic acid (EDTA), N-(2-hydroxy)ethylenediamenetriacetic acid (HEDTA), ethylenediamine-N,N'-bis(2-hydroxyphenylacetic acid (EDDHA), and N,N'-bis(hydroxybenzyl)ethylenediamine-N,N'-diacetic acid (HBED), acetoacetate, acetylacetonate, a catecholate, a hydroxamate, and a quinone. Other aluminum and aluminum oxide chelators are disclosed, for example, in Yokel, *Coordination Chemistry Reviews* 2002, 228, 97-113; and in Martell et al., *Coordination Chemistry Reviews* 1996, 149, 311-328.

Examples of titanium or titanium oxide metal ligands include H$_2$O$_2$, acetoacetonate (CH$_2$(COCH$_3$)$_2$), EDTA, trans-1,2-cyclohexanediamine tetraacetic acid, glycoletherdiamine tetracetic acid (GEDTA, (CH$_2$OCH$_2$CH$_2$N(CH$_2$COOH)$_2$)$_2$), diethylenetriamine pentaacetic acid (DTPA, HOOCH$_2$N(CH$_2$CH$_2$N(CH$_2$COOH)$_2$)$_2$), nitrile triacetic acid (NTA, N(CH$_2$COOH)$_3$), salicylic acid, lactic acid, acetoacetate, triethanolamine, and combinations of any of the foregoing.

A metal ligand can comprise at least two heteroatomic groups capable of coordinating to aluminum (III) surfaces. A metal ligand can comprise at least two heteroatomic groups selected from —OH, —PO$_4$, —P(O)$_2$—, —SO$_4$, —S(O)$_2$—, —COOH, —C=O, —NH$_2$, —NH—, and a combination of any of the foregoing.

A metal ligand functional group can comprise a moiety of Formula (27a), Formula (27b), Formula (27c), Formula (27d), Formula (27e), or a combination of any of the foregoing:

$$-X-(CH_2)_s-CH(-OH)- \quad (27a)$$

$$-X-(CH_2)_s-CH(-OH)-(CH_2)_n-X- \quad (27b)$$

—CH(—OH)—(CH$_2$)$_s$—X—(CH$_2$)$_s$—CH(—OH)— (27c)

—CH(—OH)—R$^5$—CH(—OH)— (27d)

—C(O)—R$^5$—C(O)— (27e)

where —X— is independently selected from —C(O)— or —S(O)$_2$—; each s is independently selected from 1, 2, and 3; and R$^5$ is a C$_{1-3}$ alkanediyl. Each X can be —C(O)— and each s can be 1; or each X can be —S(O)$_2$— and each s can be 1.

A metal ligand can comprise a bis(sulfonyl)alkanol, a hydroxypyridinone, a quinone, an acetylacetonate, or a combination of any of the foregoing.

In prepolymers of Formula (23a) and Formula (23b), each R$^{50}$ can be derived from a polythioether. For example, each R$^{50}$ can comprise the structure of Formula (6):

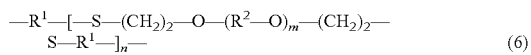

where,
each R$^1$ independently is selected from C$_{2-10}$ alkanediyl, C$_{6-8}$ cycloalkanediyl, C$_{6-14}$ alkanecycloalkanediyl, C$_{5-8}$ heterocycloalkanediyl, and -[(—CHR$^3$—)$_p$—X—]$_q$—(—CHR$^3$—)$_r$—, wherein,
p is an integer from 2 to 6;
q is an integer from 1 to 5;
r is an integer from 2 to 10;
each R$^3$ is independently selected from hydrogen and methyl; and
each X is independently selected from —O—, —S—, and —NR—, wherein R is selected from hydrogen and methyl;
each R$^2$ is independently selected from C$_{1-10}$ alkanediyl, C$_{6-8}$ cycloalkanediyl, C$_{6-14}$ alkanecycloalkanediyl, and -[(—CHR$^3$—)$_p$—X—]$_q$—(—CHR$^3$—)$_r$—, wherein p, q, r, R$^3$, and X are as defined as for R$^1$;
m is an integer from 0 to 50; and
n is an integer from 1 to 60.

In prepolymers of Formula (23a) and Formula (23b), w can be an integer from 2 to 50, such as from 2 to 20.

Compositions provided by the present disclosure may further comprise one or more Michael acceptor compounds and/or one or more polythiols.

When a composition comprises a polyfunctional monomeric Michael acceptor, a suitable monomeric Michael acceptor having at least two Michael acceptor groups such as, for example, divinyl sulfone or other Michael acceptors including any of those disclosed herein may be used.

A polyfunctional Michael acceptor compound has at least two Michael acceptor groups. A polyfunctional Michael acceptor may have an average Michael acceptor functionality from 2 to 6, from 2 to 4, from 2 to 3, or from 2.05 to 2.5. A polyfunctional Michael acceptor can be difunctional, such as, divinyl ketone and divinyl sulfone. A Michael acceptor compound having a functionality greater than two may be prepared by reacting a compound having a Michael acceptor group and a group reactive with terminal groups of a polyfunctionalizing agent such as those disclosed herein, using appropriate reaction conditions.

In compositions where a monomeric Michael acceptor compound is used, the molecular weight of the Michael acceptor can be less than 600 Daltons, less than 400 Daltons, or less than 200 Daltons.

A Michael acceptor compound can comprise from 0.5 wt % to 20 wt % of the composition, from 1 wt % to 10 wt %, from 2 wt % to 8 wt %, from 2 wt % to 6 wt %, or from 3 wt % to 5 wt %, where wt % is based on the total dry solids weight of the composition.

A polythiol may be a small molecule such as compound having a molecular weight less than 400 Daltons, a prepolymer, or a combination thereof. For example, a polythiol may be a dithiol of Formula (16) such as, for example, DMDO, a polythiol of Formula (18), or a combination of any of the foregoing.

Compositions comprising a thiol-terminated prepolymer and a polyfunctional Michael acceptor curing agent can comprise an amine catalyst. Examples of suitable amine catalysts include, for example, triethylenediamine, 1,4-diazabicyclo[2.2.2]octane (DABCO), dimethylcyclohexylamine (DMCHA), dimethylethanolamine (DMEA), bis-(2-dimethylaminoethyl)ether, N-ethylmorpholine, triethylamine, 1,8-diazabicyclo[5.4.0]undecene-7 (DBU), pentamethyldiethylenetriamine (PMDETA), benzyldimethylamine (BDMA), N,N,N'-trimethyl-N'-hydroxyethyl-bis(aminoethyl)ether, and N'-(3-(dimethylamino)propyl)-N,N-dimethyl-1,3-propanediamine.

In practice, the foregoing compositions may be provided as two-part compositions in which a thiol-terminated sulfur-containing prepolymer and a Michael acceptor are provided as separate components, with the amine catalyst in one or both components, and the two parts are mixed shortly prior to use. For example, if the catalytic amine is a tertiary amine, the amine catalyst may be in one or both components, and if the catalytic amine is a primary or secondary amine, the amine catalyst can only be included in the component containing the thiol-terminated sulfur-containing prepolymer. Alternatively, the base catalyst may be provided as a third component, and the component containing the thiol-terminated sulfur-containing prepolymer, the component containing the Michael acceptor, and the component containing the base catalyst can be mixed shortly before use. However, once the components are mixed, the Michael addition reaction proceeds, and depending at least in part on the temperature and on the type of amine catalyst, the working time is limited to less than 2 hours. Furthermore, once the composition starts to cure, there is little ability to control the reaction rate to take advantage of the complex chemistries taking place after the sealant is applied to a surface.

Compositions provided by the present disclosure may comprise one or more additional components suitable for use in aerospace sealants and the selection and amounts can depend at least in part on the desired performance characteristics of the cured sealant under conditions of use. Compositions provided by the present disclosure may be formulated as a sealant or may be formulated as a coating.

Compositions provided by the present disclosure can comprise one or more than one adhesion promoters. An adhesion promoter may be present in amount from 0.1 wt % to 15 wt % of a composition, less than 5 wt %, less than 2 wt %, or less than 1 wt %, based on the total dry weight of the composition. Examples of suitable adhesion promoters include phenolics, such as Methylon® phenolic resin, and organosilanes, such as epoxy-, mercapto- or amino-functional silanes, such as Silquest® A-187 and Silquest® A-1100. Other useful adhesion promoters are known in the art.

Compositions provided by the present disclosure may comprise one or more different types of filler. Suitable fillers include those commonly known in the art, including inorganic fillers, such as carbon black and calcium carbonate (CaCO$_3$), silica, polymer powders, and lightweight fillers.

Suitable lightweight fillers include, for example, those described in U.S. Pat. No. 6,525,168. A composition can include from 5 wt % to 60 wt % of the filler or combination of fillers, 10 wt % to 50 wt %, or from 20 wt % to 40 wt %, based on the total dry weight of the composition. Compositions provided by the present disclosure may further include one or more colorants, thixotropic agents, accelerators, fire retardants, adhesion promoters, solvents, masking agents, or a combination of any of the foregoing. As can be appreciated, fillers and additives employed in a composition may be selected so as to be compatible with each other as well as the polymeric component, curing agent, and or catalyst.

Compositions provided by the present disclosure can include low density filler particles. As used herein, low density, when used with reference to such particles means that the particles have a specific gravity of no more than 0.7, or no more than 0.25, or no more than 0.1. Suitable lightweight filler particles often fall within two categories—microspheres and amorphous particles. The specific gravity of microspheres may range from 0.1 to 0.7 and include, for example, polystyrene foam, microspheres of polyacrylates and polyolefins, and silica microspheres having particle sizes ranging from 5 microns to 100 microns and a specific gravity of 0.25 (Eccospheres®). Other examples include alumina/silica microspheres having particle sizes in the range of 5 microns to 300 microns and a specific gravity of 0.7 (Fillite®), aluminum silicate microspheres having a specific gravity of from 0.45 to 0.7 (Z-Light®), calcium carbonate-coated polyvinylidene copolymer microspheres having a specific gravity of 0.13 (Dualite® 6001AE), and calcium carbonate coated acrylonitrile copolymer microspheres such as Dualite® E135, having an average particle size of 40 m and a density of 0.135 g/cc (Henkel). Suitable fillers for decreasing the specific gravity of the composition include, for example, hollow microspheres such as Expancel® microspheres (available from AkzoNobel) or Dualite® low density polymer microspheres (available from Henkel). Compositions provided by the present disclosure include lightweight filler particles comprising an exterior surface coated with a thin coating, such as those described in U.S. Application Publication No. 2010/0041839, which is incorporated by reference in its entirety.

A composition can comprise less than 2 wt % of a low density filler, less than 1.5 wt %, less than 1.0 wt %, less than 0.8 wt %, less than 0.75 wt %, less than 0.7 wt %, or less than 0.5 wt % of a low density filler, where wt % is based on the total dry solids weight of the composition.

Examples of electrically non-conductive fillers include materials such as calcium carbonate, mica, polyamide, fumed silica, molecular sieve powder, microspheres, titanium dioxide, chalks, alkaline blacks, cellulose, zinc sulfide, heavy spar, alkaline earth oxides, alkaline earth hydroxides, and the like. Fillers also include high band gap materials such as zinc sulfide and inorganic barium compounds. An electrically conductive base composition can comprise an amount of electrically non-conductive filler ranging from 2 wt % to 10 wt % based on the total weight of the base composition, or can range from 3 wt % to 7 wt %. A composition can comprise an amount of electrically non-conductive filler ranging from less than 6 wt % or can range from 0.5% to 4% by weight, based on the total weight of the composition.

Low density fillers can reduce the specific gravity of the composition. The specific gravity of a composition can be from 0.8 to 1, 0.7 to 0.9, from 0.75 to 0.85, or can be from 0.77 to 0.83. The specific gravity of a composition can be less than 0.9, less than 0.8, less than 0.75, less than 0.7, less than 0.65, less than 0.6, or less than 0.55.

Compositions provided by the present disclosure can comprise an electrically conductive filler. Electrical conductivity and EMI/RFI shielding effectiveness can be imparted to composition by incorporating conductive materials within the polymer. The conductive elements can include, for example, metal or metal-plated particles, fabrics, meshes, fibers, and combinations thereof. The metal can be in the form of, for example, filaments, particles, flakes, or spheres. Examples of metals include copper, nickel, silver, aluminum, tin, and steel. Other conductive materials that can be used to impart EMI/RFI shielding effectiveness to polymer compositions include conductive particles or fibers comprising carbon or graphite. Electrically conductive polymers such as polythiophenes, polypyrroles, polyaniline, poly(p-phenylene) vinylene, polyphenylene sulfide, polyphenylene, and polyacetylene can also be used.

Fillers used to impart electrical conductivity and EMI/RFI shielding effectiveness to polymer compositions are well known in the art. Examples of electrically conductive fillers include electrically conductive noble metal-based fillers such as pure silver; noble metal-plated noble metals such as silver-plated gold; noble metal-plated non-noble metals such as silver plated cooper, nickel or aluminum, for example, silver-plated aluminum core particles or platinum-plated copper particles; noble-metal plated glass, plastic or ceramics such as silver-plated glass microspheres, noble-metal plated aluminum or noble-metal plated plastic microspheres; noble-metal plated mica; and other such noble-metal conductive fillers. Non-noble metal-based materials can also be used and include, for example, non-noble metal-plated non-noble metals such as copper-coated iron particles or nickel plated copper; non-noble metals, e.g., copper, aluminum, nickel, cobalt; non-noble-metal-plated-non-metals, e.g., nickel-plated graphite and non-metal materials such as carbon black and graphite. Combinations of electrically conductive fillers can also be used to meet the desired conductivity, EMI/RFI shielding effectiveness, hardness, and other properties suitable for a particular application.

The shape and size of electrically conductive fillers used in the compositions of the present disclosure can be any appropriate shape and size to impart EMI/RFI shielding effectiveness to the cured composition. For example, fillers can be of any shape that is generally used in the manufacture of electrically conductive fillers, including spherical, flake, platelet, particle, powder, irregular, fiber, and the like. In certain sealant compositions of the disclosure, a base composition can comprise Ni-coated graphite as a particle, powder or flake. The amount of Ni-coated graphite in a base composition can range from 40 wt % to 80 wt %, or can range from 50 wt % to 70 wt %, based on the total weight of the base composition. An electrically conductive filler can comprise Ni fiber. Ni fiber can have a diameter ranging from 10 µm to 50 µm and have a length ranging from 250 µm to 750 µm. A base composition can comprise, for example, an amount of Ni fiber ranging from 2 wt % to 10 wt %, or from 4 wt % to 8 wt %, based on the total weight of the base composition.

Carbon fibers, particularly graphitized carbon fibers, can also be used to impart electrical conductivity to compositions of the present disclosure. Carbon fibers formed by vapor phase pyrolysis methods and graphitized by heat treatment and which are hollow or solid with a fiber diameter ranging from 0.1 micron to several microns, have high electrical conductivity. As disclosed in U.S. Pat. No. 6,184,280, carbon microfibers, nanotubes or carbon fibrils having an outer diameter of less than 0.1 μm to tens of nanometers can be used as electrically conductive fillers. An example of graphitized carbon fiber suitable for conductive compositions of the present disclosure include Panex® 30MF (Zoltek Companies, Inc. a 0.921 μm diameter round fiber having an electrical resistivity of 0.00055 Ω-cm.

The average particle size of an electrically conductive filler can be within a range useful for imparting electrical conductivity to a polymer-based composition. For example, the particle size of the one or more fillers can range from 0.25 μm to 250 μm, or can range from 0.25 μm to 75 μm, or can range from 0.25 μm to 60 μm. Compositions of the present disclosure can comprise Ketjenblack® EC-600 JD (AkzoNobel, Inc.), an electrically conductive carbon black characterized by an iodine absorption of 1,000 mg/g to 11,500 mg/g (J0/84-5 test method), and a pore volume of 480 $cm^3$/100 g to 510 $cm^3$/100 g (DBP absorption, KTM 81-3504). An electrically conductive carbon black filler is Black Pearls® 2000 (Cabot Corporation.).

Electrically conductive polymers can be used to impart or modify the electrical conductivity of compositions of the present disclosure. Polymers having sulfur atoms incorporated into aromatic groups or adjacent to double bonds, such as in polyphenylene sulfide, and polythiophene, are known to be electrically conductive. Other electrically conductive polymers include, for example, polypyrroles, polyaniline, poly(p-phenylene) vinylene, and polyacetylene. The sulfur-containing polymers forming a base composition can be polysulfides and/or polythioethers. As such, the sulfur-containing prepolymers can comprise aromatic sulfur groups and sulfur atoms adjacent to conjugated double bonds such as vinylcyclohexene-dimercaptodioxaoctane groups, to enhance the electrical conductivity of the compositions of the present disclosure.

Compositions of the present disclosure can comprise more than one electrically conductive filler and the more than one electrically conductive filler can be of the same or different materials and/or shapes. For example, a sealant composition can comprise electrically conductive Ni fibers, and electrically conductive Ni-coated graphite in the form of powder, particles or flakes. The amount and type of electrically conductive filler can be selected to produce a sealant composition which, when cured, exhibits a sheet resistance (four-point resistance) of less than 0.50 Ω/$cm^2$, or a sheet resistance less than 0.15 Ω/$cm^2$. The amount and type of filler can also be selected to provide effective EMI/RFI shielding over a frequency range of from 1 MHz to 18 GHz for an aperture sealed using a sealant composition of the present disclosure.

Galvanic corrosion of dissimilar metal surfaces and the conductive compositions of the present disclosure can be minimized or prevented by adding corrosion inhibitors to the composition, and/or by selecting appropriate conductive fillers. Corrosion inhibitors include strontium chromate, calcium chromate, magnesium chromate, and combinations thereof. U.S. Pat. No. 5,284,888 and U.S. Pat. No. 5,270,364 disclose the use of aromatic triazoles to inhibit corrosion of aluminum and steel surfaces. A sacrificial oxygen scavenger such as Zn can be used as a corrosion inhibitor. An electrically conductive composition can comprise less than 10 wt % by weight, such as from 2 wt % to 8 wt % of a corrosion inhibitor. Corrosion between dissimilar metal surfaces can also be minimized or prevented by the selection of the type, amount, and properties of the conductive fillers comprising the composition.

A sulfur-containing prepolymer and thiol-terminated prepolymer can make up from 50 wt % to 90 wt % of a composition, from 60 wt % to 90 wt %, from 70 wt % to 90 wt %, or from 80 wt % to 90 wt % of the composition, where wt % is based on the total dry solids weight of the composition.

Compositions provided by the present disclosure may be used, for example, in sealants, coatings, encapsulants, and potting compositions. A sealant includes a composition capable of producing a film or a coating that has the ability to resist operational conditions, such as moisture and temperature, and at least partially block the transmission of materials, such as water, fuel, and other liquid and gases. A coating composition includes a covering that is applied to the surface of a substrate to, for example, improve the properties of the substrate such as the appearance, adhesion, wettability, corrosion resistance, wear resistance, fuel resistance, and/or abrasion resistance. A potting composition includes a material useful in an electronic assembly to provide resistance to shock and vibration and to exclude moisture and corrosive agents. Sealant compositions provided by the present disclosure are useful, e.g., as aerospace sealants and as linings for fuel tanks.

Compositions, such as sealants, may be provided as multi-pack compositions, such as two-pack compositions, wherein one package comprises one or more components comprising a thiol-terminated sulfur-containing prepolymer and a second package comprises a curing agent and/or an ionic liquid catalyst. Additives and/or other materials may be added to either or both packages as desired or necessary. The two packages may be combined and mixed prior to use. The working time of the combined composition is at least 12 hours, at least 24 hours, at least 48 hours, at least 72 hours, or more than 72 hours.

Compositions, including sealants, provided by the present disclosure may be applied to any of a variety of substrates. Examples of substrates to which a composition may be applied include metals such as titanium, stainless steel, and aluminum, any of which may be anodized, primed, organic-coated or chromate-coated; epoxy; urethane; graphite; fiberglass composite; Kevlar®; acrylics; and polycarbonates. Compositions provided by the present disclosure may be applied to a coating on a substrate, such as a polyurethane coating.

Compositions provided by the present disclosure may be applied directly onto the surface of a substrate or over an underlayer by any suitable coating process known to those of ordinary skill in the art.

Furthermore, methods are provided for sealing an aperture utilizing a composition provided by the present disclosure. These methods comprise, for example, applying a composition provided by the present disclosure to a surface to seal an aperture, and curing the composition. Methods for sealing an aperture can comprise (a) applying a sealant composition provided by the present disclosure to one or more surfaces defining an aperture, (b) assembling the surfaces defining the aperture, and (c) curing the sealant, to provide a sealed aperture. Methods of sealing a part provided by the present disclosure comprise providing a curable composition comprising an ionic liquid catalyst; applying the composition of claim 16 to at least a portion of a surface of a part; and curing the applied composition to seal the part.

Methods of using a composition provided by the present disclosure comprise applying a composition to a substrate; and allowing the composition to cure to provide a cured sealant. Methods of using a composition provided by the present disclosure comprise applying a composition to a substrate, wherein the phosphine catalyst comprises a controlled-release encapsulated ionic liquid catalyst; activating the controlled release ionic liquid catalyst; and allowing the composition to cure to provide a cured sealant.

Sealants provided by the present disclosure can be suitable for as Class A, Class B, or Class C aerospace sealants. A Class A sealant is typically applied by brushing and has a viscosity from about 150 Poise to 500 Poise. A Class B sealant can be applied by extrusion such as by extrusion suing a pneumatic Semco® gun and is characterized by a high viscosity from about 8,000 Poise to about 16,000 Poise. A Class B sealant can be used for forming fillets and sealing on vertical surfaces where low slump/sag is required. A Class C sealant can be applied using a roller coating or a combed tooth spreader and has a medium viscosity from about 1,000 Poise to about 4,000 Poise. A Class C sealant is used for sealing fay surfaces.

Compositions may be cured under ambient conditions, where ambient conditions refers to a temperature from 20° C. to 25° C., and atmospheric humidity. Compositions may be cured under conditions encompassing a temperature from a 0° C. to 100° C. and humidity from 0% relative humidity to 100% relative humidity. A composition may be cured at a higher temperature such as at least 30° C., at least 40° C., or at least 50° C. A composition may be cured at room temperature, e.g., 25° C. A composition may be cured upon exposure to actinic radiation, such as ultraviolet radiation. As will also be appreciated, the methods may be used to seal apertures on aerospace vehicles including aircraft and aerospace vehicles.

A composition achieves a tack-free cure in less than 1 hour, in less than 2 hours, less than t 4 hours, less than 6 hours, or less than 12 hours, after the useful working time of the composition.

The time to form a viable seal using curable compositions of the present disclosure can depend on several factors as can be appreciated by those skilled in the art, and as defined by the requirements of applicable standards and specifications. In general, curable compositions of the present disclosure develop adhesion strength within 24 hours to 30 hours, and 90% of full adhesion strength develops from 2 days to 3 days, following application to a surface. In general, full adhesion strength as well as other properties of cured compositions of the present disclosure becomes fully developed within 2 to 3 days following mixing and application of a curable composition to a surface.

After a curable composition provided by the present disclosure is prepared, the reactants begin to react, increasing the viscosity of the curable composition. The time during which the curable composition can be applied to a surface is referred to as the working time. At some point during the cure, the viscosity of the composition increases to the point that the composition can no longer be applied to a surface. After the composition is applied to a surface the curing reaction proceeds to a point at which the surface is no longer tacky (tack free) and then a point at which a hardness can be measured, which is referred to as the onset of cure. The sealant continues to cure and harden over time. Full cure then develops over several days, and for sealants provided by the present disclosure can reach a Shore A hardness of 40 or greater. In general, increasing amounts of an ionic liquid co-catalyst can reduce the onset of cure. The time the onset of cure will be reduced can depend on the curing chemistry.

The time between the onset of cure and the time when the curable composition exhibits a Shore A hardness of 20, 30, or 40 can be referred to as the curing time and can be characterized by a curing rate. In general, it is desired that the curing time be short and the curing rate be fast. Depending on the curing chemistry, the addition of an ionic liquid co-catalyst can reduce or can increase the curing time and curing rate. For example, in a $MnO_2$-catalyzed thiol condensation reaction, without an ionic liquid co-catalyst the onset of cure can be from 3 hours to 5 hours, and the time to reach a hardness of Shore A 40 from the onset of cure can be from 20 hours to 25 hours. Adding from 1 wt % to 5 wt % of an ionic liquid co-catalyst can reduce the onset of cure to 45 minutes to 90 minutes, and the curing time can be from 2 hours to 4 hours. In other $MnO_2$-catalyzed thiol condensation reactions the onset of cure can be reduced from about 6 hours to 7 hours, to 0.5 hours to 1.5 hours, and the curing time can be reduced from 12 hours to 18 hours to 1 hour to 3 hours.

The onset of cure and the cure time can also depend on the ionic liquid and on the particular ionic liquid anion. For example, when 0.3 wt % of the ionic liquid 1-butyl-3-methylimidazolium hexafluorophosphate ($[BMIM]^+$) is added to the $MnO_2$-catalyzed polysulfide sealant P/S 890 C24 Class C sealant, the onset of cure is reduced from about 7 days to between 0.5 to 6 hours depending on the anion, e.g., 0.5 hours for $[BMIM]^+CH_3COO^-$; 1.5 hours for $[BMIM]^+(CH_3)SO_4^-$; and 6 hours for $[BMIM]^+MBT^-$. The time to cure was also reduced from 48 hours for a sealant without 0.3 wt % ionic liquid catalyst to 1 hour with 0.3 wt % $[BMIM]+CH_3COO—$; 3 hours with 0.3 wt % $[BMIM]^+(CH_3)SO_4^-$; and 15 hours with 0.3 wt %$[BMIM]^+MBT^-$.

Sealants provided by the present disclosure can be suitable for as Grade A, Grade B, or Grade C aerospace sealants. For example, for aerospace sealant applications it can be desirable that a sealant meet the requirements of Mil-S-22473E (Sealant Grade C) at a cured thickness of 20 mils, exhibit an elongation greater than 200%, a tensile strength greater than 250 psi, and excellent fuel resistance, and maintain these properties over a wide temperature range from −67° F. (−55° C.) to 360° F. (182° C.). In general, the visual appearance of the sealant is not an important attribute. Prior to cure, it is desirable that the mixed components have a useful working time or working time of at least 24 hours and have a cure time within 48 hours to 72 hours of the working time. Useful working time or pot life refers to the time period the composition remains workable for application at ambient temperatures after the catalyst is released. Compositions provided by the present disclosure have a working time of at least 6 hours, at least 12 hours, at least 18 hours, at least 24 hours, at least 48 hours, or more than 24 hours. Compositions provided by the present disclosure cure in less than 6 hours after the onset of cure, in less than 12 hours, in less than 18 hours, in less than 24 hours, in less than 48 hours, or in less than 72 hours after the onset of cure.

Cured compositions disclosed herein, such as cured sealants, can exhibit properties acceptable for use in aerospace applications. In general, it is desirable that sealants used in aviation and aerospace applications exhibit the following properties: peel strength greater than 20 pounds per linear inch (pli) on Aerospace Material Specification (AMS) 3265B substrates determined under dry conditions, following immersion in JRF Type I for 7 days, and following immersion in a solution of 3% NaCl according to AMS 3265B test specifications; tensile strength between 300 pounds per square inch (psi) and 400 psi; tear strength greater than 50 pounds per linear inch (pli); elongation between 250% and 300%; and hardness greater than 40 Durometer A. These and other cured sealant properties appropriate for aerospace applications are disclosed in AMS 3265B, which is incorporated by reference in its entirety. It is also desirable that, when cured, compositions of the present disclosure used in aviation and aircraft applications exhibit a percent volume swell not greater than 25% following immersion for one week at 60° C. (140° F.) and ambient pressure in JRF Type I. Other properties, ranges, and/or thresholds may be appropriate for other sealant applications.

Compositions provided by the present disclosure are fuel-resistant. As used herein, the term "fuel resistant" means that a composition, when applied to a substrate and cured, can provide a cured product, such as a sealant, that exhibits a percent volume swell of not greater than 40%, in some cases not greater than 25%, in some cases not greater than 20%, in yet other cases not more than 10%, after immersion for one week at 140° F. (60° C.) and ambient pressure in Jet Reference Fluid (JRF) Type I according to methods similar to those described in ASTM D792 (American Society for Testing and Materials) or AMS 3269 (Aerospace Material Specification). Jet Reference Fluid JRF Type I, as employed for determination of fuel resistance, has the following composition: toluene: 28±1% by volume; cyclohexane (technical): 34±1% by volume; isooctane: 38±1% by volume; and tertiary dibutyl disulfide: 1±0.005% by volume (see AMS 2629, issued Jul. 1, 1989, § 3.1.1 etc., available from SAE (Society of Automotive Engineers)).

Compositions provided herein provide a cured product, such as a sealant, exhibiting a tensile elongation of at least 100% and a tensile strength of at least 400 psi when measured in accordance with the procedure described in AMS 3279, § 3.3.17.1, test procedure AS5127/1, § 7.7.

Compositions provide a cured product, such as a sealant, that exhibits a lap shear strength of greater than 200 psi, such as at least 220 psi, at least 250 psi, and, in some cases, at least 400 psi, when measured according to the procedure described in SAE AS5127/1 paragraph 7.8.

A cured sealant comprising a composition provided by the present disclosure meets or exceeds the requirements for aerospace sealants as set forth in AMS 3277.

Apertures, fasteners, surfaces, joints, or other parts, including apertures, fasteners, surfaces, joints, or other parts of aerospace vehicles, sealed with compositions provided by the present disclosure are also disclosed.

An electrically conductive sealant composition provided by the present disclosure exhibits the following properties measured at room temperature following exposure at 500° F. (260° C.) for 24 hours: a surface resistivity of less than 1 ohms/square, a tensile strength greater than 200 psi, an elongation greater than 100%, and a cohesive failure of 100% measured according to MIL-C-27725.

A cured sealant provided by the present disclosure exhibits the following properties when cured for 2 days at room temperature, 1 day at 140° F. (60° C.), and 1 day at 200° F. (93° C.); a dry hardness of 49, a tensile strength of 428 psi, and an elongation of 266%; and after 7 days in JRF Type I, a hardness of 36, a tensile strength of 312 psi, and an elongation of 247%.

Compositions provided by the present disclosure exhibit a Shore A hardness (7-day cure) greater than 10, greater than 20, greater than 30, or greater than 40; a tensile strength greater than 10 psi, greater than 100 psi, greater than 200 psi, or greater than 500 psi; an elongation greater than 100%, greater than 200%, greater than 500%, or greater than 1,000%; and a swell following exposure to JRF Type I (7 days) less than 20%.

Addition of an ionic liquid catalyst to a curable sealant composition either alone or with a primary catalyst does not compromise properties the cured sealant such as tensile strength and elongation. The addition of an ionic liquid catalyst to a curable sealant composition also does not appreciably change the percent swell following immersion in water or AMS2629 JRF Type I determined according to AS5127/1B sec. 7.5.

EXAMPLES

Embodiments provided by the present disclosure are further illustrated by reference to the following examples, which describe the preparation and properties of certain compositions containing thiol-terminated sulfur-containing prepolymers, curing agents, and ionic liquid catalysts. It will be apparent to those skilled in the art that many modifications, both to materials, and methods, may be practiced without departing from the scope of the disclosure.

Example 1

Ionic Liquid Co-Catalyst, Manganese Dioxide-Cured Polysulfide Sealant

The effect of an ionic liquid catalyst on the curing rate of a polysulfide-based sealant composition was evaluated. Various amounts of the ionic liquid 1-ethyl-3-methyl imidazolium ethyl sulfate were added to of the Class A fuel tank sealant PR-1440, commercially available from PRC-DeSoto International. PR-1440 is a two-part, Class A manganese dioxide-cured polysulfide sealant that is curable at room temperature. Formulations having 0 wt %, 1.0 wt %, 2.5 wt %, 5 wt %, 7 wt %, and 10 wt % of the ionic liquid co-catalyst were prepared, where wt % is based on the total solids weight of the composition. The formulations were spread onto aluminum substrates and cured at room temperature.

Figure 2:
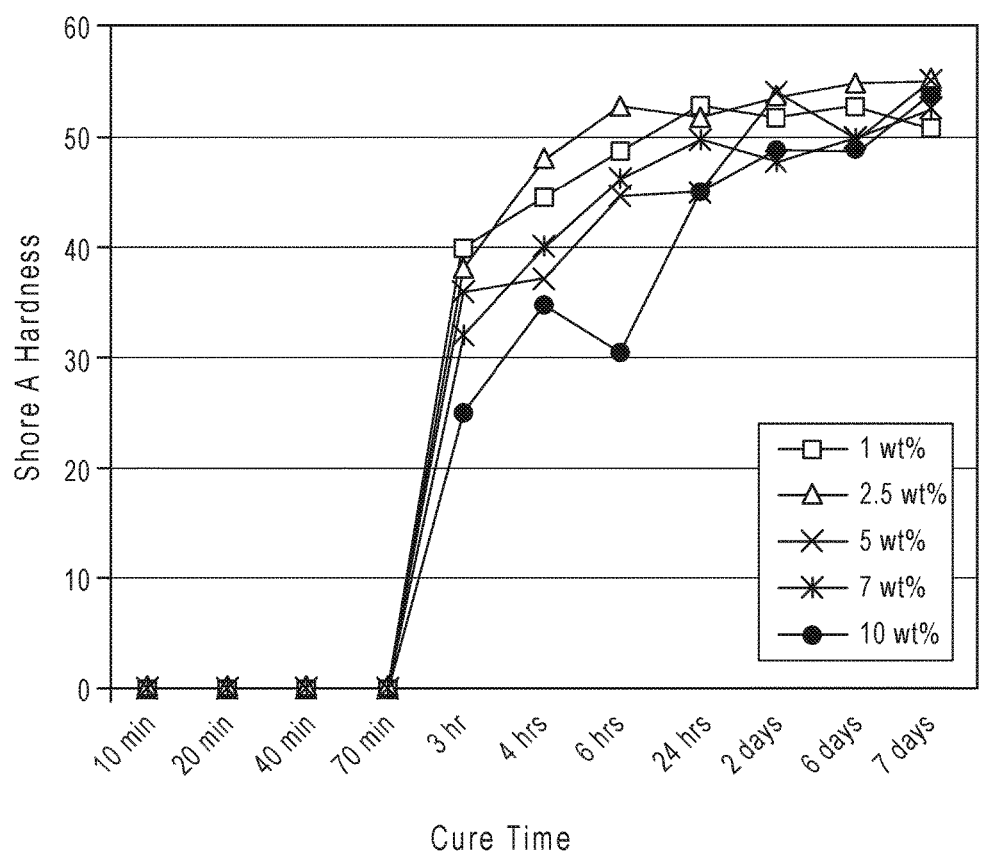
FIG. 2 shows the Shore A hardness during cure of a manganese dioxide-cured polysulfide sealant composition with various amounts of an ionic liquid co-catalyst.

The PR-1440 formulation without (0 wt %) ionic liquid cured to a Shore A hardness of 40 within 24 hours. In contrast, the samples containing from 1 wt % to 10 wt % ionic liquid cured to a Shore A hardness of 40 within 3 hours. The results are presented in Table 1 and in FIG. 1 and FIG. 2.

TABLE 1

Shore A hardness of PR-1440 sealant during cure.

| wt % Ionic Liquid | Shore A 40 Hardness at Time after Mixing | | | | | | |
|---|---|---|---|---|---|---|---|
| | 2 hr | 3 hr | 4 hr | 6 hr | 24 hr | 48 hr | 7 days |
| 0 | 0 | 0 | 0 | 2 | 34 | 55 | 52 |
| 1 | 0 | 40 | 44 | 49 | 53 | 52 | 51 |
| 2.5 | 0 | 38 | 48 | 53 | 52 | 54 | 55 |
| 5 | 0 | 36 | 37 | 45 | 45 | 54 | 55 |
| 7 | 0 | 32 | 40 | 46 | 50 | 48 | 53 |
| 10 | 0 | 25 | 35 | 30 | 45 | 49 | 54 |

Example 2

Ionic Liquid Co-Catalyst, Manganese Dioxide-Cured Polysulfide Sealant

P/S 890 B-2 is a class B fuel tank sealant commercially available from PRC-DeSoto International. The sealant is a two-part, manganese dioxide-cured polysulfide composition capable of curing at room temperature.

A sealant prepared using P/S 890 B-2 (62.7 g of the Base Pack and 7.25 g of the Accelerator Pack) served as the control. The test composition was prepared by mixing 3.625 g of ionic liquid (1-butyl-3-methylimidazolium methyl sulfate) (5 wt %) with 62.7 g of the P/S 890 B-2 Base Pack. The Accelerator Pack (7.25 g) was added and mixed with the ionic liquid-containing Base Pack.

Figure 3:
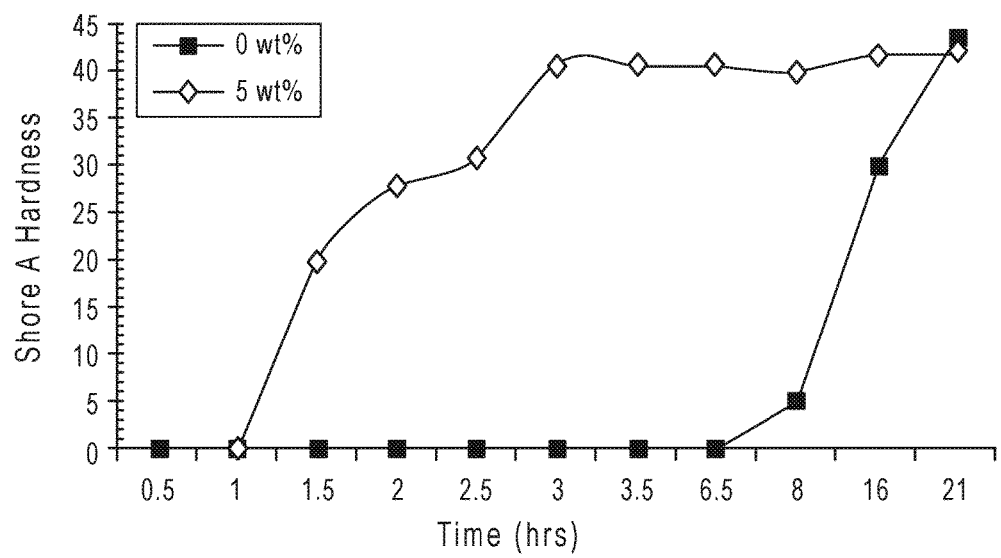
FIG. 3 is a graph showing the Shore A hardness of P/S 890 B-2 sealants during cure with and without an ionic liquid co-catalyst.

The compositions were cured at room temperature and the Shore A hardness measured at intervals. The results are shown in FIG. 3. The composition without the ionic liquid (control) exhibited a curing onset after 7 hours and cured to a Shore A hardness of 40 by 21 hours after mixing. Curing onset was defined as the time at which there was a measurable hardness. The composition with 5 wt % ionic liquid exhibited a curing onset within 1.25 hours and cured to a Shore A hardness of 40 within 3 hours.

Example 3

Ionic Liquid-Catalyzed Michael Addition-Cured Polythioether Sealant

A polythioether composition was prepared that included the components in Table 2.

TABLE 2

Polythioether composition of Example 3.

| Description | Amount (g) |
|---|---|
| Permapol ® 3.1e* | 25.25 |
| Permapol ® P3.1** | 5.60 |
| HB-40† | 0.74 |
| Tung Oil | 0.40 |

*Permapol ® 3.1e, thiol-terminated polythioether available from PRC-DeSoto International, Inc.
**Permapol ® 3.1, thiol-terminated polythioether available from PRC-DeSoto International, Inc.
†HB-40, hydrogenated terphenyl and partially hydrogenated quaterphenyls and higher polyphenyls, plasticizer available from Eastman Chemical Co.

Curable sealant compositions were prepared by mixing the polythioether composition of Table 2 (Polythioether Component) with either divinyl sulfone only (Sealant 1) or with divinyl sulfone and 0.1 wt % ionic liquid (1-butyl-3-methyl-imidazolium acetate) (Sealant 2) in the amounts shown in Table 3.

TABLE 3

Curable sealant composition of Example 3.

| Sealant | Polythioether Component (g) | Divinyl Sulfone (g) | Ionic Liquid (g) |
|---|---|---|---|
| 1 | 19.188 | 0.758 | 0.000 |
| 2 | 11.880 | 0.470 | 0.012 |

Figure 4:
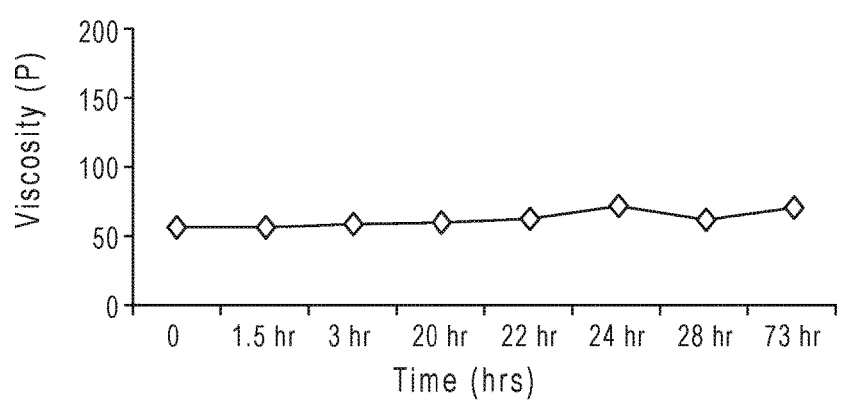
FIG. 4 shows the viscosity with time of a Michael addition-cured polythioether composition without an ionic liquid co-catalyst and with an amine catalyst.

Sealant 2, with 0.1 wt % ionic liquid, immediately cured into a ball when the divinyl sulfone was added to the polythioether composition. In contrast, as indicated by the viscosity of 65 Poise, the composition without the ionic liquid (Sealant 1) did not cure even after 72 hours (end of test). The viscosity of Sealant 1 with time following mixing is shown in FIG. 4.

Example 4

Ionic Liquid Co-Catalyst, Manganese Dioxide-Cured Polysulfide Sealant

Various amounts of the ionic liquid 1-ethyl-3-methylimidazolium ethyl sulfate were added to a manganese dioxide-cured polysulfide sealant, P/S 890 C24, Class C, fuel tank sealant, available from PRC-DeSoto International.

Figure 5:
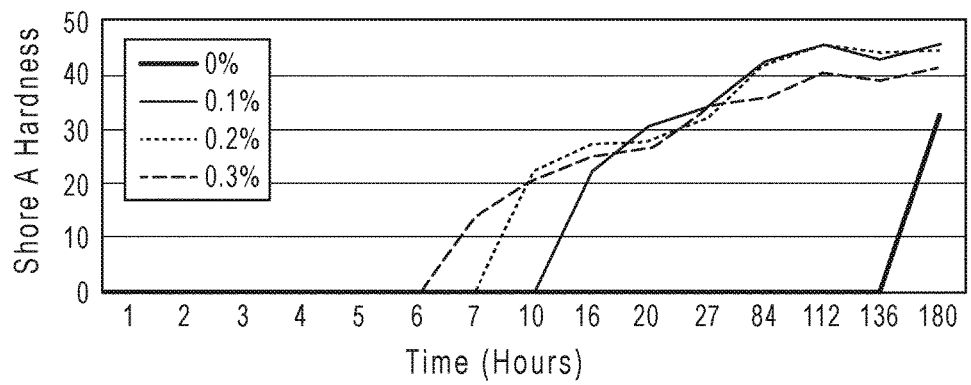
FIG. 5 shows the Shore A hardness during cure of a manganese dioxide-cured polysulfide sealant composition with different amounts of an ionic liquid co-catalyst.

As shown in FIG. 5, without the ionic liquid, the sealant did not begin to cure until about 5.7 days (136 h) after mixing. With the addition of from 0.1 wt % to 0.3 wt % of the ionic liquid, the onset of cure decreased to from 6.5 hours and to 10 hours.

The curing dynamics of the manganese dioxide-cured polysulfide sealant was further investigated by varying the amounts of both the manganese dioxide and the ionic liquid, 1-ethyl-3-methylimidazolium ethyl sulfate. Table 4 shows the time to the first measurable Shore A hardness reading (working time) after the base and accelerator components were combined to provide the curable sealant formulation.

TABLE 4

| Added | Working Time. | | | |
|---|---|---|---|---|
| | wt % Ionic Liquid | | | |
| wt % $MnO_2$ | 0 wt % | 0.1 wt % | 0.2 wt % | 0.3 wt % |
| 0 | 180 h | 16.5 h | 10 h | 7.5 h |
| 25 | 16.5 h | 5.25 h | 3 h | 3 h |
| 45 | 10.5 h | 3 h | 3 h | 2 h |
| 100 | 4.5 h | 1 h | — | 0.25 h |

In Table 4, added wt % $MnO_2$ refers to the weight percent $MnO_2$ relative to the normal amount of $MnO_2$ in the P/S 890 C24 composition, and wt % ionic liquid refers to the amount of ionic liquid based on the total weight of the curable sealant composition. The results presented in Table 4 show that the curing onset time and the cure rate can be changed by using different amounts of manganese dioxide and/or ionic liquid co-catalyst.

Figure 6:
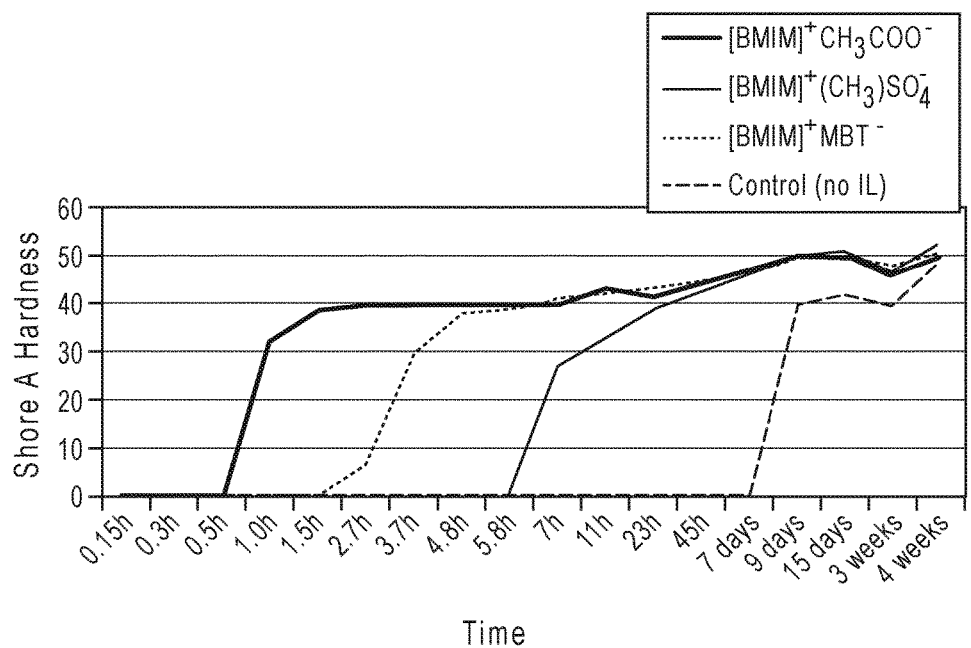
FIG. 6 shows the Shore A hardness during cure of a manganese dioxide-cured polysulfide sealant composition with different ionic liquid co-catalysts.

Using the same sealant formulation, the time to onset of cure was determined for various ionic liquids. The formulation contained 100% of the nominal amount of the $MnO_2$ catalyst and 0.3 wt % of different ionic liquid co-catalysts. Each of the ionic liquids had the same cation, 1-butyl-3-methylimidazolium hexafluorophosphate ([BMIM]$^+$), with a different anion $CH_3COO^-$, $(CH_3)SO_4^-$, or $MBT^-$. The results are presented in FIG. 6. Each of the ionic liquids tested decreased the time to measurable hardness. The cure onset time and the cure rate varied depending on the anion.

Figure 7:
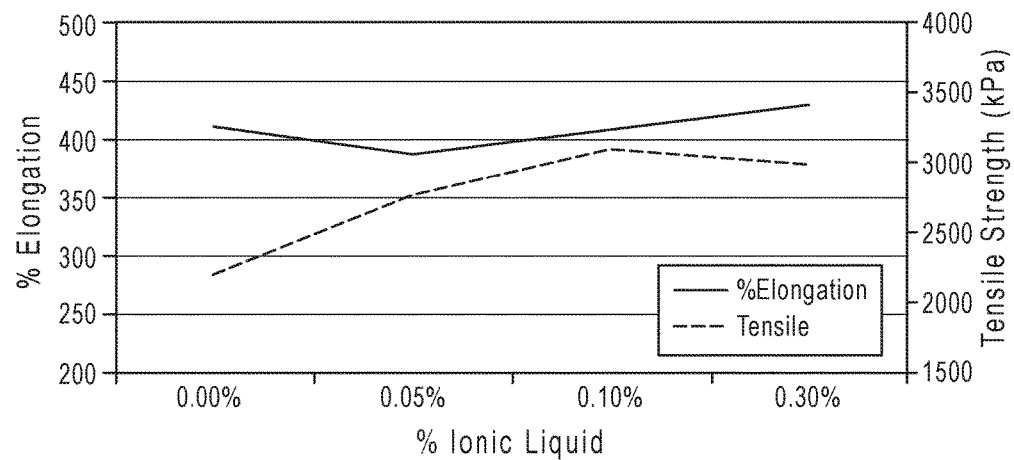
FIG. 7 shows the tensile strength and elongation of a cured manganese dioxide-cured polysulfide sealant without an ionic liquid co-catalyst and with different amounts of an ionic liquid co-catalyst.

FIG. 7 shows the tensile strength and elongation of the cured sealant with various amounts of the ionic liquid 1-ethyl-3-methylimidazolium ethyl sulfate. The results shown in FIG. 7 demonstrate that the addition of up to 0.3 wt % of an ionic liquid co-catalyst did not dramatically affect the % elongation, however, increasing amounts of the ionic liquid co-catalyst resulted in an increase in the tensile strength compared to a composition with only the manganese dioxide curing agent.

Example 5

Ionic Liquid-Catalyzed Polyepoxide-Cured Polythioether Sealant

The influence of the ionic liquid 1-butyl-3-methylimidazolium acetate on working time (time to cure) and cure rate for the polyepoxide cured polythioether Class B sealant PR-2001 (available from PRC-DeSoto International, Inc.) was evaluated.

Figure 8:
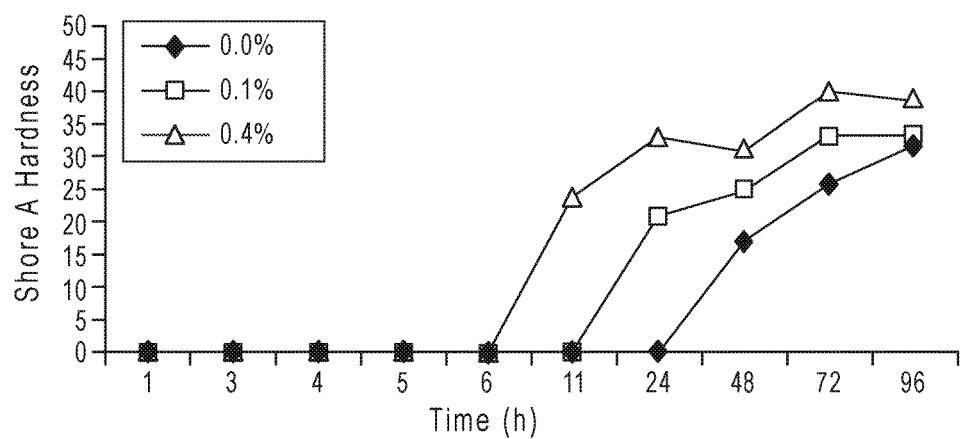
FIG. 8 shows the Shore A hardness during cure of an amine-catalyzed polyepoxide-cured thiol-terminated polythioether sealant without an ionic liquid co-catalyst and with different amounts of an ionic liquid co-catalyst.

PR-2001 is an amine (1,4-diazabicyclo[2.2.2]octane, DABCO) catalyzed polyepoxide-cured thiol-terminated polythioether sealant. The working time and curing rate for the sealant formulation with 0.1 wt % DABCO® 33LV, only, and in combination with 0.1 wt % or 0.4 wt % of the ionic liquid 1-butyl-3-methylimidazolium acetate are shown in FIG. 8. The addition of increasing amounts of the ionic liquid co-catalyst reduced the working time. The cure rate (time from initial hardness measurement to Shore A 20) for the various combinations was about 4 hours (0 wt % ionic liquid), about 13 hours (0.1 wt % ionic liquid), and about 36 hours (0.4 wt % ionic liquid). The cure rate (time from initial hardness measurement to Shore A 30) for the various combinations was about 12 hours (0 wt % ionic liquid), about 48 hours (0.1 wt % ionic liquid), and about 70 hours (0.4 wt % ionic liquid).

Figure 9:
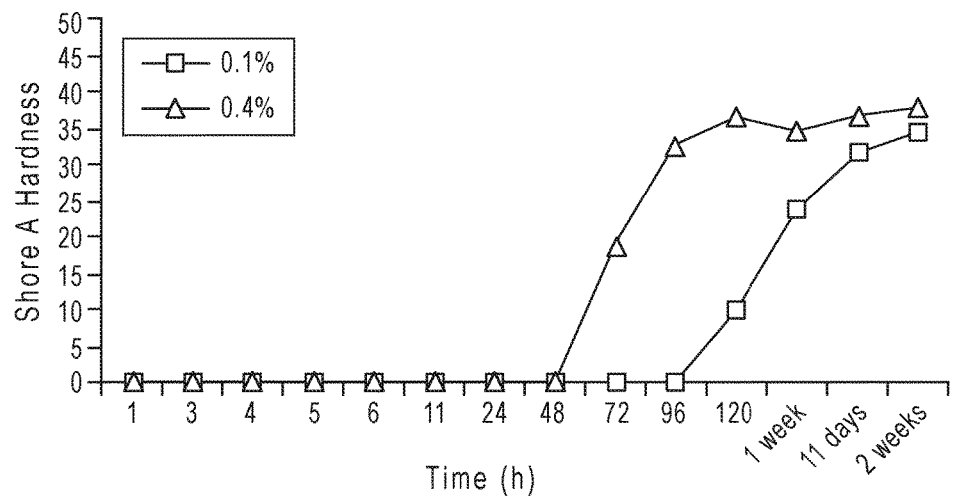
FIG. 9 shows the Shore A hardness during cure of an amine-catalyzed polyepoxide-cured thiol-terminated polythioether sealant with different amounts of an ionic liquid co-catalyst.

The working time and cure rate for the sealant formulation without the amine catalyst and with either 0.1 wt % or 0.4 wt % of the ionic liquid 1-butyl-3-methylimidazolium acetate are shown in FIG. 9. The addition of increasing amounts of the ionic liquid co-catalyst reduced the working time. However, with only an ionic liquid, the time to cure is slow, being from about 24 hours (0.4 wt % ionic liquid) to about 100 hours (0.1 wt % ionic liquid).

The curing dynamics of the epoxy-cured polythioether sealant was further investigated by varying the amounts of both the amine catalyst DABCO® 33LV and the ionic liquid, 1-butyl-3-methylimidazolium acetate. Table 5 shows the time to the first measurable hardness reading after the base and accelerator components to provide the curable sealant formulation were combined.

TABLE 5

Time to onset of cure.

| wt % DABCO® 33LV | wt % Ionic Liquid | | |
|---|---|---|---|
| | 0 wt % | 0.1 wt % | 0.4 wt % |
| 0 wt % | 240 h | 96 h | 48 h |
| 0.1 wt % | 48 h | 24 h | 11 h |
| 0.3 wt % | 4 h | 3 h | 3 h |
| 0.5 wt % | 3 h | 2 h | 2 h |

In Table 5, % DABCO® 33LV refers to the % wt based on the total weight of the curable composition, and wt % ionic liquid refers to the amount of ionic liquid based on the total weight of the curable sealant composition. The results in Table 5 show that the time to cure can be changed by using different amounts of the amine catalyst and ionic liquid co-catalyst. The presence of the ionic liquid allows for much lower amounts of the amine catalyst to achieve a similar working time.

Figure 10:
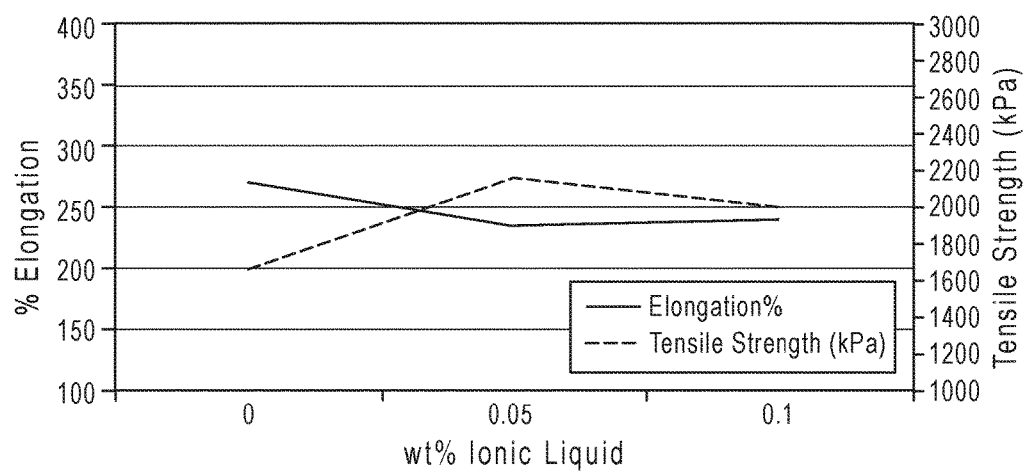
FIG. 10 shows the tensile strength and percent elongation of an amine-catalyzed polyepoxide-cured thiol-terminated polythioether sealant composition without an ionic liquid co-catalyst and with different amounts of an ionic liquid co-catalyst.

FIG. 10 shows the tensile strength and percent elongation of the cured sealant with various amounts of the ionic liquid 1-butyl-3-methylimidazolium acetate. The results shown in FIG. 10 demonstrate that the addition of up to 0.1 wt % of the ionic liquid did not affect the tensile strength and percent elongation compared to a composition with only the amine catalyst.

Example 6

Ionic Liquid Co-Catalyst, Manganese Dioxide-Cured Polysulfide Sealant—Fuel Resistance A sealant was prepared by combining an ionic liquid, butyl-3-methylimidazolium methyl sulfate, with P/S 890 B-2 base component in the amount specified in Table 6. The P/S 890 B-2 accelerator component was then added and the sealant tested for volume swell in accordance with AS5127/1B sec. 7.5. The results are presented in Table 6. P/S 890 B-2 is a Class B two-part, manganese dioxide-cured polysulfide-based aircraft integral fuel tank sealant available from PRC-DeSoto International.

TABLE 6

Fuel Resistance

| P/S 890 B-2 Base (g) | Ionic Liquid (g) | P/S 890 B-2 Accelerator (g) | Ionic Liquid (wt %) | % Swell H$_2$O | % Swell AMS2629 JRF Type I |
|---|---|---|---|---|---|
| 122.8 | 0 | 14.8 | 0 | 22.3 | 4.1 |
| 121.6 | 3.5 | 14.9 | 2.5 | 22.1 | 4.8 |
| 119.8 | 7.1 | 14.7 | 5.0 | 14.1 | 4.9 |

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A composition comprising:
    a thiol-terminated sulfur-containing prepolymer;
    a curing agent comprising two or more terminal groups reactive with thiol groups; and
    an ionic liquid catalyst.

2. The composition of claim 1, wherein the ionic liquid catalyst comprises an imidazolium ionic liquid catalyst.

3. The composition of claim 1, wherein the ionic liquid catalyst comprises 1-butyl-3-methylimidazolium acetate, 1-ethyl-3-methylimidazolium ethyl sulfate, or a combination thereof.

4. The composition of claim 1, wherein the ionic liquid catalyst comprises a controlled release ionic liquid catalyst.

5. The composition of claim 1, wherein the thiol-terminated sulfur-containing prepolymer comprises a thiol-terminated polythioether, a thiol-terminated polysulfide, a thiol-terminated sulfur-containing polyformal, or a combination of any of the foregoing.

6. The composition of claim 1, wherein the terminal groups reactive with thiol groups comprise thiol groups, epoxy groups, or Michael acceptor groups.

7. The composition of claim 1, wherein the curing agent comprises a polythiol, a polyepoxide, or a polyfunctional Michael acceptor.

8. The composition of claim 1, further comprising a primary catalyst.

9. The composition of claim 8, wherein the composition comprises from 0.01 wt % to 1 wt % of the ionic liquid catalyst, wherein wt % is based on the total solids weight of the composition.

10. The composition of claim 8, wherein the primary catalyst comprises an oxidizing agent.

11. The composition of claim 8, wherein,
    the thiol-terminated sulfur-containing prepolymer comprises a thiol-terminated polysulfide;
    the curing agent comprises a thiol-terminated polysulfide; and
    the primary catalyst comprises an oxidizing agent.

12. The composition of claim 8, wherein the primary catalyst comprises an amine catalyst.

13. The composition of claim 8, wherein,
the thiol-terminated sulfur-containing prepolymer comprises a thiol-terminated polythioether;
the curing agent comprises a polyepoxide; and
the primary catalyst comprises an amine.

14. The composition of claim 8, wherein the curing agent comprises a polyfunctional Michael acceptor.

15. The composition of claim 8, wherein,
the thiol-terminated sulfur-containing prepolymer comprises a thiol-terminated polythioether;
the curing agent comprises a comprises a polyfunctional Michael acceptor; and
the primary catalyst comprises an amine.

16. The composition of claim 1, formulated as a sealant.

17. A cured sealant prepared from the composition of claim 16.

18. A part comprising the cured sealant of claim 17.

19. A method of sealing a part, comprising:
applying the composition of claim 16 to at least a portion of a surface of a part; and
curing the applied composition to seal the part.

20. An aerospace vehicle comprising the cured sealant of claim 17.

21. The composition of claim 1, wherein the ionic liquid catalyst comprises a combination of a cation and an anion, wherein,
the cation comprises a mono-, di-, and tri-substituted imidazolium, a substituted pyridinium, a substituted pyrrolidinium, a tetraalkyl phosphonium, a tetraalkyl ammonium, a guanidinium, a isouronium; or a thiouronium; and
the anion comprises a chloride; a bromide; an iodide, a tetrafluoroborate, a hexafluorophosphate, a bis(trifluoromethylsulfonyl)imide, a tris(pentafluoroethyl)trifluorophosphate, a trifluoromethanesulfonate, a trifluoroacetate, a methylsulfate, a octylsulfate, a thiocyanate, organoborates, and a p-toluenesulfonate.

22. The composition of claim 1, wherein the ionic liquid catalyst comprises a combination of a cation and an anion, wherein,
the cation comprises an imidazolium cation, a pyridinium cation, a pyrrolidinium cation, a phosphonium cation, an ammonium cation, a sulfonium cation, or a combination of any of the foregoing; and
the anion comprises an alkylsulfate anion, a tosylate anion, a methane sulfonate anion, or a combination of any of the foregoing.

23. The composition of claim 1, wherein the ionic liquid catalyst comprises an imidazolium-based ionic liquid catalyst, a pyridinium-based ionic liquid catalyst, a pyrrolidinium-based ionic liquid catalyst, an ammonium-based ionic liquid catalyst, or a phosphonium-based ionic liquid catalyst.

24. The composition of claim 1, wherein the ionic liquid catalyst comprises 1-ethyl-3-methylimidazolium chloride, 1-ethyl-3-methylimidazolium methanesulfonate, 1-butyl-3-methylimidazolium chloride, 1-butyl-3-methylimidazolium methane sulfonate, methyl-tri-n-butylammonium methyl sulfate, 1,2,4-trimethylpyrazolium methylsulfate, 1-ethyl-2,3-di-methylimidazolium ethylsulfate, 1,2,3-trimethyl-imidazolium methylsulfate, methylimidazolium chloride, methylimidazolium hydrogen sulfate, 1-ethyl-3-methylimidazolium hydrogensulfate, 1-ethyl-3-methylimidazolium tetrachloroaluminate, 1-butyl-3-methylimidazolium hydrogen sulfate, 1-butyl-3-methylimidazolium tetrachloroaluminate, 1-ethyl-3-methylimidazolium acetate, 1-butyl-3-methylimidazolium acetate, 1-ethyl-3-methylimidazolium ethylsulfate, 1-butyl-3-methylimidazolium methyl sulfate, 1-ethyl-3-methylimidazolium thiocyanate, 1-butyl-3-methylimidazolium thiocyanate, or a combination of any of the foregoing.

25. The composition of claim 1, wherein, the ionic liquid catalyst is the only catalyst in the composition.

26. The composition of claim 1, wherein,
the ionic liquid catalyst is the only catalyst in the composition;
the composition comprises from 1 wt % to 15wt %; and
wt % is based on the total solids weight of the composition.

27. The composition of claim 1, wherein,
the composition comprises a primary catalyst; and
the composition comprises from 0.05 wt % to 3 wt % of the ionic liquid catalyst; and
wt % is based on the total solids weight of the composition.

* * * * *